United States Patent
Peled et al.

(10) Patent No.: US 7,344,881 B2
(45) Date of Patent: *Mar. 18, 2008

(54) METHODS OF EXPANDING STEM AND PROGENITOR CELLS AND EXPANDED CELL POPULATIONS OBTAINED THEREBY

(75) Inventors: Tony Peled, Mevaseret Zion (IL); Avi Treves, Mevaseret Zion (IL); Oren Rosen, Jerusalem (IL)

(73) Assignee: Gamida Cell Ltd., Jerusalem (IL)

( * ) Notice: Subject to any disclaimer, the term of this patent is extended or adjusted under 35 U.S.C. 154(b) by 582 days.

This patent is subject to a terminal disclaimer.

(21) Appl. No.: 10/418,639

(22) Filed: Apr. 18, 2003
(Under 37 CFR 1.47)

(65) Prior Publication Data

US 2004/0076603 A1    Apr. 22, 2004

Related U.S. Application Data

(63) Continuation of application No. PCT/IL03/00062, filed on Jan. 23, 2003.

(60) Provisional application No. 60/351,012, filed on Jan. 25, 2002.

(51) Int. Cl.
  C12N 5/00    (2006.01)
  C12N 5/08    (2006.01)
  C12N 5/02    (2006.01)

(52) U.S. Cl. .................. 435/325; 435/372; 435/375; 435/383

(58) Field of Classification Search ............ None
See application file for complete search history.

(56) References Cited

U.S. PATENT DOCUMENTS

| | | |
|---|---|---|
| 3,687,808 A | 8/1972 | Merigan, Jr. et al. |
| 4,036,945 A | 7/1977 | Haber |
| 4,331,647 A | 5/1982 | Goldenberg |
| 4,469,863 A | 9/1984 | Ts'o et al. |
| 4,476,301 A | 10/1984 | Imbach et al. |
| 4,642,120 A | 2/1987 | Nevo et al. |
| 4,687,808 A | 8/1987 | Jarrett et al. |
| 4,816,567 A | 3/1989 | Cabilly et al. |
| 4,866,052 A | 9/1989 | Hider et al. |
| 4,868,116 A | 9/1989 | Morgan et al. |
| 4,946,778 A | 8/1990 | Ladner et al. |
| 4,980,286 A | 12/1990 | Morgan et al. |
| 5,013,830 A | 5/1991 | Ohtsuka et al. |
| 5,023,243 A | 6/1991 | Tullis |
| 5,034,506 A | 7/1991 | Summerton et al. |
| 5,149,797 A | 9/1992 | Pederson et al. |
| 5,166,315 A | 11/1992 | Summerton et al. |
| 5,166,320 A | 11/1992 | Wu et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,321,131 A | 6/1994 | Agrawal et al. |
| 5,366,878 A | 11/1994 | Pedersen et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,434,257 A | 7/1995 | Matteucci et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Hule et al. |

(Continued)

FOREIGN PATENT DOCUMENTS

| | | |
|---|---|---|
| AU | 759522 | 8/1999 |
| AU | 770896 | 6/2000 |
| EP | 0 331 464 A2 | 9/1989 |
| WO | WO 89/02468 | 3/1989 |
| WO | WO 89/05345 | 6/1989 |
| WO | WO 89/07136 | 8/1989 |
| WO | WO 92/07573 | 5/1992 |

(Continued)

OTHER PUBLICATIONS

Peled et al Experimental Hematology, 2004, vol. 32, pp. 547-555.*

(Continued)

*Primary Examiner*—Michail Belyavskyi
(74) *Attorney, Agent, or Firm*—Ivor R. Elrifi; Matthew Pavao; Mintz, Levin, Cohn, Ferris, Glovsky and Popeo, P.C.

(57) ABSTRACT

Ex vivo and in vivo methods of expanding a population of stem and/or progenitor cells, while at the same time reversibly inhibiting differentiation of the stem and/or progenitor cells by providing the stem and/or progenitor cells with an effective amount of at least one copper chelate, so as to maintain a free copper concentration available to said cells substantially unchanged, to thereby expand the population of said stem and/or progenitor cells, while at the same time reversibly inhibit differentiation of said stem and/or progenitor cells.

30 Claims, 33 Drawing Sheets

U.S. PATENT DOCUMENTS

| | | |
|---|---|---|
| 5,476,925 A | 12/1995 | Letsinger et al. |
| 5,486,359 A | 1/1996 | Caplan et al. |
| 5,489,677 A | 2/1996 | Sanghvi et al. |
| 5,491,133 A | 2/1996 | Walder et al. |
| 5,519,126 A | 5/1996 | Hecht |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,350 A | 10/1996 | Kmiec |
| 5,569,825 A | 10/1996 | Lonberg et al. |
| 5,571,799 A | 11/1996 | Tkachuk et al. |
| 5,587,361 A | 12/1996 | Cook et al. |
| 5,596,086 A | 1/1997 | Mateucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,625,126 A | 4/1997 | Lonberg et al. |
| 5,631,219 A | 5/1997 | Rosenthal et al. |
| 5,633,360 A | 5/1997 | Bischofberger et al. |
| 5,633,425 A | 5/1997 | Lonberg et al. |
| 5,652,355 A | 7/1997 | Metelev et al. |
| 5,652,356 A | 7/1997 | Agrawal |
| 5,654,186 A | 8/1997 | Cerami et al. |
| 5,661,016 A | 8/1997 | Lonberg et al. |
| 5,663,312 A | 9/1997 | Chaturvedula |
| 5,677,437 A | 10/1997 | Teng et al. |
| 5,677,439 A | 10/1997 | Weis et al. |
| 5,700,922 A | 12/1997 | Cook |
| 5,714,331 A | 2/1998 | Buchardt et al. |
| 5,716,411 A | 2/1998 | Orgill et al. |
| 5,716,616 A | 2/1998 | Prockop et al. |
| 5,719,262 A | 2/1998 | Buchardt et al. |
| 5,736,396 A | 4/1998 | Bruder et al. |
| 5,741,899 A | 4/1998 | Capon et al. |
| 5,770,378 A | 6/1998 | Hwang et al. |
| 5,770,580 A | 6/1998 | Ledley et al. |
| 5,776,699 A | 7/1998 | Klein et al. |
| 5,789,245 A | 8/1998 | Dubensky, Jr. et al. |
| 5,789,543 A | 8/1998 | Ingham et al. |
| 5,792,751 A | 8/1998 | Ledley et al. |
| 5,814,482 A | 9/1998 | Dubensky, Jr. et al. |
| 5,830,760 A | 11/1998 | Tsai et al. |
| 5,837,544 A | 11/1998 | Capon et al. |
| 5,843,723 A | 12/1998 | Dubensky, Jr. et al. |
| 5,844,079 A | 12/1998 | Ingham et al. |
| 5,851,832 A | 12/1998 | Weiss et al. |
| 5,851,984 A | 12/1998 | Matthews et al. |
| 5,877,207 A | 3/1999 | Klein et al. |
| 5,945,309 A | 8/1999 | Ni et al. |
| 5,952,345 A | 9/1999 | Klein et al. |
| 5,958,954 A | 9/1999 | Klein et al. |
| 5,990,329 A | 11/1999 | Klaus et al. |
| 6,008,204 A | 12/1999 | Klein et al. |
| 6,015,686 A | 1/2000 | Dubensky, Jr. et al. |
| 6,015,694 A | 1/2000 | Dubensky, Jr. et al. |
| 6,063,797 A | 5/2000 | Fesus et al. |
| 6,077,947 A | 6/2000 | Capon et al. |
| 6,090,810 A | 7/2000 | Klein et al. |
| 6,117,850 A | 9/2000 | Patchen et al. |
| 6,130,230 A | 10/2000 | Chambon et al. |
| 6,133,309 A | 10/2000 | Bollag et al. |
| 6,165,747 A | 12/2000 | Ingham et al. |
| 6,218,128 B1 | 4/2001 | Klein et al. |
| 6,228,848 B1 | 5/2001 | Klein et al. |
| 6,232,291 B1 | 5/2001 | Ni et al. |
| 6,261,786 B1 | 7/2001 | Marigo et al. |
| 6,270,964 B1 | 8/2001 | Michnick et al. |
| 6,271,363 B1 | 8/2001 | Ingham et al. |
| 6,284,540 B1 | 9/2001 | Milbrandt et al. |
| 6,294,330 B1 | 9/2001 | Michnick et al. |
| 6,306,575 B1 | 10/2001 | Thomas et al. |
| 6,326,174 B1 | 12/2001 | Joyce et al. |
| 6,329,169 B1 | 12/2001 | Ni et al. |
| 6,338,942 B2 | 1/2002 | Kraus et al. |
| 6,342,219 B1 | 1/2002 | Thorpe et al. |
| 6,342,221 B1 | 1/2002 | Thorpe et al. |
| 6,342,372 B1 | 1/2002 | Dubensky, Jr. et al. |
| 6,342,581 B1 | 1/2002 | Rosen et al. |
| 6,372,210 B2 | 4/2002 | Brown |
| 6,372,473 B1 | 4/2002 | Moore et al. |
| 6,376,236 B1 | 4/2002 | Dubensky, Jr. et al. |
| 6,384,192 B1 | 5/2002 | Ingham et al. |
| 6,887,704 B2 | 5/2005 | Peled et al. |
| 6,962,698 B1 * | 11/2005 | Peled et al. .......... 424/93.7 |
| 2002/0114784 A1 | 8/2002 | Li et al. |
| 2002/0114789 A1 | 8/2002 | Peled et al. |
| 2002/0159981 A1 | 10/2002 | Peled et al. |
| 2003/0113913 A1 | 6/2003 | Purton et al. |
| 2005/0008624 A1 | 1/2005 | Peled et al. |
| 2005/0031595 A1 * | 2/2005 | Peled et al. .......... 424/93.7 |
| 2005/0054097 A1 | 3/2005 | Peled et al. |
| 2005/0054103 A1 | 3/2005 | Peled et al. |
| 2005/0118150 A1 | 6/2005 | Peled et al. |
| 2005/0214262 A1 | 9/2005 | Peled et al. |

FOREIGN PATENT DOCUMENTS

| | | |
|---|---|---|
| WO | WO 93/09220 | 5/1993 |
| WO | WO 97/31647 | 9/1997 |
| WO | WO 97/33978 | 9/1997 |
| WO | WO 97/41209 | 11/1997 |
| WO | WO 97/41224 | 11/1997 |
| WO | WO 98/25634 | 6/1998 |
| WO | WO 99/07831 | 2/1999 |
| WO | WO 99/18885 | 4/1999 |
| WO | WO 99/40783 | 8/1999 |
| WO | WO 00/18885 | 4/2000 |
| WO | WO 00/30635 | 6/2000 |
| WO | WO 03/062369 A2 | 7/2003 |
| WO | WO 03/062404 A1 | 7/2003 |
| WO | WO 03/078567 A2 | 9/2003 |
| WO | WO 2004/016731 A2 | 2/2004 |
| WO | WO 2004/078917 A2 | 9/2004 |

OTHER PUBLICATIONS

Burgada et al., Eur.J Org. Chem, 2001, pp. 349-352.*
Chelation Therapy, 2006, pp. 1-5.*
Van Epps, et al. (1994). *Blood Cells. 20*: 411-423.
Emerson. (1996). *Blood. 87*(8): 3082-3088.
Brugger, et al. (1995). *N. Engl. J. Med. 333*(5): 283-287.
Williams, et al. (1996). *Blood. 87*(5): 1687-1691.
Zimmerman, et al. (1996). *Journal of Hematotherapy, 5*: 247-253.
Koller, et al. (1993). *Blood. 82*(2): 378-384.
Lebkowski, et al. (1994). *Blood Cells. 20*:404-410.
Sandstrom, et al. (1995). *Blood. 86*(3): 958-970.
Eipers, et al. (1996). *Blood. 86*(10): 3754-3762.
Freedman, et al. (1996). *Nature Medicine. 2*(1): 46-51.
Hestop, et al. (1996). *Nature Medicine. 2*(5): 551-555.
Protti, et al. (1996). *Cancer Research. 56*: 1210-1213.
Rosenberg, et al. (1993). *Journal of the National Cancer Institute. 85*(8): 622-632.
Bernhard, et al. (1995). *Cancer Research. 55*: 1099-1104.
Fisch, et al. (1996). *Eur. J. Immunol. 26*: 595-600.
Siena, et al. (1995). *Experimental Hermatology. 23*: 1463-1471.

Petzer, et al. (1996). *J. Exp. Med. 183*:2551-2558.
Alter. (1979). *Experimental Hematology. 7*(5): 200-209.
Duncan, et al. (1997). *Molecular Medicine Today. 3*(12) :554-561.
Blau, et al. (1993). *Blood. 81*(1): 227-233.
Schechter, et al. (1987). *The Molecular Basis of Blood Diseases.* 179-218.
Ross, et al. (1969). *Analytical Chemistry. 41*(13): 1900-1902.
Sprangrude, et al. (1988). *Science. 241*: 58-62.
Morrison, et al. (1994). *Immunity. 1*:661-673.
Baum, et al. (1992). *Proc. Natl. Acad. Sci. USA. 89*: 2804-2808.
Osawa, et al. (1996). *Science. 273*: 242-245.
Zon, et al. (1995). *Blood. 86*(8): 2876-2891.
Petersen, et al. (1999). *Science. 284*: 1168-1170.
Brazelton, et al. (2000). *Science. 290*: 1775-1779.
Mezey, et al. (2000). *Science. 290*: 1779-1782.
Lagasse, et al. (2000). *Nature Medicine. 6*(11): 1229-1234.
Krause, et al. (2001). *Cell. 105*: 369-377.
Morrison, et al. (1997). *Development. 124*:1929-1939.
Weissmann. (2000). *Science. 287*: 1442-1446.
Miller, et al. (1997). *Proc. Natl. Acad. Sci. USA. 94*: 13648-13653.
Peled, et al. (2002). *British Journal of Hematology. 116*: 655-661.
Puccetti, et al. (2002). *Cancer Research. 62*: 7050-7058.
Grenda, et al. (2002). *Blood. 100*(9):3221-3228.
Ferbeyre. (2002). *Leukemia. 16*:1918-1926.
Cote, et al. (2002). *Blood. 100*(7): 2586-2596.
Petti, et al. (2002). *Blood. 100*(3): 1065-1067.
Mueller, et al. (2002). *Blood. 100*(3): 998-1007.
Acsadi et al. "Human Dystrophin Expression in Mdx Mice After Intramuscular Injection of DNA Contructs", Nature, 352: 815-818, 1991.
Armentano et al. "Expression of Human Factor IX in Rabbit Hepatocytes by Retrovirus-Mediated Gene Transfer: Potential for Gene Therapy of Hemophilia B", Proc. Natl. Acad. Sci. USA, 87: 6141-6145, 1990.
Bae et al. "Copper Uptake and Intracellular Distribution During Retinic Acid-Induced Differentiation of HL-60 Cells", J. Nutr. Biochem., Food Science and Human Nutrition Department, 5: 457-461, 1994.
Bae et al. "Retinoic Acid-Induced HL-60 Cell Differentiation Is Augmented by Copper Supplementation", American Inst. of Nutrition, Food Science and Human Nutrition Department, 123:997-1002, 1993.
Belovari et al. "Differentiation of Rat Neural Tissue in A Serum-Free Embryo Culture Model Followed by In Vivo Transplantation", Croation Medical Journal, 42(6): 611-617, 2001. Abstract.
Berardi et al. "Individual CD34+CD38lowCD19-CD10- Progenitor Cells From Human Cord Blood Generate B Lymphocytes and Granulocytes", Blood, 89(10): 3554-3564, 1997.
Berkner "Development of Adenovirus Vectors for the Expression of Heterologous Genes", BioTechniques, 6(7): 616-629, 1988.
Bhatia et al. "Purification of Primitive Human Hematopoietic Cells Capable of Repopulating Immune-Deficient Mice", Proc. Natl. Acad. Sci. USA, 94: 5320-5325, 1997.
Bi et al. "Effect of Lactoferrin on Proliferation and Differentiation of the Jurkat Human Lymphoblastic T Cell Line", Arch. Immunol. Ther. Exp., 45(4): 315-320, 1997. Abstract.
Bird et al. "Single-Chain Antigen-Binding Proteins", Science, 242: 423-426, 1988.
Boerner et al. "Production of Antigen-Specific Human Monoclonal Antibodies From In Vitro-Primed Human Splenocytes", The Journal of Immunology, 147(1): 86-95, 1991.
Borthwick et al. "A Comparison of Cupruretic Responses to Various Tetramines and D-Penicillamine", Journal of Laboratory and Clinical Medicine, 95(4): 575-580, 1980. Discussion, Table 1.
Brandt et al. "Ex Vivo Expansion of Autologous Bone Marrow CD34+ Cells With Porcine Microvascular Endothelial Cells Results in A Graft Capable of Rescuing Lethally Irradiated Baboons", Blood, 94(1): 106-113, 1999.
Briddell et al. "Purification of CD34+ Cells Is Essential for Optimal Ex Vivo Expansion of Umbilical Cord Blood Cells", Journal of Hematotherapy, 6: 145-150, 1997.

Brigham et al. "Rapid Communication: In Vivo Transfection of Murine Lungs With A Functioning Prokaryotic Gene Using A Liposome Vehicle", The American Journal of the Medical Sciences, 298(4): 278-281, 1989.
Brugger et al. "Ex Vivo Expansion of Enriched Peripheral Blood CD34+ Progenitor Cells by Stem Cell Factor, Interleukin-1β (IL-1β), IL-6, IL-3, Interferon-γ, and Erythropoietin", Blood, 81(10); 2579-2584, 1993.
Brugnera et al. "Cloning, Chromosomal Mapping and Characterization of the Human Metal-Regulatory Transcription Factor MTF-1", Nucleic Acids Research, 22(15): 3167-3173, 1994.
Buskin et al. "Identification of A Myocyte Nuclear Factor That Binds to the Muscle-Specific Enhancer of the Mouse Muscle Creatine Kinase Gene", Molecular and Cellular Biology, 9(6): 2627-2640, 1989.
Cable et al. "Exposure of Primary Rat Hepatocytes in Long-Term DMSO Culture to Selected Transition Metals Induces Hepatocyte Proliferation and Formation of Duct-Like Structure", Hematology, 26(6): 1444-1457, 1997.
Cakir-Kiefer et al. "Kinetic Competence of the cADP-Ribose-CD38 Complex as An Intermediate in the CD38/NAD+ Glycohydrolase-Catalysed Reactions: Implication for CD38 Signalling", Biochemical Journal, 358: 399-405, 2001.
Casal et al. "In Utero Transplantation of Fetal Liver Cells in the Mucopolysaccharidosis Type VII Mouse Results in Low-Level Chimerism, But Overexpression of Beta-Glucuronidase Can Delay Onset of Clinical Signs", Blood, 97(6): 1625-1634, 2001.
Cepko "Overview of the Retrovirus Transduction System", Short Protocols in Molecular Biology, Unit 9.10-9.14: 9-41-9-57, 1984.
ChemMasters "Duraguard 100", Safety Data Sheet, p. 1-4, 1999.
Chen et al. "Fibroblast Growth Factor (FGF) Signaling Through PI 3-Kinase and Akt/PKB Is Required for Embryoid Body Differentiation", Oncogene, 19: 3750-3756, 2000.
Chen et al. "Therapeutic Benefit of Intravenous Administration of Bone Marrow Stromal Cells After Cerebral Ischemia in Rats", Stroke, 32(4): 1005-1011, 2001.
Chisi et al. "Inhibitory Action of the Peptide AcSDKP on the Proliferative State of Hematopoietic Stem Cells in the Presence of Captopril But Not Lisinopril", Stem Cells, 15(6): 455-460, 1997.
Chowdhury et al. "Long-Term Improvement of Hypercholesterolemia After Ex Vivo Gene Therapy in LDLR-Deficient Rabbits", Science, 254: 1802-1805, 1991.
Cicuttini et al. "Support of Human Cord Blood Progenitor Cells on Human Stromal Cell Lines Transformed by SV40 Large T Antigen Under the Influence of An Inducible (Metallothionein) Promoter", Blood, 80(1): 102-112, 1992. p. 104, col. 2, "Coculture of CD34 + Cells", Abstract, p. 104, 1-h Col., last §, r-h Col., § 2, p. 107, 1-h Col., § 2, p. 110, 1-h Col., last §, r-h Col., §1. // EP/OA of 25.4.03 in 20816.
Colter et al. "CD34+ Progenitor Cell Selection: Clinical Transplantation, Tumor Cell Purging, Gene Therapy, Ex Vivo Expansion, and Cord Blood Processing", Journal of Hematology, 5: 179-184, 1996.
Cristiano et al. "Hepatic Gene Therapy: Adenovirus Enhancement of Receptor-Mediated Gene Delivery and Expression in Primary Hepatocytes", Proc. Natl. Acad. Sci. USA, 90: 2122-2126, 1993.
Curiel et al. "Adenovirus Enhancement of Transferrin-Polylysine-Mediated Gene Delivery", Proc. Natl. Acad. Sci. USA, 88: 8850-8854, 1991.
Dabeva et al. "Transcription Factor and Liver-Specific mRNA Expression in Facultative Epithelial Progenitor Cells of Liver and Pancreas", American Journal of Pathology, 147: 1633-1648, 1995. Abstract.
Dahl et al. "Tranformation of Hematopoietic Cells by the Ski Oncoprotein Involves Repression of Retinoic Acid Receptor Signaling", Proc. Natl. Acad. Sci. USA, 95(19): 11187-11192, 1998.
Dai et al. "Gene Therapy Via Primary Myoblasts: Long-Term Expression of Factor IX Protein Following Transplantation In Vivo", Proc. Natl. Acad. Sci. USA, 89: 10892-10895, 1992.
Dalyot et al. "Adult and Neonatal Patterns of Human Globin Gene Expressioon Are Recapitulated in Liquid Cultures", Experimental Hematology, 20: 1141-1145, 1992. Abstract.

Danos et al. "Safe and Efficient Generation of Recombinant Retroviruses With Amphotropic and Ecotropic Host Ranges", Proc. Natl. Acad. Sci. USA, 85: 6460-6464, 1988.

Datta et al. "Ionizing Radiation Activates Transcription of the EGRI Gene Via CArG Elements", Proc. Natl. Acad. Sci. USA, 89: 10149-10153, 1992.

De Bruyn et al. "Comparison of the Coexpression of CD33 and HLA-DR Antigens on CD34+ Purified Cells From Human Cord Blood and Bone Narrow", Stem Cells, 13: 281-288, 1995.

De Luca et al. "Retinoic Acid Is A Potent Regulator of Growth Plate Chondrogenesis", Endocrinology, 141(1): 346-353, 2000. Abstract.

De Wynter et al. "CD34+AC133+ Cells Isolated From Cord Blood Are Highly Enriched in Long-Term Culture-Initiating Cells, NOD/SCID-Repopulating Cells and Dendritic Cell Progenitors", Stem Cells, 16: 387-396, 1998.

Defacque et al. "Expression of Retinoid X Receptor Alpha Is Increased Upon Monocytic Cell Differentiation", Biochemical and Biophysical Research Communications, 220: 315-322, 1996.

Dexter et al. "Conditions Controlling the Proliferation of Haemopoietic Stem Cells In Vitro", Journal of Cell Physiology, 91: 335-344, 1976.

Dubois et al. "Treatment of Wilson's Disease With Trietylene Tetramine Hydrochloride (Trientine)", J. Pediatr. Gastroenterol. Nutr., 10(1): 77-81, 1990. Abstract.

Ebner et al. "Distinct Roles for PI3K in Proliferation and Survival of Oligodendrocyte Progenitor Cells", Journal of Neuroscience Research, 62: 336-345, 2000. p. 338-344.

Eglitis et al. "Gene Expression in Mice After High Efficiency Retroviral-Mediated Gene Transfer", Science, 230: 1395-1398, 1985.

Englisch et al. "Chemcially Modified Oligonucleotides as Probes and Inhibitors", Angewandte Chemie (International Edition in English), 30(6): 613-629, 1991.

Feldman "Israeli Start-Up Gamida-Cell To Receive Prize", Globes—Online, 2004.

Ferry et al. "Retroviral-Mediated Gene Transfer Into Hepatocytes In Vivo", Proc. Natl. Acad. Sci. USA, 88: 8377-8381, 1991.

Fibach et al. "Proliferation and Maturation of Human Erythroid Progenitors in Liquid Culture", Blood, 73(1): 100-103, 1989. Abstract.

Fibach et al. "Retinoic Acid Antagonist Inhibits CD38 antigen Expression on Human Hematopoietic Cells", Blood, 100(11): 172A & 44th Annual Meeting of the American Society of Hematology, 2002. Abstract.

Fibach et al. "The Two-Step Liquid Culture: A Novel Procedure for Studying Maturation of Human Normal and Pathological Erythroid Precursors", Stem Cells, 11(Suppl.1): 36-41, 1993. Abstract.

Filvaroff et al. "Functional Evidence for An Extracellular Calcium Receptor Mechanism Triggering Tyrosine Kinase Activation Associated With Mouse Keratinocyte Differentiation", The Journal of Biological Chemistry, 269(34): 21735-21740, 1994.

Fishwild et al. "High-Avidity Human IgGκ Monoclonal Antibodies From A Novel Strain on Minilocus Transgenic Mice", Nature Biotechnology, 14: 845-851, 1996.

Flores et al. "Akt-Mediated Survival of Oligodendrocytes Induced by Neuregulins", The Journal of Neuroscience, 20(20): 7622-7630, 2000. p. 7624-7629.

Flotte et al. "Expression of the Cystic Fibrosis Transmembrane Conductance Regulators From A Novel Adeno-Associated Virus Promoter", The Journal of Biological Chemistry, 268(5): 3781-3790, 1993.

Flotte et al. "Gene Expression From Adeno-Associated Virus Vectors in Airways Epithelial Cells", Amercan Journal of Respiratory Cell and Molecular Biology, 7: 349-356, 1992.

Fosmire "Zinc Toxicity", American Journal of Clinical Nutrition, 51(2): 225-227, 1990. Abstract.

Freshney "Culture of Animal Cells, A Manual of Basic Technique", John Wiley & Sons, 3rd Ed., Chap.20: 309-311, 327-328.

Gagnon et al. "Activation of Protein Kinase B and Induction of Adipogenesis by Insulin in 3T3-L1 Preadipocytes", Diabetes, 48: 691-698, 1999. p. 693-697.

Gould-Fogerite et al. "Chimerasome-Mediated Gene Transfer In Vitro and In Vivo", Gene, 84: 429-438, 1989.

Grande et al. "Physiological Levels of 1Alpha, 25 Dihydroxyvitamin D3 Induce the Monocytic Commitment of CD34+ Hematopoietic Progenitors", J. Leukoc. Biol., 71(4): 641-651, 2002.

Gur et al. "Toelrance Induction by Megadose Hematopoietic Progenitor Cells: Expansion of Veto Cells by Short-Term Culture of Purified Human CD34+ Cells", Blood, 99: 4174-4181, 2002.

Haj-Ahmad et al. "Development of A Helper-Independent Human Adenovirus Vector and Its Use in the Transfer of the Herpes Simplex Virus Thymidine Kinase Gene", Journal of Virology, 57(1): 267-274, 1986.

Hamilton "Stem Cell Technology to Treat Leukemia Patients Show Promise", The Wall Street Journal, ONLINE, 2003.

Hammond et al. "Suppression of In Vitro Granulocytopoiesis by Captopril and Penicillamine", Experimental Hematology, 16(8): 674-680, 1988.

Hatayama et al. "Regulation of HSP70 Synthesis Induced by Cupric Sulfate and Zinc Sulfate in Thermotolerant HeLa Cells", Journal of Biochemistry, Tokyo, 114(4): 592-597, 1993. Abstract.

Haylock et al. "Ex-Vivo Expansion and Maturation of Peripheral Blood CD34+ Cells Into the Myeloid Lineage", Blood, 80(6): 1405-1412, 1992.

Hermonat et al. "Use of Adeno-Associated Virus as A Mammalian DNA Cloning Vector: Transduction of Neomycin Resistance Into Mammalian Tissue Culture Cells", Proc. Natl. Acad. Sci. USA, 81: 6466-6470, 1984.

Herz et al. "Adenovirus-Mediated Transfer of Low Density Lipoprotein Receptor Gene Acutely Accelerates Cholesterol Clearance in Normal Mice", Proc. Natl. Acad. Sci. USA, 90: 2812-2816, 1993.

Heuchel et al. "The Transcription Factor MTF-1 Is Essential for Basal and Heavy Metal-Induced Metallothionein Gene Expression", The EMBO Journal, 13(12): 2870-2875, 1994.

Hida et al. "Existence of Retinoic Acid-Receptor-Independent Retinoid X-Receptor-Dependent Pathway in Myeloid Cell Function", Jpn. J. Pharmacol., 85(1): 60-69, 2001.

Hirase et al. "Anemia and Neutropenia in A Case of Copper Deficiency: Role of Copper in Normal in Hematopiesis", Acta Haematol., 87: 195-197, 1992.

Hirose et al. "Identification of A Transposon-Related RNA Down-Regulated by Retinoic Acid in Embryonal Carcinoma and Embryonic Stem Cells", Exp. Cell Res., 221(2): 294-300, 1995. Abstract.

Hmama et al. "1-Alpha, 25-Dihydroxyvitamin D3-Induced Myeloid Cell Differentiation Is Regulated by A Vitamin D Receptor-Phospatidylinositol 3-Kinase Signaling Complex", Journal of Experimental Medicine, 190(11): 1583-1594, 1999.

Holleman "Triethylene Tetramine, CAS No. 112-24-3", Chemical Hazard Information Profile Draft Report, 1982. abstract.

Hoogenboom et al. "By-Passing Immunization. Human Antibodies From Synthetic Repertoires of Germline $V_H$ Gene Segments Rearranged In Vitro", Journal of Molecular Biology, 227: 381-388, 1992.

Hottinger et al. "The Copper Chelator D-Penicillamine Delays Onset of Disease A Extends Survival in A Transgenic Mouse Model of Familial Amyotrophic Lateral Sclerosis", European Journal of Neuroscience, 9(7): 1548-1551, 1997. Abstract.

Huang et al. "Differentiation of Human U937 Promonocytic Cells Is Impaired by Moderate Copper Deficiency", Experimental Biology and Medicine, 226(3): 222-228, 2001.

Huber et al. "Retroviral-Mediated Gene Therapy for the Treatment of Hepatocellular Carcinoma: An Innovative Approach for Cancer Therapy", Proc. Natl. Acad. Sci. USA, 88: 8039-8043, 1991.

Hutvágner et al. "RNAi: Nature Abhors A Double-Strand", Current Opinion in Genetics & Development, 12: 225-232, 2002.

Hwu et al. "Functional and Molecular Characterization of Tumor-Infiltrating Lymphocytes Transduced With Tumor Necrosis Factor-α cDNA for the Gene Therapy of Cancer in Humans", The Journal of Immunology, 150(9): 4104-4115, 1993.

Inbar et al. "Localization of Antibody-Combining Sites Within the Variable Portions of Heavy and Light Chains", Proc. Natl. Acad. Sci. USA, 69(9): 2659-2662, 1972.

Itoh et al. "Inhibition of Urokinase Receptor (uPAR) Expression by RNA-Cleaving Catalytic DNA (DNAzyme) Containing Antisense uPAR", Molecular Therapy, 5(5/Part 2): S134, 2002.

Jiang et al. "Phosphatidylinositol 3-Kinase Signaling Mediates Angiogenesis and Expression of Vascular Endothelial Growth Factor in Endothelial Cells", PNAS, 97(4): 1749-1752, 2000.

Johnson et al. "Synthesis and Biological Activity of High-Affinity Retinoic Acid Receptor Antagonists", Bioorganic & Medicinal Chemistry, 7(7): 1321-1338, 1999.

Johnson et al. "The Cytokines IL-3 and GM-CSF Regulate the Transcriptional Activity of Retinoic Acid Receptors in Different In Vitro Models of Myeloid Differentiation", Blood, 99(3): 746-753, 2002.

Jones et al. "Replacing the Complementarity-Determining Regions in A Human Antibody With Those From A Mouse", Nature, 321: 522-525, 1986.

Kang et al. "Retinoic Acid and Its Receptors Repress the Expression and Transactivation Functions of Nur77: A Possible Mechanism for the Inhibition of Apoptosis by Retinoic Acid", Experimental Cell Research, 256: 545-553, 2000.

Kastner et al. "Positive and Negative Regulation of Granulopoiesis by Endogenous RARalpha", Blood, 97(5): 1314-1320, 2001. Abstract.

Kaufman et al. "Translational Efficency of Polycistronic mRNAs and Their Utilization to Express Heterologous Genes in Mammalian Cells", The EMBO Journal, 6(1): 187-193, 1987.

Kawa et al. "Stem Cell Factor and/or Endothelin-3 Dependent Immortal Melanoblast and Melanocyte Populations Derived From Mouse Neural Crest Cells", Pigment Cell Research, 13(Suppl.8): 73-80, 2000.

Kay et al. "Hepatic Gene Therapy: Persistent Expression of Human α1-Antitrypsin in Mice After Direct Gene Delivery In Vivo", Human Gene Therapy, 3: 641-647, 1992.

Khachigian "DNAzymes: Cutting A Path to A New Class of Therapeutics", Current Opinion in Molecular Therapeutics, 4(2): 119-121, 2002.

Kim "Differentiation and Identification of the Two Catalytic Metal Binding Sites in Bovine Lens Leucine Aminopeptidase by X-Ray Crystallography", Proc. Natl. Acad. Sci. USA, 90(11): 5006-5010, 1993.

Kishimoto et al. "Molecular Mechanism of Human CD38 Gene Expression by Retinoic acid. Identification of Retinoic Acid Response Elemen in the First Intron", J. Biol. Chem., 273(25): 15429-15434, 1998. Abstract.

Kizaki et al. Regulation of Manganese Superoxide Dismutase and Other Antioxidant Genes in Normal and Leukemic Hematopoietic Cells and Their Relationship to Cytotoxicity by Tumor Necrosis Factor, Blood, 82(4): 1142-1150, 1993.

Köhler et al. "Defining Optimum Conditions for the Ex Vivo Expansion of Human Umbilical Cord Blood Cells. Influences of Progenitor Enrichment, Interference With Feeder Layers, Early-Acting Cytokines and Agitation of Culture Vessels", Stem Cells, 17(1): 19-24, 1999.

Kohroki et al. "Induction of Differentiation and Apoptosis by Dithizone in Human Myeloid Leukemia Cell Lines", Leukemia Research, 22(5): 405-412, 1998. Discussion.

Koizumi et al. "Large Scale Purification of Human Blood CD34+ Cells From Cryopreserved Peripheral Blood Stem Cells, Using A Nylon-Fiber Syringe System and Immunomagnetic Microspheres", Bone Marrow Transplantation, 26: 787-793, 2000.

Lange et al. "Biological and Clinical Advances in Stem Cell Expansion", Leukemia, 10: 943-945, 1996.

Larrick et al. "PCR Amplification of Antibody Genes", Methods: A Companion to Methods in Enzymology, 2(2): 106-110, 1991.

Lassila et al. "Role for Lys-His-Gly-NH2 in Avian and Murin B Cell Development", Cellular Immunology, 122(2): 319-328, 1989. Figs.

Lau et al. "A Peptide Molecule Mimicking the Copper (II) Transport Site of Human Serum Albumin", Journal of Biological Chemistry, 249(16): 5878-5884, 1974. Discussion.

Lawlor et al. "Coordinate Control of Muscle Cell Survival by Distinct Insulin-Like Growth Factor Activated Signaling Pathways", The Journal of Cell Biology, 151(6): 1131-1140, 2000. p. 1133-1139.

Lee et al. "Effect of Vitamin D Analog, EB1089, on Hematopoietic Stem Cells From Normal and Myeloid Leukemic Blasts", Leukemia, 10: 1751-1757, 1996.

Lemarchand et al. "Adenovirus-Mediated Transfer of A Recombinant Human α1-Antitrypsin cDNA to Human Endothelial Cells", Proc. Natl. Acad. Sci. USA, 89: 6482-6486, 1992.

Leslie et al. "An Activating Mutation in the Kit Receptor Abolishes the Stroma Requirement for Growth of ELM Erythroleukemia Cells, But Does Not Prevent Their Differentiation in Response to Erythropoietin", Blood, 92(12): 4798-4807, 1998.

Lewandowski et al. "Phosphatidylinositol 3-Kinases Are Involved in the All-Trans Retinoic Acid-Induced Upregulation of CD38 Antigen of Human Haematopoietic Cells", British Journal of Hematology, 118(2): 535-544, 2002. Fig.8.

Li et al. "Activation of Phosphatidylinositol-3 Kinase (PI-3K) and Extracellular Regulated Kinases (Erk1/2) Is Involved in Muscarinic Receptor-Mediated DNA Synthesis in Neural Progenitor Cells", The Journal of Neuroscience, 21(5): 1569-1579, 2001. p. 1572-1578.

Lonberg et al. "Antigen-Specific Human Antibodies From Mice Comprising Four Distinct Genetic Modifications", Nature, 368: 856-859, 1994.

Lonberg et al. "Human Antibodies From Transgenic Mice", International Review in Immunology, 13: 65-93, 1995.

Lutton et al. "Zinc Porphyrins: Potent Inhibitors of Hematopoieses in Animal and Human Bone Marrow", Proc. Natl. Acad. Sci. USA, 94: 1432-1436, 1997.

Mader et al. "A Steroid-Inducible Promoter for the Controlled Overexpression of Cloned Genes in Eukaryotic Cells", Proc. Natl. Acad. Sci. USA, 90: 5603-5607, 1993.

Manome et al. "Coinduction of C-Jun Gene Expression and Internucleosomal DNA Fragmentation by Ionizing Radiation", Biochemistry, 32: 10607-10613, 1993.

Mar et al. "A Conserved CATTCCT Motif Is Required for Skeletal Muscle-Specific Activity of the Cardiac Troponin T Gene Promoter", Proc. Natl. Acad. Sci. USA, 85: 6404-6408, 1988.

Marks et al. "By-Passing Immunization. Human Antibodies From V-Gene Libraries Displayed on Phage", Journal of Molecular biology, 222: 584-597, 1991.

Marks et al. "By-Passing Immunization: Building High Affinity Human Antibodies by Chain Shuffling", Bio/Technology, 10: 779-783, 1992.

Martelli et al. "Transplants Across Human Leukocyte Antigen Barriers", Seminars in Hematology, 39(1): 48-56, 2002.

Matzner et al. "Bone Marrow Stem Cell Gene Therapy of Arylsulfatase A-Deficient Mice, Using An Arylsulfatase A Mutant That Is Hypersecreted From Retrovirally Transduced Donor-Type Cells", Human Gene Therapy, 12: 1021-1033, 2001.

McLaughlin et al. "Adeno-Associated Virus General Transduction Vectors: Analysis of Proviral Structures", Journal of Virology, 62(6): 1963-1973, 1988.

McNiece et al. "Action of Interleukin-3, G-CSF on Highly Enriched Human Hematopoietic Preogenitor Cells: Synergistic Interaction of GM-CSF Plus G-CSF", Blood, 74: 110-114, 1989.

McNiece et al. "CD34+ Cell Selection From Frozen Cord Blood Products Using the Isolex 300i and CliniMACS CD34 Selection Devices", Journal of Hematotherapy, 7: 457-461, 1998.

Mehta et al. "Involvement of Retinoic Acid Receptor-α-Mediated Signaling Pathway in Induction of CD38 Cell-Surface Antigen", Blood, 89(10): 3607-3614, 1997. Abstract.

Mehta et al. "Retinoid-Mediated Signaling Pathways in CD38 Antigen Expression in Myeloid Leukemia Cells", Leukemia and Lymphoma, 32(5/6): 441-449, 1999.

Merck & Co. "The Merck Index, An Encyclopedia of Chemicals, Drugs and Biologicals", 10th Ed.(3742): 549, 1983.

Migliaccio et al. "Long-Term Generation of Colony-Forming Cells in Liquid Culture of CD34+ Cord Blood Cells in the Presence of Recombinant Human Stem Cell Factor", Blood, 79: 2620-2627, 1992.

Miller "Progress Toward Human Gene Therapy", Blood, The Journal of the American Society of Hematology, 76(2): 271-278, 1990.

Mills et al. "Regulation of Retinoid-Induced Differentiation in Embryonal Carcinoma PCC4.Aza 1 R Cells: Effects of Retinoid-Receptor Selective Ligands", Cell Growth Differ., 7(3): 327-337, 1996. Abstract.

Moore et al. "Ex Vivo Expansion of Cord Blood-Devined Stem Cells and Progenitons", Blood Cells, 20: 468-481, 1994.

Morier Teissier et al. "Synthesis and Antitumor Properties of An Anthraquinone Bisubstituted by the Copper Chelating Peptide Gly-Gly-L-His", Journal of Medical Chemistry, 36: 2084-2090, 1993. Abstract.

Morimoto et al. "EDTA Induces Differentiation and Suppresses Proliferation of Promyelotic Leukemia Cell Line HL-60—Possible Participation of Zinc-", Biochemistry International, 28(2): 313-321, 1992. Abstract, p. 317, § 1.

Morrison "Success in Specification", Nature, 368(6474): 812-813, 1994.

Mueller et al. "Heterozygous PU.1 Mutations are Associated with Acute Myeloid Leukemia", Blood, 100(30:998-1007, 2002.

Muench et al. "Interactions Among Colony-Stimulating Factors, IL-1β, IL-6, and Kit-Ligand in the Regulation of Primitive Murine Hematopoietic Cells", Experimental Hematology, 20: 339-349, 1992.

Munshi et al. "Evidence for A Causal Role of CD38 Expression in Granulocytic Differentiation of Human HL-60 Cells", The Journal of Biological Chemistry, 277(51): 49453-49458, 2002.

Muramatsu et al. "Reversible Integration of the Dominant Negative Retinoid Receptor Gene for Ex Vivo Expansion of Hematopoietic Stem/Progenitor Cells", Biochem. Biophys. Res. Commun., 285(4): 891-896, 2001. Abstract.

Murray et al. "Modulation of Murine Lymphocyte and Macrophage Proliferation by Parenteral Zinc", Clin. Exp. Immunol., 53: 744-749, 1983. Abstract, p. 748, § 2-3.

Muzyczka "Use of Adeno-Associated Virus as A General Transduction Vector for Mammalian Cells", Current Topics in Microbiology and Immunology, 158: 97-129, 1992.

Narita et al. "Cardiomycyte Differentiation by GATA-4-Deficient Embryonic Stem Cells", Development, 122(19): 3755-3764, 1996.

Neuberger "Generating High-Avidity Human Mabs in Mice", Nature Biotechnology, 14: 826, 1996.

Nicolau et al. "Liposomes as Carriers for In Vivo Gene Transfer and Expression", Methods in Enzymology, 149(Chap.16): 157-176, 1987.

Okazaki et al. "Characteristics and Partial Purificaiton of A Novel Cytosolic, Magnesium-Independent, Neutral Sphingomyelinase Activated in the Early Signal Transduction of 1α,25-Dihydroxyvitamin D3-Induced HL-60 Cell Differentiation", The Journal of Biological Chemistry, 269(6): 4070-4077, 1994.

Pack et al. "Improved Bivalent Miniantibodies, With Identical Avidity as Whole Antibodies, Produced by High Cell Density Fermentation of *Escherichia Coli*", Bio/Technology, 11: 1271-1277, 1993.

Palmiter "Regulation of Metallothionein Genes by Heavy Metals Appears to Be Mediated by A Zinc-Sensitive Inhibitor That Interacts With A Constitutively Active Transcription Factor, MTF-1", Proc. Natl. Acad. Sci. USA, 91(4): 1219-1223, 1994.

Peled et al. "Cooper Chelators Sustain Long-Term Expansion of Cord-Blood CD 34 + Cultures Initiated With IL-3 and G-CSF—Late Acting, Differentiation-Inducing Cytokines", Blood, 96(1): 773a, Abstract 3343, 2000.

Peled et al. "Identification of A Serum-Derived Differentiation-Inducing Activity as the Copper-Binding Protein Ceruloplasmin", Blood, 92(10, Suppl.1, Part 1-2): 618A-619A, Abstract 2551, 1998.

Peled et al. "Regulation of Long-Term Expansion of Hemopoietic Stem/Progenitor Cells (HPC) by Intracellular Copper Content", Blood, 96(Part 1): 776-777a, 2000.

Pervical "Copper and Immunity", American Journal of Clinical Nutrition, 67(5 Suppl.): 1064S-1068S, 1998. p. 1066, 1-h Col., § 2, r-h Col., § 2. // EP/OA of 12.1.05 in 21437; EP/OA of 20.4.06 in 20816;EP/OA of 20.4.06 in 25695.

Percival "Neutropenia Caused by Copper Deficiency: Possible Mechanism of Action", Nutrition Reviews, 53(3): 59-66, 1995.

Percival et al. "Copper Is Required to Maintain Cu/Zn-Superoxide Dismutase Activity During HL-60 Cell Differentiation", Proc. Soc. Exp. Biol. Med., 203: 78-83, 1993.

Percival et al. "HL-60 Cells Can Be Made Copper Deficient by Incubating With Tetraethylenepentamine 1,2,3", Journal of Nutrition, 122(12): 2424-2429, 1992. // Abstract, p. 2424, r-h Col., p. 2425, 1-h Col., § 2, p. 2426, 1-h Col., last §, p. 2428, r-h Col., last §.. JP/OA of 9.3.05 in 21442; IDS in 26691; EP/OA of 26.9.05 in 21437; EP/OA of 28.9.05 in 20816/20.4.06 in 20816/25.04.03 in 20816; IDS (not by us) in 20819; EP/OA of 20.4.06 in 20816;EP/OA of 20.4.06 in 25695.

Perrotti et al. "Overexpression of the Zinc Finger Protein MZF1 Inhibits Hematopoietic Development From Embryonic Stem Cells: Correlation With Negative Regulation of CD34 and C-MYB Promoter Activity", Mol. Cell. Biol., 15(11): 6075-6087, 1995. Abstract; p. 6076, 1-h Col., § 4, p. 6080, r-h Col., last §—p. 6085, r-h Col., first §.

Petersen et al. "Hepatic Oval Cells Express the Hematopoietic Stem Cell Marker Thy-1 in the Rat", Hepatology, 27(2): 433-445, 1998.

Piacibello et al. "Extensive Amplification and Self-Renewal of Human Primitive Hematopoietic Stem Cells From Cord Blood", Blood, 89(8): 2644-2653, 1997.

Pickart et al. "Growth Modulating Plasma Tripeptide May Function by Facilitating Copper Uptake Into Cells", Nature, 288(18/25): 715-717, 1980. Abstract. p. 716, col. 2, Line1.

Podestà et al. Extracellular Cyclic ADP-Ribose Increases Intracellular Free Calcium Concentration and Stimulates Proliferation of Human Hematopoietic Progenitors, FASEB Journal, 14(5): 680-690, 2000. Fig. 1.

Porter "The Hydrolysis of Rabbit γ-Globulin and Antibodies With Crystalline Papain", Biochemical Journal 73: 119-126, 1959.

Presta "Antibody Engineering", Current Opinion in Structural Biology, 2: 593-596, 1992.

Punzel et al. "The Type of Stromal Feeder Used in Limiting Dilution Assays Influences Frequency and Maintenance Assessment of human Long-Term Culture Initiating Cells", Leukemia, 13: 92-97, 1999.

Purdy et al. "Large Volume Ex Vivo Expansion of CD34+-Positive Hematopoietic Progenitor Cells for Transplantation", Journal of Hematotherapy, 4: 515-525, 1995.

Purton et al. "All-Trans Retinoic Acid Enhances the Long-Term Repopulating Activity of Cultured Hematopoietic Stem Cells", Blood, 95(2): 470-477, 2000. Abstract.

Purton et al. "All-Trans Retinoic Acid Facilities Oncoretrovirus-Mediated Transduction of Hematopoietic Repopulating Stem Cells", J. Hematother. Stem Cell Res., 10(6): 815-825, 2001. Abstract.

Quantin et al. "Adenovirus as An Expression Vector in Muscle Cells In Vivo", Proc. Natl. Acad. Sci. USA, 89: 2581-2584, 1992.

Ratajczak et al. "Effect of Basic (FGF-2) and Acidic (FGF-1) Fibroblast Growth Factors on Early Haemopoietic Cell Development", British Journal of Hematology, 93: 772-782, 1996.

Reeves et al. "High Zinc Concentrations in Culture Media Affect Copper Uptake and Transport in Differentiated Human Colon Adenocarcinoma Cells", Journal of Nutrition, 126(6): 1701-1712, 1996. Abstract.

Reid et al. "Interactions of Tumor Necrosis Factor With Granulocyte-Macrophage Colony-Stimulating Factor and Other Cytokines in the Regulation of Dendritic Cell Growth In Vitro From Early Bipotent CD34+ Progenitors in Human Bone Marrow", Journal of Immunology, 149(8): 2681-2688, 1992. Abstract. p. 2686, col. 1, 2nd §, p. 2682, col. 1, 2nd §.

Riechmann et al. "Reshaping Human Antibodies for Therapy", Nature, 332: 323-327, 1988.

Rosenfeld et al. "Adenovirus-Mediated Transfer of A Recombinant α1-Antitrypsin Gene to the Lung Epithelium In Vivo", Science, 252: 431-434, 1991.

Rosenfeld et al. "In Vivo Transfer of the Human Cystic Fibrosis Transmembrane Conductance Regulator Gene to the Airway Epithelium", Cell, 68: 143-155, 1992.

Rowley et al. "Isolation of CD34+ Cells From Blood Stem Cell Components Using the Baxter Isolex System", Bone Marrow Transplantation, 21: 1253-1262, 1998.

Rusten et al. "The RAR-RXR as Well as the RXR—RXR Pathway Is Involved Signaling Growth Inhibition of Human CD34+ Erythroid Progenitor Cells", Blood, 87(5): 1728-1736, 1996. Abstract.

Sammons et al. "Mechanisms Mediating the Inhibitory Effect of All-Trans Retinoic Acid on Primitive Hematopoietic Stem Cells in Human Long-Term Bone Marrow Culture", Stem Cells, 18(3): 214-219, 2000.

Samulski et al. "Helper-Free Stocks of Recombinant Adeno-Associated Viruses: Normal Integration Does Not Require Viral Gene Expression", Journal of Virology, 63(9): 3822-3828, 1989.

Sato et al. "In Vitro Expansion of Human Peripheral Blood CD34+ Cells", Blood, 82(12): 3600-3609, 1993.

Sauve et al. "Mechanism-Based Inhibitors of CD38: A Mammalian Cyclic ADP-Ribose Synthetase", Biochemistry, 41(26): 8455-8463, 2002.

Schmetzer et al. "Effect of GM-CSF, 1,25-Dihydroxycholecalciferol (Vit. D) and All-Trans-Retinocin Acid (ATRA) on the Proliferation and Differentiation of MDS-Bone Marrow (BM)-Cells In Vitro", Hematology, 2: 11-19, 1997.

Schwartz et al. "In Vitro Myelopoiesis Stimulated by Rapid Medium Exchange and Supplementation With Hematopoietic Growth Factors", Blood, 78(12): 3155-3161, 1991.

Seed "An LFA-3 cDNA Encodes A Phospholipid-Linked Membrane Protein Homologous to Its Receptor CD2", Nature, 329: 840-842, 1987.

Sekhar et al. "Retroviral Transduction of CD34-Enriched Hematopoietic Progenitor Cells Under Serum-Free Conditions", Human Gene Therapy, 7: 33-38, 1996.

Selden "Transfection Using DEAE-Dextran", Short Protocols in Molecular Biology, Unit 9.2: 9-9-9-11, 1984.

Selden et al. "Optimization of Transfection", Short Protocols in Molecular Biology, Unit 9.4: 262-263, 1984.

Sergeant et al. "Iron and Copper Requirements for Proliferation and Differentiation of A Human Promyelocytic Leukemia Cell Line (HL-60)", Journal of Cellular Physiology, 163(3): 477-485, 1995.

Shimakura et al. "Murine Stromal Cell Line HESS-5 Maintains Reconstituting Ability of Ex Vivo-Generated Hematopoietic Stem Cells From Human Bone Marrow and Cytokine-Mobilized Peripheral Blood", Stem Cells, 18: 183-189, 2000.

Shimizu et al. "Treatment and Management of Wilson's Disease", Pediatr. Int., 41(4): 419-422, 1999. Abstract.

Sigurdsson et al. "Copper Chelation Delays the Onset of Prion Disease", J. Biol. Chem., 278(47): 46199-202, 2003. Abstract.

Simon et al. "Copper Deficiency and Sideroblastic Anemia Associated With Zinc Ingestion", American Journal of Hematology, 28: 181-183, 1988.

Slavin et al. "Donor Lymphocyte Infusion: The Use of Alloreactive and Tumor-Reactive Lymphocytes for Immunotherapy of Malignant and Nonmalignant Disease in Conjunction With Allogeneic Stem Cell Transplantation", Journal of Hematotherapy & Stem Cell Research, 11: 265-276, 2002.

Slavin et al. "Treatment of Leukemia by Alloreactive Lymphocytes and Nonmyeloablative Stem Cell Transplantation", Journal of Clinical Immunology, 22(2): 64-69, 2002.

Spencer et al. "Controlling Signal Transduction With Synthetic Ligands", Science, 262: 1019-1024, 1993.

Suda et al. "A Study of Trientine Therapy in Wilson's Disease With Neurology Symptoms", No To Hattatsu, 25(5): 429-34, 1993. Abstract.

Szilvassy et al. "Differential Homing and Engraftment Properties of Hematopoetic Progenitor Cells From Murine Bone Marrow Mobilized Peripheral Blood Cells and Fetal Liver", Blood, 98(7): 2108-2115, 2001.

Takeshita et al. "Selective Stimulation by Ceramide of the Expression of the α Isoform of Retinoic Acid and Retinoid X Receptors in Osteoblastic Cells", Journal of Biological Chemistry, 275(41): 32220-32226, 2000.

Tashiro-Itoh et al. "Metallothionein Expression and Concentrations of Copper and Zinc Are Associated With Tumor Differentiation in Hepatocellular Carcinoma", Liver, 17: 300-306, 1997.

Todisco et al. "CD38 Ligation Inhibits Normal and Leukemic Myelopoiesis", Blood, 95(2): 535-542, 2000. Abstract.

Tratschin et al. "A Human Parvovirus, Adeno-Associated Virus, as A Eucaryotic Vector: Transient Expression and Encapsidation of the Procaryotic Gene for Chloramphenicol Acetyltransferase", Molecular and Cellular Biology, 4(10): 2072-2081, 1984.

Tratschin et al. "Adeno-Associated Virus Vector for High-Frequency Integration, Expression, and Rescue of Genes in Mammalian Cells", Molecular and Cellular Biology, 5(11): 3251-3260, 1985.

Tratschin et al. "Genetic Analysis of Adeno-Associated Virus: Properties of Deletion Mutants Constructed In Vitro and Evidence for An Adeno-Associated Virus Replication Function", Journal of Virology, 51(3): 611-619, 1984.

Tuba et al. "Synthesis and Structure—Activity Relationships of Neuromuscular Blocking Agents", Current Medicinal Chemistry, 9: 1507-1536, 2002.

Ueno et al. "A Novel Retinoic Acid Receptor (RAR)-Selective Antagonist Inhibits Differentiation and Apoptosis of HL-60 Cells: Implications of RARα-Mediated Signals in Myeloid Leukemic Cells", Leukemia Research, 22(6): 517-525, 1998.

Van Beusechem et al. "Long-Term Expression of human Adenosine Deaminase in Rhesus Monkeys Transplanted With Retrovirus-Infected Bone-Marrow Cells", Proc. Natl. Acad. Sci. USA, 89: 7640-7644, 1992.

Verfaillie "Can Human Hematopoietic Stem Cells Be Cultured Ex Vivo?", Stem Cells, 12(5): 455-476, 1994. Abstract.

Verfaillie "Direct Contact Between Human Primitive Hematopoietic Progenitors and Bone Marrow Stroma Is Not Required for Long-Term In Vitro Hematopoiesis", Blood, 79(11): 2821-2826, 1992.

Verhoeyen et al. "Reshaping Human Antibodies: Grafting An Antilysozyme Activity", Science, 239: 1534-1536, 1988.

Verlinden et al. "Interaction of Two Novel 14-Epivitamin D3 Analogs With Vitamin D3 Receptor-Retinoid X Receptor Heterodimers on Vitamin D3 Response Elements", Journal of Bone and Mineral Research, 16(4): 625-638, 2001.

Vilensky et al. "British Anti-Lewisite (Dimercaprol): an Amazing History", Ann. Emerg. Med., 41(3): 378-83, 2003. Abstract.

Wall et al. "Inhibition of the Intrinsic NAD+ Glycohydrolase Activity of CD38 by Carbocyclic NAD Analogues", Biochemical Journal, 335(3): 631-636, 1998.

Wang et al. "PH-Sensitive Immunoliposomes Mediate Target-Cell-Specific Delivery and Controlled Expression of A Foreign Gene in Mouse", Proc. Natl. Acad. Sci. USA, 84: 7851-7855, 1987.

Wasa et al. "Copper Deficiency With Pancytopenia During Total Parenteral Nutrition", Journal of Parenteral and Enteral Nutrition, 18(2): 190-192, 1994.

Wendling et al. "Retinoid X Receptor Are Essential for Early Mouse Development and Placentogenesis", Proc. Natl. Acad. Sci. USA, 96(2): 547-551, 1999.

Whitlow et al. "Single-Chain Fv Proteins and Their Fusion Proteins", Methods: A Companion to Methods in Enzymology, 2(2): 97-105, 1991.

Wilson et al. "Hepatocyte-Directed Gene Transfer In Vivo Leads to Transient Improvement of Hypercholesterolemia in Low Density Lipoprotein Receptor-Deficient Rabbits", The Journal of Biological Chemistry, 267(2): 963-967, 1992.

Wilson et al. "Retrovirus-Mediated Transduction of Adult Hepatocytes", Proc. Natl. Acad. Sci. USA, 85: 3014-3018, 1988.

Wolff et al. "Direct Gene Transfer Into Mouse Muscle In Vivo", Science, 247: 1465-1468, 1990.

Wondisford et al. "Cloning of the Human Thyrotropin β-Subunit Gene and Transient Expression of Biologically Active Human Thyrotropin After Gene Transfection", Molecular Endocrinology, 2: 32-39, 1988.

Wu et al. "Receptor-Mediated Gene Delivery and Expression In Vivo", The Journal of Biological Chemistry, 263(29): 14621-14624, 1988.

Yin et al. "AC133, A Novel Marker for Human Hematopoietic Stem and Progenitor Cells", Blood, 90(12): 5002-5012, 1997.

Zidar et al. "Observations on the Anemia and Neutropenia of Human Copper Deficiency", American Journal of Hematology, 3: 177-185, 1977.

Zocchi et al. "Ligand-Induced Internalization of CD38 Results in Intracellular Ca2+ Moblization: Role of NAD+ Transport Across Cell Membranes", FASEB J., 13(2): 273-283, 1999. Abstract.

\* cited by examiner

Figure 11

| Cellular copper-percent from control | TEPA-CuCl$_2$ complex |
|---|---|
| 178% | 10µM |
| 235% | 30µM |
| 290% | 60µM |

| | TEPA |
|---|---|
| 80% | 5µM |
| 55% | 10µM |
| 42% | 20µM |

METHODS OF EXPANDING STEM AND PROGENITOR CELLS AND EXPANDED CELL POPULATIONS OBTAINED THEREBY

RELATED APPLICATIONS

This Application is a Continuation of PCT International application PCT/IL03/00062, filed Jan. 23, 2003, which claims the benefit of priority from U.S. Provisional Patent Application No. 60/351,012, filed Jan. 25, 2002.

FIELD AND BACKGROUND OF THE INVENTION

The present invention relates to methods of ex-vivo and in-vivo controlling the proliferation and differentiation of stem and progenitor cells. More specifically, the present invention relates to ex vivo and in vivo methods of promoting proliferation, yet restricting differentiation of stem and progenitor cells by treating the cells with transition metal chelates, copper chelates in particular. In another aspect, the present invention relates to a method of enriching a population of non-differentiated stem or progenitor cells present in a mixed population of cells cultured ex vivo by treating the cells with transition metal chelates or transition metal chelators. In yet another aspect, the present invention relates to ex-vivo expanded populations of stem and progenitor cells obtained by the methods of the present invention.

As used herein throughout, the phrase "transition metal chelator" refers to a transition metal ligand that has at least two atoms capable of coordinating with an indicated metal, so as to form a ring. A transition metal chelator of an indicated transition metal, is free of, i.e., not complexed with, an ion of the indicated transition metal and hence, the phrase "copper chelator", for example, refers to a chelator of copper, which is free of, i.e., not complexed with, a copper ion.

As used herein throughout, the phrase "transition metal chelate" refers to a chelator of an indicated transition metal, as is defined hereinabove, which is complexed with an ion of the indicated transition metal and hence, the phrase "copper chelate", for example, refers to a chelator of copper complexed with a copper ion.

As is well known in the art, one or more molecules are considered as transition metal chelators if the formation of a cyclic complex of the molecule(s) with an ion of the transition metal results in a "chelate effect". The phrase "chelate effect" refers to the enhanced stability of a complexed system containing the chelate, as compared with the stability of a system that is as similar as possible but contains none or fewer rings. The parameters for evaluating the chelate effect of a chelate typically include the enthalpy and entropy changes ($\Delta H$ and $\Delta S$), according the following equation:

$$\Delta G^0 = \Delta H^0 - T\Delta S^0 = -RT \ln \beta$$

where $\beta$ is the equilibrium constant of the chelate formation and hence represents the chelate effect.

Hence, transition metal chelates and copper chelates in particular refer to complexes that include copper ion and one or more copper chelator(s) complexed therewith, which are characterized by a large $\beta$ value. Representative examples of copper chelators include polyamine molecules such as ethylene diamine and cyclam, which form copper chelates with enhanced chelate effect.

Normal production of blood cells (hematopoiesis) and of other cell types involves the processes of proliferation and differentiation which are tightly coupled. In most hematopoietic cells, following cell division, the daughter cells undergo a series of progressive changes that eventually culminate in fully differentiated (mature), functional blood cells, which in most part are devoid of or very restricted in proliferative potential. Similarly, for cells of other, non-hematopoietic origin, following cell division, the daughter cells undergo a series of progressive changes which eventually culminate in fully differentiated (mature) functional tissue, which in most part is composed of cells devoid of or severely restricted in proliferative potential. Thus, the process of differentiation limits, and eventually halts cell division. Only in a small minority of the cells in an organ, known as stem cells, cell division may result in progeny which are similar or identical to their parental cells. This type of cell division, known as self-renewal, is an inherent property of stem cells and helps to maintain a small pool of stem cells in their most undifferentiated state. Some stem cells lose their self-renewal capacity and following cell division differentiate into various types of lineage committed progenitors which finally give rise to mature cells. While the latter provide the functional capacity of the tissue, e.g., the blood cell system, the stem cells are responsible for the maintaining of tissue formation, e.g., hematopoiesis, throughout life, despite a continuous loss of the more differentiated cells through apoptosis (programmed cell death) and/or, e.g., for the blood system, active removal of aging mature cells by the reticuloendothelial system and/or other loses of cell mass. It will be appreciated that in one way or another these processes characterize all cell lineages of multicellular organisms, because replenishment of dead cells occurs during the life cycle of such organisms.

Normal hematopoiesis is coordinated by a variety of regulators which include glycoproteins such as the colony stimulating factors (CSF), as well as small molecules such as the retinoids. They regulate the survival (e.g., by inhibiting apoptosis), proliferation and differentiation of progenitor and precursor cells and the activation state of mature cells.

In acute leukemia, for example, there is a block in cell differentiation. As a result, the leukemic cells maintain their proliferative potential. Leukemic cells do not respond normally to the various regulators [37-42].

Thus, cells obtained from patients with acute myeloid leukemia develop in culture, in response to stimulation by colony stimulating factor (CSF), small colonies of undifferentiated cells, as compared to large colonies of granulocytes and macrophages, which develop following cloning normal hematopoietic cells.

Adult stem cells are typically very rare, whereby for most tissues the number of stem cells is 1 in a 1,000,000 cells. Hence, obtaining a large number of stem cells, especially human adult stem cells directly from a tissue of choice, is impractical.

Therefore, and as is further detailed below, expansion of the stem cell and other defined progenitor cells such as blood stem cells or lympho-hematopoietic progenitor cell subpopulations by ex-vivo culturing could have important clinical applications. Similarly, expansion of non-hematopoietic adult stem cell, such as stem cells isolated from organs such as liver, pancreas, kidney, lung, etc., by ex-vivo culturing could have important clinical applications, especially in view of recent findings showing that adult stem cells are capable of transdifferentiation, i.e., developing into cell lineages different from the lineages characterizing their tissue origin.

A variety of protocols have been suggested and experimented for expansion of such cell populations. The main experimental strategies employed include incubation of mononuclear cells with or without selection of $CD_{34}^+$ [8]; with different cocktails of early and late growth factors [17]; with or without serum [7]; in stationary cultures, rapid medium exchanged cultures [18] or under continuous perfusion (bioreactors) [6]; and with or without established stromal cell layer [19].

Although a significant expansion of intermediate and late progenitors was often obtained during 7-14 days ex-vivo cultures under these conditions, the magnitude of early hematopoietic ($CD_{34}^+$ $CD_{38}^-$) stem cells with high proliferative potential, typically declined [6].

Thus, these cultures clearly do not result in true stem cell expansion, but rather in proliferation and differentiation of the stem cells into pre-progenitor cells, accompanied by depletion of the primitive stem cell pool.

In order to achieve maximal ex-vivo expansion of stem cells, the following conditions should be fulfilled: (i) differentiation should be reversibly inhibited or delayed; and (ii) self-renewal should be maximally prolonged.

For some applications, following cell expansion, it is important to have methods to induce differentiation of the expanded cell population, so as to convert the expanded cell population to mature functional cells or tissue. In other applications, expanded undifferentiated stem cells can be used in their undifferentiated state to augment stem cell deficiency or be used in in vivo transdifferentiation applications.

International Patent Applications Serial Nos. PCT/IL99/00444 and PCT/US99/02664, U.S. patent applications Ser. Nos. 09/986,897 09/988,127, and Peled et al. (Brit. J. Haematol. 116:655, 2002) teach that certain trace-element chelators, copper chelators in particular, can inhibit differentiation of stem and progenitor cells, thereby prolonging cell proliferation and expansion ex-vivo. It is further disclosed that elevation of cellular copper content accelerates stem or progenitor cells differentiation. It was thus postulated that cellular copper is involved in the modulation of stem or progenitor cell self-renewal, proliferation and differentiation, whereas, increasing cellular copper content accelerates differentiation of stem or progenitor cells, while decreasing of cellular copper content inhibits differentiation of stem or progenitor cells.

The mechanisms controlling the rate of self renewal versus differentiation in adult stem cells are not fully understood, nevertheless, as a response to harsh medical treatments, such as chemotherapy and/or radiotherapy, stem cell depletion below an adequate level, results in rapid loss of tissue due to impaired tissue regeneration. Under such circumstances, stem cell transplantation and/or treatment for augmenting in vivo stem cell renewal are advised [43-47].

There is thus an identified need for and it would be advantageous to have ex-vivo and in vivo methods useful in expanding stem and progenitor cells of various cell lineages.

SUMMARY OF THE INVENTION

According to one aspect of the present invention there is provided a method of ex vivo expanding a population of stem and/or progenitor cells, while at the same time reversibly inhibiting differentiation of the stem and/or progenitor cells. The method comprises providing the stem and/or progenitor cells with conditions for cell proliferation and with an effective amount of at least one copper chelate, so as to maintain a free copper concentration available to the cells substantially unchanged, to thereby expand the population of the stem and/or progenitor cells, while at the same time reversibly inhibit differentiation of the stem and/or progenitor cells.

According to another aspect of the present invention there is provided another method of ex vivo expanding a population of stem and/or progenitor cells, while at the same time reversibly inhibiting differentiation of the stem and/or progenitor cells, which comprises providing at least one copper chelate; and thereafter mixing an effective amount of the copper chelate(s) with a cell growth medium, which provides the stem and/or progenitor cells with conditions for cell proliferation, and with the population of stem and/or progenitor cells, so as to keep substantially unchanged by this mixing a free copper concentration in the cell growth medium.

According to yet another aspect of the present invention there is provided a method of hematopoietic cells transplantation. The method comprises obtaining the hematopoietic cells to be transplanted from a donor; providing the hematopoietic cells ex-vivo with conditions for cell proliferation and with an effective amount of at least one copper chelate, so as to maintain a free copper concentration available to the cells substantially unchanged, to thereby expand the population of stem and/or progenitor cells, while at the same time reversibly inhibit differentiation of the stem and/or progenitor cells; and transplanting the hematopoietic cells to a patient.

According to still another aspect of the present invention there is provided another method of hematopoietic cells transplantation, which comprises obtaining hematopoietic cells to be transplanted from a donor; providing at least one copper chelate; and thereafter mixing an effective amount of the copper chelate(s) with a cell growth medium, which provides the hematopoietic cells with conditions for cell proliferation, and with the hematopoietic cells, so as to keep substantially unchanged by this mixing a free copper concentration in the cell growth medium, to thereby expand the hematopoietic cells, while at the same time reversibly inhibit differentiation of the hematopoietic cells; and transplanting the hematopoietic cells to a patient.

According to further features in preferred embodiments of the invention described below, the donor and the patient are a single individual.

According to an additional aspect of the present invention there is provided a method of genetically modifying stem cells with an exogene. The method comprises obtaining stem cells to be genetically modified; providing the stem cells ex-vivo with conditions for cell proliferation and, at the same time, administering the stem cells with an effective amount of at least one copper chelate, so as to maintain a free copper concentration available to the cells substantially unchanged, to thereby expand the population of the stem cells, while at the same time reversibly inhibit differentiation of the stem cells; and genetically modifying the stem cells with the exogene.

According to yet an additional aspect of the present invention there is provided another method of genetically modifying stem cells with an exogene, which comprises obtaining stem cells to be genetically modified; providing at least one copper chelate; and thereafter mixing an effective amount of the copper chelate(s) with a cell growth medium, which provides the stem cells with conditions for cell proliferation, and with the stem cells, so as to keep substantially unchanged by this mixing a free copper concentration in the cell growth medium, to thereby expand the stem cells, while at the same time reversibly inhibit differentiation of the stem cells; and genetically modifying the stem cells with the exogene.

According to further features in preferred embodiments of the invention described below, the genetically modifying step is effected by a vector including the exogene.

According to still an additional aspect of the present invention there is provided a method of adoptive immunotherapy. The method comprises obtaining progenitor hematopoietic cells from a patient; providing the progenitor hematopoietic cells ex-vivo with conditions for cell proliferation and with an effective amount of at least one copper chelate, so as to maintain a free copper concentration available to the cells substantially unchanged, to thereby expand the progenitor hematopoietic cells, while at the same time reversibly inhibit differentiation of the progenitor hematopoietic cells; and transplanting the progenitor hematopoietic cells to the patient.

Alternatively, the method of adoptive immunotherapy according to the present invention comprises obtaining progenitor hematopoietic cells from a patient; providing at least one copper chelate; and thereafter mixing an effective amount of the copper chelate(s) with a cell growth medium, which provides the cells with conditions for cell proliferation, and with the progenitor hematopoietic cells, so as to keep substantially unchanged by the mixing a free copper concentration in the cell growth medium, to thereby expand a population of the progenitor hematopoietic cells, while at the same time reversibly inhibit differentiation of the progenitor hematopoietic cells; and transplanting the progenitor hematopoietic cells to the patient.

According to yet a further aspect of the present invention there is provided an ex vivo expanded population of stem and/or progenitor cells, the expanded population of stem and/or progenitor cells is obtained by providing harvested stem and/or progenitor cells with conditions for cell proliferation and with an effective amount of at least one copper chelate, so as to maintain a free copper concentration available to the cells substantially unchanged, to thereby expand the population of the harvested stem and/or progenitor cells, while at the same time reversibly inhibit differentiation of the harvested stem and/or progenitor cells.

Alternatively, the expanded population of stem and/or progenitor cells is obtained by providing at least one copper chelate; and thereafter mixing an effective amount of the copper chelate(s) with a cell growth medium, which provides the stem and/or progenitor cells with conditions for cell proliferation, and with harvested stem and/or progenitor cells, so as to keep substantially unchanged by this mixing a free copper concentration in the cell growth medium, to thereby expand the harvested stem and/or progenitor cells, while at the same time reversibly inhibit differentiation of the harvested stem and/or progenitor cells.

According to further features in preferred embodiments of the invention described below, the stem and/or progenitor cells are enriched in cells characterized by an absence, or substantially diminished expression of cell surface antigens CD38, CD3, CD61, CD33, CD14, CD15 or CD4.

According to still a further aspect of the present invention there is provided another method of ex vivo expanding a population of stem and/or progenitor cells, while at the same time reversibly inhibiting differentiation of the stem and/or progenitor cells. This method comprises obtaining from a donor a mixed population of cells which comprises the stem and/or progenitor cells; and culturing the mixed population of cells ex vivo under conditions for proliferation of the stem and/or progenitor cells and with an effective amount of at least one copper chelate or chelator, to thereby expand the population of the stem and/or progenitor cells, while at the same time reversibly inhibit differentiation of the stem and/or progenitor cells.

According to further features in preferred embodiments of the invention described below, the mixed population of cells includes a mononuclear fraction of neonatal umbilical cord blood cells.

According to still further features in the described preferred embodiments the method further comprises separating the stem or/or progenitor cells from the mixed population of cells.

According to further features in preferred embodiments of the invention described below, the conditions for cell proliferation include providing the stem and/or progenitor cells with nutrients and cytokines.

According to still further features in the described preferred embodiments the cytokines are early acting cytokines, such as, but not limited to, stem cell factor, FLT-3 ligand, interleukin-6, thrombopoietin and interleukin-3.

According to still further features in the described preferred embodiments the cytokines are late acting cytokines, such as, but not limited to, granulocyte colony stimulating factor, granulocyte/macrophage colony stimulating factor and erythropoietin.

According to still further features in the described preferred embodiments the stem and/or progenitor cells are selected from the group consisting of hematopoietic cells, neural cells, oligodendrocyte cells, skin cells, hepatic cells, embryonic cells, plant cells, muscle cells, bone cells, mesenchymal cells, pancreatic cells, chondrocytes and stroma cells.

According to still further features in the described preferred embodiments the hematopoietic cells are derived or obtained from a source selected from the group consisting of bone marrow, peripheral blood and neonatal umbilical cord blood.

According to still further features in the described preferred embodiments the hematopoietic cells are enriched for stem and/or progenitor cells, such as $CD_{34}+$ cells.

According to still further features in the described preferred embodiments the cells stem and/or progenitor are selected from the group consisting of non-differentiated stem cells and early progenitor cells.

According to an additional aspect of the present invention there is provided a pharmaceutical composition comprising, as an active ingredient, at least one copper chelate and a pharmaceutical acceptable carrier. The pharmaceutical composition is preferably packaged in a container and identified in print in or on the container for use in treatment of a medical condition in which stem and/or progenitor cell depletion is evident and/or for use in stem cell expansion.

According to another aspect of the present invention there is provided a method of in vivo expanding a population of stem and/or progenitor cells, while at the same time reversibly inhibiting differentiation of the stem and/or progenitor cells. The method comprises administrating to a subject in need thereof a therapeutically effective amount of at least one copper chelate, so as to keep substantially unchanged by the administrating a free copper concentration of the subject, to thereby in vivo expand the population of the stem and/or progenitor cells, while at the same time reversibly inhibit differentiation of the stem and/or progenitor cells.

According to still another aspect of the present invention, there is provided a method of mobilization of bone marrow stem cells into the peripheral blood of a donor for harvesting the bone marrow stem cells. The method comprises administering to the donor an effective amount of at least one copper chelate, to thereby in vivo expand the bone marrow stem cells, while at the same time reversibly inhibit differentiation of the bone marrow stem cells; and harvesting the bone marrow stem cells by leukapheresis.

According to yet another aspect of the present invention, there is provided a method of decelerating maturation/differentiation of erythroid precursor cells for the treatment of β-hemoglobinopathic patients. The method comprises administering to a patient in need thereof an effective amount of at least one copper chelate, to thereby in vivo expand the population of the erythroid precursor cells, while at the same time reversibly inhibit differentiation of the erythroid precursor cells, such that upon removal of the copper chelate from the body, the erythroid precursor cells undergo accelerated maturation resulting in elevated production of fetal hemoglobin.

According to a further aspect of the present invention there is provided a method of preservation of stem and/or progenitor cells. The method comprises handling the stem cells in at least one of the steps selected from the group consisting of harvest, isolation and storage, in a presence of at least one copper chelate, which substantially inhibits differentiation of the stem and/or progenitor cells.

According to yet a further aspect of the present invention there is provided a kit for collecting and/or culturing stem and/or progenitor cells. The kit comprises a container including a culture medium supplemented with an effective amount of at least one copper chelate, which substantially inhibits differentiation of the stem and/or progenitor cells; and a packaging material identifying the kit for use in the collecting and/or culturing the stem and/or progenitor cells. Preferably, the kit further comprises cytokines, as described hereinabove.

Further preferably, the kit further comprises a separation and/or washing buffer, which includes an effective amount of at least one copper chelate, which substantially inhibits differentiation of the and/or progenitor stem cells.

According to still a further aspect of the present invention there is provided an assay of determining whether a transition metal chelate causes inhibition or induction of differentiation of stem and/or progenitor. The assay comprises culturing a population of the stem and/or progenitor cells of a substantially non-differentiated cell line, in the presence of the transition metal chelate and monitoring differentiation of the stem and/or progenitor cells, wherein if differentiation is increased as is compared to non-treated stem and/or progenitor cells, the transition metal chelate induces differentiation, whereas if differentiation is decreased or as compared to non-treated stem and/or progenitor cells, or if differentiation is absent altogether, the transition metal chelate inhibits differentiation.

The copper chelate(s) used in the various aspects of the present invention described hereinabove preferably comprise a polyamine chelator. According to further features in preferred embodiments of the invention described below, the polyamine chelator is capable of forming an organometallic complex with a transition metal other than copper. The transition metal can be, for example, zinc, cobalt, nickel, iron, palladium, platinum, rhodium and ruthenium.

According to still further features in the described preferred embodiments the polyamine chelator is a linear polyamine.

Preferably, the linear polyamine has a general formula I:

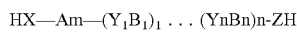

Formula I

Wherein m is an integer from 1 to 10; n is an integer from 0 to 20; X and Z are each independently selected from the group consisting of an oxygen atom, a sulfur atom and a —NH group; $Y_1$ and Yn are each independently selected from the group consisting of an oxygen atom, a sulfur atom and a —NH group; A is an alkylene chain having between 1 and 10 substituted and/or non-substituted carbon atoms; and $B_1$ and Bn are each independently an alkylene chain having between 1 and 20 substituted and/or non-substituted carbon atoms, provided that at least one of the X, Z, $Y_1$ and Yn is a —NH group and/or at least one of the carbon atoms in the alkylene chains is substituted by an amine group.

According to still further features in the described preferred embodiments, A is an alkylene chain having a general formula II:

Formula II

Wherein g is an integer that equals 0 or 3-10; and each of $R_1$, $R_2$ and Rg is independently selected from the group consisting of hydrogen, alkyl, alkenyl, alkynyl, aryl, cycloalkyl, heteroalicyclic, heteroaryl, halo, amino, alkylamino, arylamino, cycloalkylamino, heteroalicyclic amino, heteroarylamino, hydroxy, alkoxy, aryloxy, azo, C-amido, N-amido, ammonium, thiohydroxy, thioalkoxy, thioaryloxy, sulfonyl, sulfinyl, N-sulfonamide, S-sulfonamide, phosphonyl, phosphinyl, phosphonium, carbonyl, thiocarbonyl, C-carboxy, O-carboxy, C-thiocarboxy, thiocarboxy, N-carbamate, O-carbamate, N-thiocarbamate, O-thiocarbamate, urea, thiourea, borate, borane, boroaza, silyl, siloxy, silaza, aquo, alcohol, peroxo, amine oxide, hydrazine, alkyl hydrazine, aryl hydrazine, nitric oxide, cyanate, thiocyanate, isocyanate, isothiocyanate, cyano, alkylnitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, carboxylic acid, alkyl carboxylic acid, aryl carboxylic acid, sulfate, sulfite, bisulfite, thiosulfate, thiosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, phosphate, thiophosphate, phosphite, pyrophosphite, triphosphate, hydrogen phosphate, dihydrogen phosphate, guanidino, S-dithiocarbamate, N-dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraarylborate, tetraalkyl borate, tartarate, salicylate, succinate, citrate, ascorbate, saccharirate, amino acid, hydroxamic acid and thiotosylate.

According to still further features in the described preferred embodiments, each of B1 and Bn is independently an alkylene chain having a general formula III:

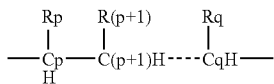
Formula III

Wherein p is an integer that equals 0 or g+1; q is an integer from g+2 to g+20; and each of Rp, Rp+1 and Rq is independently selected from the group consisting of the substituents described hereinabove with respect to $R_1$, $R_2$ and Rg.

According to still further features in the described preferred embodiments at least one of $C_1$, $C_2$ and Cg and/or at least one of Cp, Cp+1 and Cq is a chiral carbon atom.

A preferred linear polyamine according to the present invention is tetraethylenepentamine.

According to still further features in the described preferred embodiments the polyamine chelator is a cyclic polyamine, such as cyclam.

According to still further features in the described preferred embodiments the cyclic polyamine has a general formula IV:

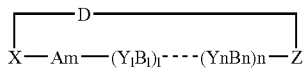
Formula IV wherein m is an integer from 1 to 10; n is an integer from 0 to 20; X and Z are each independently selected from the group consisting of an oxygen atom, a sulfur atom and a —NH group; $Y_1$ and Yn are each independently selected from the group consisting of an oxygen atom, a sulfur atom and a —NH group; A is an alkylene chain having between 1 and 10 substituted and/or non-substituted carbon atoms; B1 and Bn are each independently an alkylene chain having between 1 and 20 substituted and/or non-substituted carbon atoms; and D is a bridging group having a general formula V:

 Formula V whereas U and V are each independently selected from the group consisting of substituted hydrocarbon chain and non-substituted hydrocarbon chain; and W is selected from the group consisting of amide, ether, ester, disulfide, thioether, thioester, imine and alkene, provided that at least one of the X, Z, $Y_1$ and Yn is a —NH group and/or at least one of the carbon atoms in the alkylene chains is substituted by an amine group.

According to still further features in the described preferred embodiments, A and each of B1 and Bn in Formula IV are alkylene chains having the general formulas II and III, as is described hereinabove.

According to still further features in the described preferred embodiments the cyclic polyamine has a general formula selected from the group consisting of:

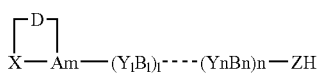
Formula VI

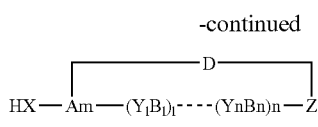
Formula VII

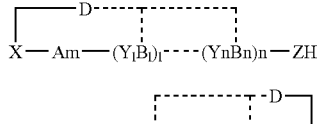
Formula VIII

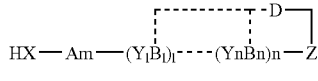
Formula IX

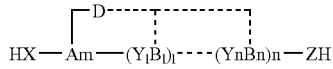
Formula X wherein m is an integer from 1 to 10; n is an integer from 0 to 20; X and Z are each independently selected from the group consisting of an oxygen atom, a sulfur atom and a —NH group; $Y_1$ and Yn are each independently selected from the group consisting of an oxygen atom, a sulfur atom and a —NH group; A is an alkylene chain having between 1 and 10 substituted and/or non-substituted carbon atoms; B1 and Bn are each independently an alkylene chain having between 1 and 20 substituted and/or non-substituted carbon atoms; and D is a bridging group having a general formula V, as described hereinabove, and further wherein should the D is attached at one end to A (Formulas VI, VII and X), the U or the V are being attached to one carbon atom in the alkylene chain and should the D is attached at one end to B1 or Bn (Formulas VIII, IX and X), the U or the V are being attached to one carbon atom in the alkylene chain, provided that at least one of the X, Z, $Y_1$ and Yn is a —NH group and/or at least one of the carbon atoms in the alkylene chains is substituted by an amine group.

The alkylene chains A, B1 and Bn are preferably as described hereinabove.

According to still further features in the described preferred embodiments the polyamine chelator includes at least one linear polyamine and at least one cyclic polyamine.

Such a polyamine chelator preferably has a general formula XI:

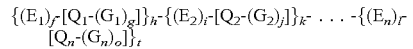
Formula XI wherein n is an integer greater than 1; each of f, g, h, i, j, k, l, o and t is independently an integer from 0 to 10; each of $E_1$, $E_2$ and En is independently a linear polyamine as is described hereinabove; each of $G_1$, $G_2$ and Gn is independently a cyclic polyamine as is described hereinabove; and each of $Q_1$, $Q_2$ and Qn is independently a linker linking between two of the polyamines, provided that at least one of the $Q_1$, $Q_2$ and Qn is an amine group and/or at least one of the linear polyamine and the cyclic polyamine is having at least one free amine group.

According to still further features in the described preferred embodiments each of $Q_1$, $Q_2$ and Qn is independently selected from the group consisting alkylene, alkenylene, alkynylene, arylene, cycloalkylene, hetroarylene, amine, azo, amide, sulfonyl, sulfinyl, sulfonamide, phosphonyl, phosphinyl, phosphonium, ketoester, carbonyl, thiocarbonyl, ester, ether, thioether, carbamate, thiocarbamate, urea, thiourea, borate, borane, boroaza, silyl, siloxy and silaza.

According to still further features in the described preferred embodiments the polyamine chelator is selected from the group consisting of ethylendiamine, diethylenetriamine, triethylenetetramine, triethylenediamine, tetraethylenepentamine, aminoethylethanolamine, aminoethylpiperazine, pentaethylenehexamine, captopril, penicilamine, N,N'-bis(3-aminopropyl)-1,3-propanediamine, N,N'-Bis-(2-animoethyl)-1,3-propanediamine, 1,7-dioxa-4,10-diazacyclododecane, 1,4,8,11-tetraazacyclotetradecane-5,7-dione, 1,4,7-triazacyclononane, 1-oxa-4,7,10-triazacyclododecane, 1,4,8,12-tetraazacyclopentadecane, and 1,4,7,10-tetraazacyclododecane.

The present invention successfully addresses the shortcomings of the presently known configurations by providing methods, pharmaceutical compositions and kits which utilize copper chelates and can be used for expanding a population of stem and/or progenitor cells while at the same time reversibly inhibiting differentiation of the stem and/or progenitor cells. The methods, the pharmaceutical composition and the kit of the present invention have uses in various therapeutic applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3a is a photomicrograph of 8-weeks old hematopoietic cells treated with the chelate, showing mainly blast-like cells, indicative of non-differentiated stem cells. FIG. 3b is a photomicrograph of 8-weeks old untreated hematopoietic, showing mainly differentiated cells.

FIG. 18 shows the comparative numbers of colony-forming cells (CFUs) measured from cultures at weekly intervals.

DESCRIPTION OF THE PREFERRED EMBODIMENTS

Figure 1:
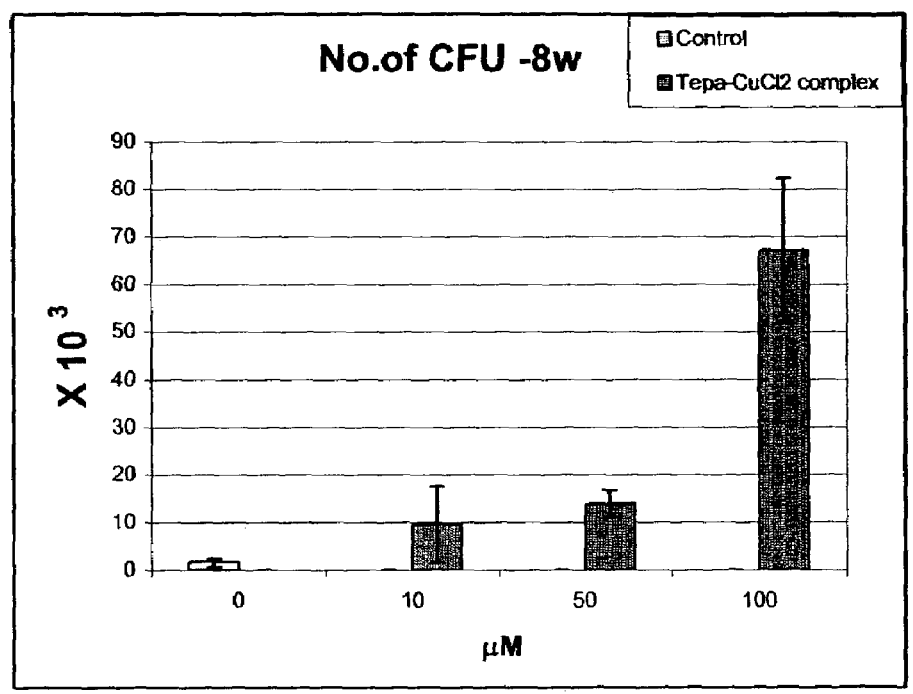
FIG. 1 illustrates the long-term effect of TEPA-copper (TEPA-Cu) is chelate on the expansion of $CD_{34}^+$ hematopoietic stem cells, cultured ex vivo. Purified $CD_{34}^+$ cells were plated in liquid culture, at $10^4$ cell/ml, in the presence of cytokines, with or without different concentrations of the chelate. The Figure shows the comparative numbers of colony-forming units (CFUs) measured in 8 weeks old cultures treated, or untreated, with the chelate.

The present invention is of methods of controlling proliferation and/or modulating differentiation of stem and/or progenitor cells, which can be used for ex-vivo or in vivo expansion of stem and/or progenitor cells. Specifically, the present invention can be used to provide expanded population of stem and/or progenitor cells, which are usefull in clinical procedures involving stem cell therapy, such as, hematopoietic stem cell transplantations, and for generation of stem or progenitor cells suitable for genetic manipulations, to be used in, for example, ex vivo gene therapy procedures. The present invention can be used for treating diseases such as, but not limited to, β-hemoglobinopathia, and in transplantation of stem cells in trans-differentiation setting for replenishing missing or damaged cells of an organ. The present invention is further of methods of expanding a population of stem and/or progenitor cells present in a mixed population of cells.

The principles and operation of the methods according to the present invention may be better understood with reference to the drawings and accompanying descriptions and examples.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As is discussed hereinabove, International Patent Applications Serial Nos. PCT/IL99/00444 and PCT/US99/02664, U.S. patent applications Ser. Nos. 09/986,897; and 09/988, 127 and Peled et al. [36] teach that transition metal chelators, copper chelators in particular, can inhibit differentiation of stem and progenitor cells, thereby prolonging cell proliferation and expansion ex vivo. These disclosures also teach that the elevation of cellular copper content can accelerate differentiation of stem or progenitor cells. Based on these findings, it was thus assumed that cellular copper is involved in the modulation of stem or progenitor cell self-renewal, proliferation and differentiation, such that increasing cellular copper content accelerates differentiation of stem or progenitor cells, while decreasing of cellular copper content inhibits differentiation of stem or progenitor cells.

While continuing to evaluate the effect of cellular copper on proliferation, differentiation and self-renewal of cells, the present inventors have surprisingly and unexpectedly discovered that the addition of copper chelates to culture media substantially promoted the proliferation and inhibited the differentiation of stem and progenitor cells ex vivo.

This surprising discovery clearly indicated that the effect of certain chelates on proliferation and differentiation of stem and progenitor cells cannot be solely explained only by modulation of the content of cellular copper and that additional regulatory pathways must be affected by specific attributes of the copper chelate molecules.

Accordingly, in one aspect, the present invention provides methods and compositions which utilize transition metal chelates, copper chelates in particular, for controlling proliferation and differentiation of stem and progenitor cells.

Enhancing or maximizing the expansion of stem and progenitor cells, using transition metal (e.g., copper) chelates, can be advantageously applied ex vivo and in vivo in several clinical situations. Representative examples of such clinical situations are listed hereinbelow:

Hematopoietic cell transplantation: Transplantation of hematopoietic cells has become the treatment of choice for a variety of inherited or malignant diseases. While early transplantation procedures utilized the entire bone marrow (BM) population, recently, more defined populations, enriched for stem cells ($CD_{34}^+$ cells) have been used [1].

In addition to the marrow, such cells could be derived from other sources such as peripheral blood (PB) and neonatal umbilical cord blood (CB) [2]. As compared with the bone marrow, transplantation with PB cells shortens the period of pancytopenia and reduces the risks of infection and bleeding [3-5].

An additional advantage of using PB for transplantation is its accessibility. The limiting factor for PB transplantation is the low number of circulating pluripotent stem/progenitor cells.

To obtain enough PB-derived stem cells for transplantation, these cells are "harvested" by repeated leukapheresis following their mobilization from the marrow into the circulation by treatment with chemotherapy and cytokines [3-4]. Such treatment is obviously not suitable for normal donors.

Hence, the use of ex-vivo expended stem cells for transplantation is highly advantageous for the following reasons [2, 6-7]: It reduces the volume of blood required for reconstitution of an adult hematopoietic system and may obviate the need for mobilization and leukapheresis [3]; and It enables storage of small number of PB or CB stem cells for potential future use.

Furthermore, in the case of autologous transplantation of patients with malignancies, contaminating tumor cells in autologous infusion often contribute to the recurrence of the disease [3]. Selecting and expanding $CD_{34}^+$ stem cells will reduce the load of tumor cells in the final transplant. The cultures provide a significant depletion of T lymphocytes, which may be useful in the allogeneic transplant setting for reducing graft-versus-host disease.

Clinical studies have indicated that transplantation of ex-vivo expanded cells derived from a small number of PB $CD_{34}^+$ cells can restore hematopoiesis in patients treated with high doses of chemotherapy, although these results have not allowed yet firm conclusion about the long term in-vivo hematopoietic capabilities of these cultured cells [3-4].

For successful transplantation, shortening of the duration of the cytopenic phase, as well as long-term engraftment, is crucial. Inclusion of intermediate and late progenitor cells in the transplant could accelerate the production of donor-derived mature cells and shortens the cytopenic phase. It is important, therefore, that ex-vivo expanded cells will include, in addition to stem cells, more differentiated progenitors in order to optimize short-term recovery and long-term restoration of hematopoiesis. Expansion of intermediate and late progenitor cells, especially those committed to the neutrophilic and megakaryocytic lineages, concomitant with expansion of stem cells, should serve this purpose [8].

Such cultures may be useful not only in restoring hematopoiesis in completely bone marrow ablated patients but also as supportive measure for shortening bone marrow recovery following conventional radio- or chemo-therapies.

Prenatal diagnosis of genetic defects in scarce cells: Prenatal diagnosis involved the collection of embryonic cells from a pregnant woman and analysis thereof for genetic defects. A preferred, non-invasive, way of collecting embryonic cells involves separation of embryonic nucleated red blood cell precursors that infiltrated into the maternal blood circulation. However, being very scarce, such cells should undergo cell expansion prior to analysis. The present invention therefore offers means to expand embryonic cells for prenatal diagnosis.

Gene therapy: In order to achieve a successful long-term gene therapy a high frequency of genetically modified stem cells that have integrated the transgene into their genome is an obligatory requirement. In the BM tissue, while the majority of the cells are cycling progenitors and precursors, the stem cells constitute only a small fraction of the cell population and most of them are in a quiescent, non-cycling state. As viral-based (e.g., retroviral) vectors require active cell division for integration of the transgene into the host genome, gene transfer into fresh BM stem cells is very inefficient. Hence, the ability to expand a purified population of stem cells and to regulate their cell division ex-vivo would permit increased probability of their genetic modification [9].

Adoptive immunotherapy: Ex-vivo-expanded, defined lymphoid subpopulations have been studied and used for adoptive immunotherapy of various malignancies and of immunodeficiency, viral and genetic diseases [10-12].

Such a treatment enhances the required immune response or replaces deficient functions. This approach was pioneered clinically by Rosenberg et al. [13] using a large number of autologous ex-vivo expanded non-specific killer T cells, and subsequently ex-vivo expanded specific tumor infiltrating lymphocytes.

Functionally active antigen-presenting cells, which are grown from a starting population of $CD_{34}^+$ PB cells in cytokine-supported cultures have also been studied. These cells can introduce soluble protein antigens to autologous T cells in-vitro and, thus, offer new prospects for the immunotherapy of minimal residual disease after high dose chemotherapy. Ex-vivo expansion of antigen-presenting dendritic cells has also been studied [14-16].

Ex-vivo expansion of non-hematopoietic stem and progenitor cells: Ex-vivo expansion of non-hematopoietic stem and progenitor cells, such as, for example neural stem cells or oligodendrocyte progenitors, is also highly beneficial in various applications.

For example, myelin disorders form an important group of human neurological diseases that are as yet incurable. Progress in animal models, particularly in transplanting cells of the oligodendrocyte lineage, has resulted in significant focal remyelination and physiological evidence of restoration of function [35]. Therefore, future therapies are expected to involve both transplantation and promotion of endogenous repair, with the two approaches being combined with ex-vivo manipulation of the donor tissue.

U.S. Pat. No. 5,486,359 teaches isolated human mesenchymal stem cells which can differentiate into more than one tissue type (e.g. bone, cartilage, muscle or marrow stroma) and a method for isolating, purifying, and culturally expanding human mesenchymal stem cells.

U.S. Pat. No. 5,736,396 teaches methods for in-vitro or ex-vivo lineage-directed induction of isolated, culture expanded human mesenchymal stem cells, which are effected by contacting the mesenchymal stem cells with a bioactive factor effective to induce differentiation thereof into a lineage of choice. U.S. Pat. No. 5,736,396 further teaches a method which further includes introducing such culturally expanded lineage-induced mesenchymal stem cells into a host from which they have originated, for purposes of mesenchymal tissue regeneration or repair.

U.S. Pat. No. 4,642,120 teaches compositions for repairing defects of cartilage and bones. The disclosed compositions are provided in gel form either as is, or embedded in natural or artificial bones. The gel comprises certain types of cells such as committed embryonal chondocytes or any kind of mesenchyme originated cells which potentially can be converted to cartilage cells, generally by the influence of chondrogenic inducing factors, in combination with fibrinogen, antiprotease and thrombin.

U.S. Pat. No. 5,654,186 teaches that blood-borne mesenchymal cells proliferate in culture and in vivo, in animal models, and are capable of migrating into wound sites from the blood to form skin.

U.S. Pat. No. 5,716,411 teaches a method of skin regeneration of a wound or burn in an animal or human, which is effected by initially covering the wound with a collagen glycosaminoglycan matrix, allowing infiltration of the grafted GC matrix by mesenchymal cells and blood vessels from healthy underlying tissue and thereafter applying a cultured epithelial autograft sheet grown from epidermal cells derived from the animal or human at a wound-free site on the animal's or human's body surface. The resulting graft has excellent take rates and has the appearance, growth, maturation and differentiation of normal skin.

U.S. Pat. No. 5,716,616 teaches methods of treating patients suffering from a disease, disorder or condition characterized by a bone cartilage or lung defects. These methods are effected by intravenous administration of stromal cells isolated from normal syngeneic individuals or intravenous administration of stromal cells isolated from the patient subsequent to correction of the genetic defect in the isolated cells. Methods of introducing genes into a recipient individual are also disclosed in this reference, and are effected by obtaining a bone marrow sample from either the recipient individual or a matched syngeneic donor, isolating adherent cells from the sample, transfecting the adherent cells that were isolated from the recipient or a matched syngeneic donor with a gene and administering the transfected adherent cells to the recipient individual intravenously. Compositions that comprise isolated stromal cells that include exogenous genes operably linked to regulatory sequences are further disclosed.

In each of the above examples, non-hematopoietic stem and progenitor cells are used as an external source of cells for replenishing missing or damaged cells of an organ. Such a use requires cell expansion prior to differentiation in order to primarily obtain the required cell mass. It is in this step where the method of the present invention can become highly effective and useful and hence can be beneficial, for example, while implementing any of the methods disclosed in the above U.S. patents.

It will be appreciated in this regard that transdifferentiation protocols ca also find uses for ex vivo expanded stem cells.

Additional examples for both ex-vivo and in-vivo applications: Ex-vivo and in-vivo expansion of stem and progenitor cells can be also utilized in skin regeneration, hepatic regeneration, muscle regeneration and bone growth in osteoporosis.

Mobilization of bone marrow stem cells into the peripheral blood (peripheralization): As is discussed hereinabove, PB-derived stem cells for transplantation are "harvested" by repeated leukapheresis following their mobilization from the marrow into the circulation by treatment with chemotherapy and cytokines [3-4].

The use of chemotherapy is, of course, not suitable for normal donors. Administration of transition metal chelates, such as TEPA-Cu, into the donor could increase the marrow stem cell pool, which is then mobilized into the periphery by endogenous or injected G-CSF.

Stimulation of fetal hemoglobin production: Increased fetal hemoglobin has been shown to ameliorate the clinical symptoms in patients having β-hemoglobinopathies such as sickle cell anemia and β-thalassemia [20].

The level of fetal hemoglobin, which normally comprises about 1% of the total hemoglobin, becomes elevated in accelerated erythropoiesis (e.g., following acute hemolysis or hemorrhage or administration of erythropoietin) [18]. It has been suggested that this phenomenon is associated with acceleration of the maturation/differentiation process of the erythroid precursors [19]. Administration of copper chelates such as TEPA-copper (TEPA-Cu) to patients with β-hemoglobinopathies might first increase and synchronize their early erythroid progenitor pool (by blocking differentiation).

Following cessation of administration of the drug and its removal from the body, this early population might undergo accelerated maturation which may result in elevated production of fetal hemoglobin.

Thus, according to one aspect of the present invention there is provided a method of ex vivo expanding a population of stem an/or progenitor cells, while at the same time, reversibly inhibiting differentiation of the cells. The method is effected by providing the cells with conditions for cell proliferation and with an effective amount of at least one copper chelate, so as to maintain a free copper concentration available to the cells substantially unchanged, to thereby expand the population of stem and/or progenitor cells, while at the same time inhibit differentiation of the cells.

According to another aspect of the present invention, there is provided a method of ex vivo expanding a population of stem and/or progenitor cells, while at the same time reversibly inhibiting differentiation of the stem and/or progenitor cells. The method is effected by providing at least one copper chelate, and thereafter mixing an effective amount of the copper chelate(s) with a population of stem and/or progenitor cells and a cell growth medium, so as to keep substantially unchanged by this mixing a free copper concentration in the cell growth medium, to thereby expand the population of the stem and/or progenitor cells, while at the same time reversibly inhibit differentiation of the stem and/or progenitor cells.

As used herein the term "ex-vivo" refers to cells removed from a living organism and are propagated outside the organism (e.g., in a test tube). As used herein, the term "ex-vivo", however, does not refer to cells known to propagate only in-vitro, such as various cell lines (e.g., HL-60, MEL, HeLa, etc.).

As used herein the phrase "stem cells" refers to cells that, given the right growth conditions, may develop to any cell lineage present in the organism from which they were derived.

As used herein the phrase "progenitor cells" refers to cells which are preliminarily differentiated but which are not yet lineage committed and can readily revert to stem cells.

As used herein the term "inhibiting" refers to slowing, decreasing, delaying, preventing or abolishing.

As used herein the term "differentiation" refers to a change from relatively generalized to specialized kinds during development. Cell differentiation of various cell lineages is a well-documented process and requires no further description herein. As used herein the term "differentiation" is distinct from maturation which is a process, although some times associated with cell division, in which a specific cell type mature to function and then dies, e.g., via programmed cell death (apoptosis).

As used herein the phrase "cell expansion" refers to a process of cell proliferation substantially devoid of cell differentiation. Cells that undergo expansion hence maintain their renewal properties and are oftentimes referred to herein as renewable cells, e.g., renewable stem cells.

The copper chelate, according to the present invention, is used in these and other aspects of the present invention, in the context of expanding a population of stem and/or progenitor cells, while at the same time reversibly inhibiting differentiation of the stem and/or progenitor cells. Providing the cells with the copper chelate maintains the free copper concentration available to the cells substantially unchanged.

The copper chelate according to the present invention is oftentimes capable of forming an organometallic complex with a transition metal other than copper. As metals other than copper are typically present in the cells (e.g., zinc) or can be administered to cells during therapy (e.g., platinum), it was found that copper chelates that can also interact with other metals are highly effective. Representative examples of such transition metals include, without limitation, zinc, cobalt, nickel, iron, palladium, platinum, rhodium and ruthenium.

The copper chelates of the present invention comprise copper ion (e.g., $Cu^{+1}$, $Cu^{+2}$) and one or more chelator(s). As is discussed hereinabove, preferred copper chelators include polyamine molecules, which can form a cyclic complex with the copper ion via two or more amine groups present in the polyamine.

Hence, the copper chelate used in the context of the different aspects and embodiments of the present invention preferably includes a polyamine chelator, namely a polymeric chain that is substituted and/or interrupted with 1-10 amine moieties, preferably 2-8 amine moieties, more preferably 4-6 amine moieties and most preferably 4 amine moieties.

The phrases "amine moiety", "amine group" and simply "amine" are used herein to describe a —NR'R" group or a —NR'— group, depending on its location within the molecule, where R' and R" are each independently hydrogen, alkyl, cycloalkyl, aryl, heteroaryl or heterocyclic, as these terms are defined hereinbelow.

The polyamine chelator can be a linear polyamine, a cyclic polyamine or a combination thereof.

A linear polyamine, according to the present invention, can be a polyamine that has a general formula I:

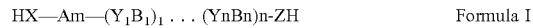

HX—Am—$(Y_1B_1)_1$ ... $(YnBn)n$-ZH      Formula I wherein m is an integer from 1 to 10; n is an integer from 0 to 20; X and Z are each independently selected from the group consisting of an oxygen atom, a sulfur atom and a —NH group; $Y_1$ and Yn are each independently selected from the group consisting of an oxygen atom, a sulfur atom and a —NH group; A is an alkylene chain having between 1 and 10 substituted and/or non-substituted carbon atoms; and $B_1$, and Bn are each independently an alkylene chain having between 1 and 20 substituted and/or non-substituted carbon atoms, provided that at least one of X, Z, $Y_1$, and Yn is a —NH group and/or at least one of the carbon atoms in the alkylene chains is substituted by an amine group.

Hence, the linear polyamine, according to the present invention, is preferably comprised of one or more alkylene chains (Am, $B_1$ ... Bn, in Formula I), is interrupted by one or more heteroatoms such as S, O and N ($Y_1$ ... Yn in Formula I), and terminates with two such heteroatoms (X and Z in Formula I).

Alkylene chain A, as is described hereinabove, includes 1-10 substituted or non-substituted carbon atoms and is connected, at least at one end thereof, to a heteroatom (e.g., X in Formula I). Whenever there are more than one alkylene chains A (in cases where m is greater than one), only the first alkylene chain A is connected to X. However, m is preferably 1 and hence the linear polyamine depicted in Formula I preferably includes only one alkylene chain A.

Alkylene chain B, as is described hereinabove, includes between 1 and 20 substituted or non-substituted carbon atoms. The alkylene chain B is connected at its two ends to a heteroatom ($Y_1$ ... Yn and Z in Formula I).

The preferred linear polyamine delineated in Formula I comprises between 1 and 20 alkylene chains B, denoted as $B_1$ ... Bn, where "$B_1$ ... Bn" is used herein to describe a plurality of alkylene chains B, namely, $B_1$, $B_2$, $B_3$, ..., Bn−1 and Bn, where n equals 0-20. These alkylene chains can be the same or different. Each of $B_1$ ... Bn is connected to the respective heteroatom $Y_1$ ... Yn, and the last alkylene chain in the structure, Bn, is also connected to the heteroatom Z.

It should be noted that herein throughout, whenever an integer equals 0 or whenever a component of a formula is followed by the digit 0, this component is absent from the structure. For example, if n in Formula I equals 0, there is no alkylene chain B and no heteroatom Y are meant to be in the structure.

Preferably, n equals 2-10, more preferably 2-8 and most preferably 3-5. Hence, the linear polyamine depicted in Formula I preferably includes between 3 and 5 alkylene chains B, each connected to 3-5 heteroatoms Y.

The linear polyamine depicted in Formula I must include at least one amine group, as this term is defined hereinabove, preferably at least two amine groups and more preferably at least four amine groups. The amine group can be present in the structure as the heteroatoms X, Z or $Y_1$ ... Yn, such that at least one of X, Z and $Y_1$ ... Yn is a —NH— group, or as a substituent of one or more of the substituted carbon atoms in the alkylene chains A and $B_1$ ... Bn. The presence of these amine groups is required in order to form a stable chelate with the copper ion, as is discussed hereinabove.

The alkylene chain A preferably has a general Formula II:

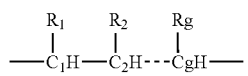

Formula II wherein g is an integer that equals 0 or 3-10.

Hence, the alkylene chain A is comprised of a plurality of carbon atoms $C_1, C_2, C_3 \ldots, Cg-1$ and $Cg$, substituted by the respective $R_1, R_2, R_3 \ldots, Rg-1$ and $Rg$ groups. Preferably, the alkylene chain A includes 2-10 carbon atoms, more preferably, 2-6 and most preferably 2-4 carbon atoms.

As is defined hereinabove, in cases where g equals 0, the component CgH(Rg) is absent from the structure and hence the alkylene chain A comprises only 2 carbon atoms.

$R_1$, $R_2$ and Rg are each a substituent attached to the carbon atoms in A. Each of $R_1$, $R_2$ and Rg can independently be a substituent such as, but not limited to, hydrogen, alkyl, alkenyl, alkynyl, aryl, cycloalkyl, heteroalicyclic, heteroaryl, halo, amino, alkylamino, arylamino, cycloalkylamino, heteroalicyclic amino, heteroarylamino, hydroxy, alkoxy, aryloxy, azo, C-amido, N-amido, ammonium, thiohydroxy, thioalkoxy, thioaryloxy, sulfonyl, sulfinyl, N-sulfonamide, S-sulfonamide, phosphonyl, phosphinyl, phosphonium, carbonyl, thiocarbonyl, C-carboxy, O-carboxy, C-thiocarboxy, O-thiocarboxy, N-carbamate, O-carbamate, N-thiocarbamate, O-thiocarbamate, urea, thiourea, borate, borane, boroaza, silyl, siloxy, silaza, aquo, alcohol, peroxo, amine oxide, hydrazine, alkyl hydrazine, aryl hydrazine, nitric oxide, cyanate, thiocyanate, isocyanate, isothiocyanate, cyano, alkylnitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, carboxylic acid, alkyl carboxylic acid, aryl carboxylic acid, sulfate, sulfite, bisulfite, thiosulfate, thiosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, phosphate, thiophosphate, phosphite, pyrophosphite, triphosphate, hydrogen phosphate, dihydrogen phosphate, guanidino, S-dithiocarbamate, N-dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraarylborate, tetraalkyl borate, tartarate, salicylate, succinate, citrate, ascorbate, saccharirate, amino acid, hydroxamic acid and thiotosylate.

Whenever $R_1$, $R_2$ or Rg is hydrogen, its respective carbon atom in a non-substituted carbon atom.

As used herein, the term "alkyl" is a saturated aliphatic hydrocarbon including straight chain and branched chain groups. Preferably, the alkyl group has 1 to 20 carbon atoms. More preferably, it is a medium size alkyl having 1 to 10 carbon atoms. Most preferably, it is a lower alkyl having 1 to 4 carbon atoms. The alkyl group may be substituted or non-substituted. When substituted, the substituent group can be, for example, cycloalkyl, aryl, heteroaryl, heteroalicyclic, hydroxy, alkoxy, aryloxy, thiohydroxy, thioalkoxy, thioaryloxy, cyano, halo, carbonyl, thiocarbonyl, O-carbamate, N-carbamate, O-thiocarbamate, N-thiocarbamate, C-amido, N-amido, C-carboxy, O-carboxy, nitro, sulfonamide, silyl, guanidine, urea or amino, as these terms are defined hereinbelow.

The term "alkenyl" describes an alkyl group which consists of at least two carbon atoms and at least one carbon-carbon double bond.

The term "alkynyl" describes an alkyl group which consists of at least two carbon atoms and at least one carbon-carbon triple bond.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamate, N-carbamate, C-amido, N-amido, nitro, or amino, as these terms are defined hereinabove or hereinbelow.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamate, N-carbamate, O-thiocarbamate, N-thiocarbamate, C-amido, N-amido, sulfinyl, sulfonyl or amino, as these terms are defined hereinabove or hereinbelow.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamide, C-carboxy, O-carboxy, sulfinyl, sulfonyl, O-carbamate, N-carbamate, O-thiocarbamate, N-thiocarbamate, C-amido, N-amido or amino, as these terms are defined hereinabove or hereinbelow.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamate, N-carbamate, O-thiocarbamate, N-thiocarbamate, sulfinyl, sulfonyl, C-amido, N-amido or amino, as these terms are defined hereinabove or hereinbelow.

The term "halo" describes a fluorine, chlorine, bromine or iodine atom.

The term "amino", as is defined hereinabove with respect to an "amine" or an "amino group", is used herein to describe an —NR'R", wherein R' and R" are each independently hydrogen, alkyl, cycloalkyl, aryl, heteroaryl or heterocyclic, as these terms are defined hereinabove.

Hence, the terms "alkylamino", "arylamino", "cycloalkylamino", "heteroalicyclic amino" and "heteroarylamino" describe an amino group, as defined hereinabove, wherein at least one of R' and R" thereof is alkyl, aryl, cycloalkyl, heterocyclic and heteroaryl, respectively.

The term "hydroxy" describes an —OH group.

An "alkoxy" describes both an —O-alkyl and an —O-cycloalkyl group, as defined herein.

An "aryloxy" describes both an —O-aryl and an —O-heteroaryl group, as defined herein.

The term "azo" describes a —N=N group.

A "C-amido" describes a —C(=O)—NR'R" group, where R' and R" are as defined hereinabove.

An "N-amido" describes a R'C(=O)—NR"— group, where R' and R" are as defined hereinabove.

An "ammonium" describes an —N$^+$HR'R" group, where R' and R" are as defined hereinabove.

The term "thiohydroxy" describes a —SH group.

The term "thioalkoxy" describes both a —S-alkyl group and a —S-cycloalkyl group, as defined hereinabove.

The term "thioaryloxy" describes both a —S-aryl and a —S-heteroaryl group, as defined hereinabove.

A "sulfinyl" describes a —S(=O)—R group, where R can be, without limitation, alkyl, cycloalkyl, aryl and heteroaryl as these terms are defined hereinabove.

A "sulfonyl" describes a —S(=O)$_2$—R group, where R is as defined hereinabove.

A "S-sulfonamido" is a —S(=O)$_2$—NR'R" group, with R' and R" as defined hereinabove.

A "N-sulfonamido" is an R'(S=O)$_2$—NR"— group, with R' and R" as defined hereinabove.

A "phosphonyl" is a —O—P(=O)(OR')—R" group, with R' and R" as defined hereinabove.

A "phosphinyl" is a —PR'R" group, with R' and R" as defined hereinabove.

A "phosphonium" is a —P$^+$R'R"R"', where R' and R" are as defined hereinabove and R"' is defined as either R' or R".

The term "carbonyl" describes a —C(=O)—R group, where R is hydrogen, alkyl, cycloalkyl, aryl, heteroaryl (bonded through a ring carbon) or heteroalicyclic (bonded through a ring carbon) as defined hereinabove.

A "thiocarbonyl" describes a —C(=S)—R group, where R is as defined hereinabove with respect to the term "carbonyl".

A "C-carboxy" describes a —C(=O)—O—R groups, where R is as defined hereinabove with respect to the term "carbonyl".

An "O-carboxy" group refers to a RC(=O)—O— group, where R is as defined hereinabove with respect to the term "carbonyl".

A "carboxylic acid" is a C-carboxy group in which R is hydrogen.

A "C-thiocarboxy" is a —C(=S)—O—R groups, where R is as defined hereinabove with respect to the term "carbonyl".

An "O-thiocarboxy" group refers to an R—C(=S)—O— group, where R is as defined hereinabove with respect to the term "carbonyl".

The term "O-carbamate" describes an —OC(=O)—NR'R" group, with R' and R" as defined hereinabove.

A "N-carbamate" describes a R'—O—C(=O)—NR"— group, with R' and R" as defined hereinabove.

An "O-thiocarbamate" describes an —O—C(=S)—NR'R" group, with R' and R" as defined hereinabove.

A "N-thiocarbamate" describes a R'OC(=S)NR"— group, with R' and R" as defined hereinabove.

The term "urea" describes a —NR'—C(=O)—NR'R" group, with R', R" and R"' as defined hereinabove.

The term "thiourea" describes a —NR'—C(=S)—NR'R" group, with R', R" and R"' as defined hereinabove.

The term "borate" describes an —O—B—(OR)$_2$ group, with R as defined hereinabove.

The term "borane" describes a —B—R'R" group, with R' and R" as defined hereinabove.

The term "boraza" describes a —B(R')(NR"R"') group, with R', R" and R"' as defined hereinabove.

The term "silyl" describes a —SiR'R"R"', with R', R" and R"' as defined herein.

The term "siloxy" is a —Si—(OR)$_3$, with R as defined hereinabove.

The term "silaza" describes a —Si—(NR'R")$_3$, with R' and R" as defined herein.

The term "aquo" describes a H$_2$O group.

The term "alcohol" describes a ROH group, with R as defined hereinabove.

The term "peroxo" describes an —OOR group, with R as defined hereinabove.

As used herein, an "amine oxide" is a —N(=O)R'R"R"' group, with R', R" and R"' as defined herein.

A "hydrazine" is a —NR'—NR"R"' group, with R', R" and R"' as defined herein.

Hence, "alkyl hydrazine" and "aryl hydrazine" describe a hydrazine where R' is an alkyl or an aryl, respectively, and R" and R"' are as defined hereinabove.

The term "nitric oxide" is a —N=O group.

The term "cyano" is a —C≡N group.

A "cyanate" is an —O—C≡N group.

A "thiocyanate" is a "—S—C≡N group.

An "isocyanate" is a —N=C=O group.

An "isothiocyanate" is a —N=C=S group.

The terms "alkyl nitrile" and "aryl nitrile" describe a —R—C≡N group, where R is an alkyl or an aryl, respectively.

The terms "alkyl isonitrile" and "aryl isonitrile" describe a R—N≡C— group, where R is an alkyl or aryl, respectively.

A "nitrate" or "nitro" is a —NO$_2$ group.

A "nitrite" is an —O—N=O group.

An "azido" is a N$_3^+$ group.

An "alkyl sulfonic acid" and an "aryl sulfonic acid" describe a —R—SO$_2$—OH group, with R being an alkyl or an aryl, respectively.

An "alkyl sulfoxide", an "aryl sulfoxide" and an "alkyl aryl sulfoxide" describe a —R'S(=O)R" group, where R' and R" are each an alkyl, R' and R" are each an aryl and where R' is and alkyl and R" is an aryl, respectively.

An "alkyl sulfenic acid" and "aryl sulfenic acid" describe a —R—S—OH group, where R is an alkyl or an aryl, respectively.

An "alkyl sulfinic acid" and "aryl sulfinic acid" describe a —R—S(=O)—OH group where R is an alkyl or an aryl, respectively.

As used herein, the terms "alkyl carboxylic acid" and "aryl carboxylic acid" describe a —R—C(=O)—OH group, where R is an alkyl or an aryl, respectively.

An "alkyl thiol carboxylic acid" and an "aryl thiol carboxylic acid" describe a —R—C(=O)—SH group, where R is an alkyl or an aryl, respectively.

An "alkyl thiol thiocarboxylic acid" and an "aryl thiol thiocarboxylic acid" describe a —R—C(=S)—SH group, where R is an alkyl or an aryl, respectively.

A "sulfate" is a —O—SO$_2$—OR' group, with R' as defined hereinabove.

A "sulfite" group is a —O—S(=O)—OR' group, with R' as defined hereinabove.

A "bisulfite" is a sulfite group, where R' is hydrogen.

A "thiosulfate" is an —O—SO$_2$—SR' group, with R' as defined hereinabove.

A "thiosulfite" group is an —O—S(=O)—SR' group, with R' as defined hereinabove.

The terms "alkyl/aryl phosphine" describe a —R—PH$_2$ group, with R being an alkyl or an aryl, respectively, as defined above.

The terms "alkyl and/or aryl phosphine oxide" describe a —R'—PR"$_2$(=O) group, with R' and R" being an alkyl and/or an aryl, as defined hereinabove.

The terms "alkyl and/or aryl phosphine sulfide" describe a —R'—PR"$_2$(=S) group, with R' and R" being an alkyl and/or an aryl, as defined hereinabove.

The terms "alkyl/aryl phosphonic acid" describe a —R'—P(=O)(OH)$_2$ group, with R' being an alkyl or an aryl as defined above.

The terms "alkyl/aryl phosphinic acid" describes a —R'—P(OH)$_2$ group, with R' being an alkyl or an aryl as defined above.

A "phosphate" is a —O—P(=O)(OR')(OR") group, with R' and R" as defined hereinabove.

A "hydrogen phosphate" is a phosphate group, where R' is hydrogen.

A "dihydrogen phosphate" is a phosphate group, where R' and R" are both hydrogen.

A "thiophosphate" is a —S—P(=O)(OR')$_2$ group, with R' as defined hereinabove.

A "phosphite" is an —O—P (OR')$_2$ group, with R' as defined hereinabove.

A "pyrophosphite" is an —O—P—(OR')—O—P(OR")$_2$ group, with R' and R" as defined hereinabove.

A "triphosphate" describes an —OP(=O)(OR')—O—P(=O)(OR")—O—P(=O)(OR''')$_2$, with R', R" and R''' are as defined hereinabove.

As used herein, the term "guanidine" describes a —R'NC(=N)—NR"R''' group, with R', R" and R''' as defined herein.

The term "S-dithiocarbamate" describes a —SC(=S)—NR'R" group, with R' and R" as defined hereinabove.

The term "N-dithiocarbamate" describes an R'SC(=S)—NR"— group, with R' and R" as defined hereinabove.

A "bicarbonate" is an —O—C(=O)—O⁻ group.

A "carbonate" is an —O—C(=O)—OH group.

A "perchlorate" is an —O—Cl(=O)$_3$ group.

A "chlorate" is an —O—Cl(=O)$_2$ group.

A "chlorite" is an —O—Cl(=O) group.

A "hypochlorite" is an —OCl group.

A "perbromate" is an —O—Br(=O)$_3$ group.

A "bromate" is an —O—Br(=O)$_2$ group.

A "bromite" is an —O—Br(=O) group.

A "hypobromite" is an —OBr group.

A "periodate" is an —O—I(=O)$_3$ group.

A "iodate" is an —O—I(=O)$_2$ group.

The term "tetrahalomanganate" describes MnCl$_4$, MnBr$_4$ and MnI$_4$.

The term "tetrafluoroborate" describes a —BF$_4$ group.

A "tetrafluoroantimonate" is a SbF$_6$ group.

A "hypophosphite" is a —P(OH)$_2$ group.

The term "metaborate" describes the group

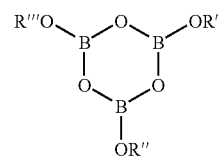

where R', R" and R''' are as defined hereinabove.

The terms "tetraalkyl/tetraaryl borate" describe a R'B⁻ group, with R' being an alkyl or an aryl, respectively, as defined above.

A "tartarate" is an —OC(=O)—CH(OH)—CH(OH)—C(=O)OH group.

A "salycilate" is the group

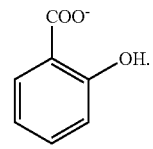

A "succinate" is an —O—C(=O)—(CH$_2$)$_2$—COOH group.

A "citrate" is an —O—C(=O)—CH$_2$—CH(OH)(COOH)—CH$_2$—COOH group.

An "ascorbate" is the group

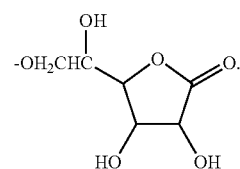

A "saccharirate" is an oxidized saccharide having two carboxylic acid group.

The term "amino acid" as used herein includes natural and modified amino acids and hence includes the 21 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

A "hydroxamic acid" is a —C(=O)—NH—OH group.
A "thiotosylate" is the group

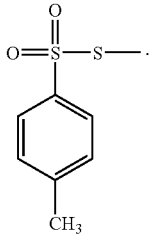

Similarly, each of the alkylene chains $B_1 \ldots Bn$ independently has a general formula III:

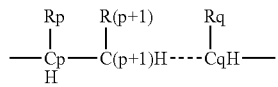

Formula III wherein p is an integer that equals 0 or g+1 and q is an integer from g+2 to g+20.

Hence, each of the alkylene chains $B_1 \ldots Bn$ is comprised of a plurality of carbon atoms Cp, Cp+1, Cp+2 ..., Cq−1 and Cq, substituted by the respective Rp, Rp+1, Rp+2 ..., Rq−1 and Rq groups. Preferably, each of the alkylene chains $B_1 \ldots Bn$ includes 2-20 carbon atoms, more preferably 2-10, and most preferably 2-6 carbon atoms.

As is defined hereinabove, in cases where p equals 0, the component —CpH(Rp)— is absent from the structure. In cases where p equals g+1, it can be either 1 or 4-11. The integer q can be either 2 or 5-20.

Each of the substituents Rp, Rp+1 ... Rn can be any of the substituents described hereinabove with respect to $R_1$, $R_2$ and Rg.

Hence, a preferred linear polyamine according to the present invention includes two or more alkylene chains. The alkylene chains are interrupted therebetween by a heteroatom and each is connected to a heteroatom at one end thereof. Preferably, each of the alkylene chains include at least two carbon atoms, so as to enable the formation of a stable chelate between the heteroatoms and the copper ion.

The linear polyamine delineated in Formula I preferably includes at least one chiral carbon atom. Hence, at least one of $C_1$, $C_2$ and Cg in the alkylene chain A and/or at least one of Cp, Cp+1 and Cq in the alkylene chain B is chiral.

A preferred linear polyamine according to the present invention is tetraethylenepentamine. Other representative examples of preferred linear polyamines usable in the context of the present invention include, without limitation, ethylendiamine, diethylenetriamine, triethylenetetramine, triethylenediamine, aminoethylethanolamine, pentaethylenehexamine, triethylenetetramine, N,N'-bis(3-aminopropyl)-1,3-propanediamine, and N,N'-Bis(2-animoethyl)-1,3 propanediamine.

In cases where the polyamine chelator is a cyclic polyamine, the polyamine can have a general formula IV:

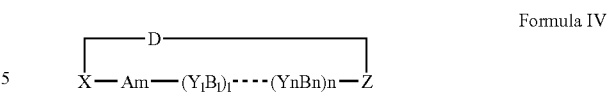

Formula IV wherein m is an integer from 1 to 10; n is an integer from 0 to 20; X and Z are each independently selected from the group consisting of an oxygen atom, a sulfur atom and a —NH group; $Y_1$ and Yn are each independently selected from the group consisting of an oxygen atom, a sulfur atom and a —NH group; A is an alkylene chain having between 1 and 10 substituted and/or non-substituted carbon atoms; $B_1$ and Bn are each independently an alkylene chain having between 1 and 20 substituted and/or non-substituted carbon atoms; and D is a bridging group having a general formula V:

Formula V whereas U and V are each independently selected from the group consisting of substituted hydrocarbon chain and non-substituted hydrocarbon chain; and W is selected from the group consisting of amide, ether, ester, disulfide, thioether, thioester, imine and alkene, provided that at least one of said X, Z, $Y_1$ and Yn is a —NH group and/or at least one of said carbon atoms in said alkylene chains is substituted by an amine group.

Optionally, the cyclic polyamine has one of the general formulas VI-X:

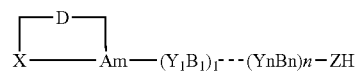

Formula VI

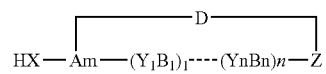

Formula VII

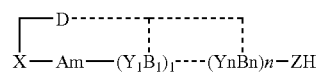

Formula VIII

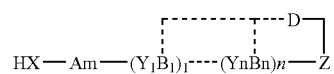

Formula IX

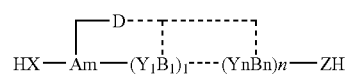

Formula X wherein m, n, X, $Y_1$, Yn, Z, A, B and D are as described above and further wherein should the bridging group D is attached at one end to A (Formulas VI, VII and X), U or V are being attached to one carbon atom in the alkylene chain and should D is attached at one end to B1 or Bn (Formulas VIII, IX and X), U or V are being attached to one carbon atom in the alkylene chain.

Hence, a preferred cyclic polyamine according to the present invention includes two or more alkylene chains, A, $B_1 \ldots Bn$, as is detailed hereinabove with respect to the linear polyamine. The alkylene chains can form a cyclic structure by being connected, via the bridging group D, between the ends thereof, namely between the heteroatoms X and Z (Formula IV). Optionally, the alkylene chains can form a conformationally restricted cyclic structure by being connected, via the bridging group D, therebetween (Formula X). Further optionally, a conformationally restricted cyclic structure can be formed by connecting one alkylene chain to one terminal heteroatom (X or Z, Formulas VI-IX).

As is described hereinabove, in cases where the cyclic structure is formed by connecting one alkylene chain to one terminal heteroatom, as is depicted in Formulas VI-IX, the bridging group D connects a terminal heteroatom, namely X or Z, and one carbon atom in the alkylene chains A and $B_1 \ldots Bn$. This carbon atom can be anyone of $C_1$, $C_2$, Cg, Cp, Cp+1 and Cq described hereinabove.

As is further described hereinabove, the cyclic structure is formed by the bridging group D, which connects two components in the structure. The bridging group D has a general formula U—W—V, where each of U and V is a substituted or non-substituted hydrocarbon chain.

As used herein, the phrase "hydrocarbon chain" describes a plurality of carbon atoms which are covalently attached one to another and are substituted, inter alia, by hydrogen atoms. The hydrocarbon chain can be saturated, unsaturated, branched or unbranched and can therefore include one or more alkyl, alkenyl, alkynyl, cycloalkyl and aryl groups and combinations thereof.

The length of the hydrocarbon chains, namely the number of carbon atoms in the chains, is preferably determined by the structure of the cyclic polyamine, such that on one hand, the ring tension of the formed cyclic structure would be minimized and on the other hand, an efficient chelation with the copper ion would be achieved.

When the hydrocarbon chain is substituted, the substituents can be any one or combinations of the substituents described hereinabove with respect to $R_1$, $R_2$ and Rg in the linear polyamine.

The two hydrocarbon chains are connected therebetween by the group W, which can be amide, ether, ester, disulfide, thioether, thioester, imine and alkene.

As used herein, the term "ether" is an —O— group.

The term "ester" is a —C(=O)—O— group.

A "disulfide" is a —S—S— group.

A "thioether" is a —S— group.

A "thioester" is a —C(=O)—S— group.

An "imine" is a —C(=NH)— group.

An "alkene" is a —CH=CH— group.

The bridging group D is typically formed by connecting reactive derivatives of the hydrocarbon chains U and V, so as to produce a bond therebetween (W), via well-known techniques, as is described, for example, in U.S. Pat. No. 5,811,392.

As is described above with respect to the linear polyamine, the cyclic polyamine must include at least one amine group, preferably at least two amine groups and more preferably at least four amine groups, so as to form a stable copper chelate.

A preferred cyclic polyamine according to the present invention is cyclam (1,4,8,11-tetraazacyclotetradecane).

As is described hereinabove, the polyamine chelator of the present invention can further include a multimeric combination of one or more linear polyamine(s) and one or more cyclic polyamine(s). Such a polyamine chelator can therefore be comprised of any combinations of the linear and cyclic polyamines described hereinabove.

Preferably, such a polyamine chelator has a general Formula XI:

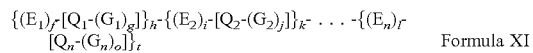

Formula XI wherein n is an integer greater than 1; each of f, g, h, i, j, k, l, o and t is independently an integer from 0 to 10; each of $E_1$, $E_2$ and En is independently a linear polyamine, as is described hereinabove; each of $G_1$, $G_2$ and Gn is independently a cyclic polyamine as is described hereinabove; and each of $Q_1$, $Q_2$ and Qn is independently a linker linking between two of said polyamines, provided that at least one of said $Q_1$, $Q_2$ and Qn is an amine group and/or at least one of said linear polyamine and said cyclic polyamine has at least one free amine group.

Each of $E_1$, $E_2$ and En in Formula XI represent a linear polyamine as is described in detail hereinabove, while each of $G_1$, $G_2$ and Gn represents a cyclic polyamine as is described in detail hereinabove.

The polyamine described in Formula XI can include one or more linear polyamine(s), each connected to another linear polyamine or to a cyclic polyamine.

Each of the linear or cyclic polyamines in Formula XI is connected to another polyamine via one or more linker(s), represented by $Q_1$, $Q_2$ and Qn in Formula XI.

Each of the linker(s) $Q_1$, $Q_2$ and Qn can be, for example, alkylene, alkenylene, alkynylene, arylene, cycloalkylene, hetroarylene, amine, azo, amide, sulfonyl, sulfinyl, sulfonamide, phosphonyl, phosphinyl, phosphonium, ketoester, carbonyl, thiocarbonyl, ester, ether, thioether, carbamate, thiocarbamate, urea, thiourea, borate, borane, boroaza, silyl, siloxy and silaza.

As used herein, the term "alkenylene" describes an alkyl group which consists of at least two carbon atoms and at least one carbon-carbon double bond.

The term "alkynylene" describes an alkyl group which consists of at least two carbon atoms and at least one carbon-carbon triple bond.

The term "cycloalkylene" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane.

The term "arylene" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroarylene" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

As used in the context of the linker of the present invention, the term "amine" describes an —NR'—, wherein R' can be hydrogen, alkyl, cycloalkyl, aryl, heteroaryl or heterocyclic, as these terms are defined hereinabove.

As is further used in the context of the linker of the present invention, the term "azo" describes a —N=N— group.

The term "amide" describes a —C(=O)—NR'— group, where R' is as defined hereinabove.

The term "ammonium" describes an —N⁺HR'— group, where R' is as defined hereinabove.

The term "sulfinyl" describes a —S(=O)— group.

The term "sulfonyl" describes a —S(=O)$_2$— group.

The term "sulfonamido" describes a —S(=O)$_2$—NR'— group, with R' as defined hereinabove.

The term "phosphonyl" describes a —O—P(=O)(OR')— group, with R' as defined hereinabove.

The term "phosphinyl" describes a —PR'— group, with R' as defined hereinabove.

The term "phosphonium" is a —P$^+$R'R", where R' and R" are as defined hereinabove.

The term "ketoester" describes a —C(=O)—C(=O)—O— group.

The term "carbonyl" describes a —C(=O)— group.

The term "thiocarbonyl" describes a —C(=S)— group.

The term "carbamate" describes an —OC(=O)—NR'— group, with R' as defined hereinabove.

The term "thiocarbamate" describes an —OC(=S)—NR— group, with R' as defined hereinabove.

The term "urea" describes an —NR'—C(=O)—NR"— group, with R' and R" and as defined hereinabove.

The term "thiourea" describes a —NR'—C(=S)—NR'— group, with R' and R" as defined hereinabove.

The term "borate" describes an —O—B—(OR)— group, with R as defined hereinabove.

The term "borane" describes a —B—R—'— group, with R as defined hereinabove.

The term "boraza" describes a —B(NR'R")— group, with R' and R" as defined hereinabove.

The term "silyl" describes a —SiR'R"—, with R' and R" as defined herein.

The term "siloxy" is a —Si—(OR)$_2$—, with R as defined hereinabove.

The term "silaza" describes a —Si—(NR'R")$_2$—, with R' and R" as defined herein.

It should be noted that all the terms described hereinabove in the context of the linker of the present invention are the same as described above with respect to the substituents. However, in distinction from the substituent groups, which are connected to a component at one end thereof, the linker groups are connected to two components at two sites thereof and hence, these terms have been redefined with respect to the linker.

As has been mentioned hereinabove, according to the presently most preferred embodiment of the present invention, the polyamine chelator is tetraethylenepentamine (TEPA). However, other preferred polyamine chelators include, without limitation, ethylendiamine, diethylenetriamine, triethylenetetramine, triethylenediamine, aminoethylethanolamine, aminoethylpiperazine, pentaethylenehexamine, triethylenetetramine, captopril, penicilamine, N,N'-bis(3-aminopropyl)-1,3-propanediamine, N,N'-Bis(2-animoethyl)-1,3-propanediamine, 1,7-dioxa-4,10-diazacyclododecane, 1,4,8,11-tetraazacyclotetradecane-5,7-dione, 1,4,7-triazacyclononane, 1-oxa-4,7,10-triazacyclododecane, 1,4,8,12-tetraazacyclopentadecane and 1,4,7,10-tetraazacyclododecane.

The above listed preferred chelators are known in their high affinity towards copper ions. However, these chelators are further beneficially characterized by their substantial affinity also towards other transition metals, as is described by Ross and Frant [22], which is incorporated by reference as if fully set forth herein.

All the polyamine chelators described hereinabove can be either commercially obtained or can be synthesized using known procedures such as described, for example, in: T. W. Greene (ed.), 1999 ("Protective Groups in Organic Synthesis" 3ed Edition, John Wiley & Sons, Inc., New York 779 pp); or in: R. C. Larock and V. C. H. Wioley, "Comprehensive Organic Transformations—A Guide to Functional Group Preparations", (1999) 2$^{nd}$ Edition.

A preferred procedure for preparing tetraethylenepentamine-copper chelate (TEPA-Cu) is described in Example 1 of the Examples section which follows.

The copper chelate can be provided to the cell culture medium. The final concentrations of copper chelate may be, depending on the specific application, in the micromolar or millimolar ranges, for example, within about 0.1 µM to about 100 mM, preferably within about 4 µM to about 50 mM, more preferably within about 5 µM to about 40 mM. As is described hereinabove, the copper chelate is provided to the cells so as to maintain the free copper concentration of the cells substantially unchanged during cell expansion.

As is described hereinabove, the methods according to the aspects and embodiments depicted hereinabove, as well as other methods and embodiments of other aspects of the present invention, as is detailed hereinbelow, are effected by providing the ex-vivo grown cells with conditions for cell proliferation. Such providing typically includes providing the cells with nutrients and with one or more cytokines. Methods of ex vivo culturing of stem cells of different tissue origins are well known in the art of cell culturing (see, for example, in the text book: Feshney, Wiley-Liss N. Y. "Culture of Animal Cells—A manual of Basic Techniques", (1994) 3$^{rd}$ Edition).

Nutrients provided to ex vivo grown cells include, for example, alpha minimal essential medium supplemented with 10% fetal bovine serum (FBS, Biological Industries).

The cytokines provided to ex-vivo grown cells, can be early- or late-acting cytokines. Early-acting cytokines can be, according to a preferred embodiment of this invention, stem cell factor, FLT3 ligand, interleukin-6, thrombopoietin and interleukin-3. Late-acting cytokines can be, according to another preferred embodiment of this invention, granulocyte colony stimulating factor, granulocyte/macrophage colony stimulating factor and erythropoietin. All these cytokines are commercially available, for example, from Perpo Tech, Inc., Rocky Hill, N.J.

The stem and/or progenitor cells, used for cell expansion in the context of these and other aspects and embodiments of the present invention, can be obtained from any tissue of any multicellular organism including both animals and plants. It is known in the art that stem cells exist in many organs and tissues and are believed to exist in all tissues of animals, including, but not limited to, bone marrow, peripheral blood, and neonatal umbilical cord blood.

The stem or progenitor cells may be of any cell lineage including, but not limited to, hematopoietic stem or progenitor cells, neural stem or progenitor cells, oligodendrocyte stem or progenitor cells, skin stem or progenitor cells, hepatic stem or progenitor cells, muscle stem or progenitor cells, bone stem or progenitor cells, mesenchymal stem or progenitor cells, pancreatic stem or progenitor cells, chondrocyte stem or progenitor cells, or stroma stem or progenitor cells.

The stem or progenitor cells can be embryonic stem cells or adult stem cells. Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). Adult stem cells are stem cells, which are derived from tissues of adults and are also well known in the art. Methods of isolating or enriching for adult stem cells are described in, for example, Miraglia, S. et al. (1997) Blood 90: 5013, Uchida, N. et al. (2000) Proc. Natl. Acad. Sci. USA 97: 14720, Simmons, P. J. et al. (1991) Blood 78: 55, Prockop D J (Cytotherapy (2001) 3: 393), Bohmer R M (Fetal Diagn Ther (2002) 17: 83) and Rowley S D et al (Bone Marrow Transplant (1998) 21: 1253), Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000). A presently preferred source for adult stem cells is the hematopoietic system.

According to a presently preferred embodiment of the present invention the stem cells are hematopoietic stem cells. Such stem cells can be derived from bone marrow, peripheral blood and neonatal umbilical cord blood. Methods of enriching white blood cells (mononuclear cells) for stem cells are well known in the art, and include, for example, selecting $CD34^+$ expressing cells. $CD34^+$ cells include pluripotent stem cells and very early progenitor cells, which, under the appropriate conditions may revert to stem cells, as they are not lineage committed cells.

According to another aspect of the present invention there is provided a method of hematopoietic cells transplantation. The method is effected by (a) obtaining from a donor hematopoietic cells to be transplanted; (b) providing the hematopoietic cells ex-vivo with conditions for cell proliferation and with an effective amount of at least one copper chelate, so as to maintain a free copper concentration available to the cells substantially unchanged, to thereby expand the population of the cells, while at the same time, reversibly inhibit differentiation of the hematopoietic cells; and (c) transplanting the hematopoietic cells in a patient.

According to yet another aspect of the present invention, there is provided another method of hematopoietic cells transplantation. The method according to this aspect of the present invention is effected by (a) obtaining from a donor hematopoietic cells to be transplanted; (b) providing at least one copper chelate; and thereafter (c) mixing an effective amount of the copper chelate(s) with the hematopoietic cells and with a cell growth medium, so as to keep substantially unchanged by this mixing a free copper concentration in the cell growth medium, to thereby expand the population of the hematopoietic cells, while at the same time reversibly inhibit differentiation of the hematopoietic cells; and (d) transplanting the hematopoietic cells in a patient.

The expanded cells can be administered in a pharmaceutically acceptable carrier or diluent, such as sterile saline or aqueous buffer solutions. The use of such carriers and diluents is well known in the art. The cells may be obtained from peripheral blood, bone marrow or neonatal umbilical cord blood. They are preferably enriched with stem cells or with progenitor cells (e.g., by cell sorting) prior to, and/or after, cell expansion. The donor and the recipient can be the same individual (in autologous transplantation) or different individuals, such as, for example, allogenic individuals (in allogenic transplantation). When allogenic transplantation is practiced, regimes for reducing implant rejection and/or graft vs. host disease, which are well known in the art, should be undertaken. Such regimes are currently practiced in human therapy. Most advanced regimes are described in: Slavin S. et al., J. Clin. Immunol. (2002) 22:64; Slavin S. et al., J. Hematother Stem Cell Res. (2002) 11:265; Gur H. et. al., Blood (2002) 99:4174; Martelli M. F. et al., and Hematol (2002) 39:48, which are incorporated herein by reference.

As is further detailed below, stem cells may serve to exert cellular gene therapy.

Gene therapy as used herein refers to the transfer of genetic material (e.g., DNA or RNA) of interest into a host, in order to treat or prevent a genetic or acquired disease, condition or phenotype. The genetic material of interest encodes a product (e.g., a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (i) ex-vivo or cellular gene therapy; and (ii) in vivo gene therapy. In ex-vivo gene therapy cells are removed from a patient and, while being cultured, are treated in-vitro. Generally, a functional replacement gene is introduced into the cells via an appropriate gene delivery vehicle/method (transfection, transduction, homologous recombination, etc.) and an expression system as needed and then the modified cells are expanded in culture and returned to the host/patient. These genetically re-implanted cells have been shown to express the transfected genetic material in situ.

Hence, according to still another aspect of the present invention, there is provided a method of genetically modifying stem cells with an exogene (i.e., transgene). The method according to this aspect of the present invention is effected by (a) obtaining stem cells to be genetically modified; (b) providing the stem cells ex-vivo with conditions for cell proliferation and, at the same time, administering the stem cells with an effective amount of at least one copper chelate, so as to maintain a free copper concentration available to the cells substantially unchanged, to thereby expand the population of the stem cells, while at the same time reversibly inhibit differentiation thereof; and (c) genetically modifying the stem cells with the exogene.

According to an additional aspect of the present invention, there is provided another method of genetically modifying stem cells with an exogene. This method is effected by (a) obtaining stem cells to be genetically modified; (b) providing at least one copper chelate; and thereafter (c) mixing an effective amount of the copper chelate(s) with the stem cells and with a cell growth medium, so as to keep substantially unchanged by this mixing a free copper concentration in the cell growth medium, to thereby expand the population of the stem cells, while at the same time reversibly inhibit the differentiation thereof; and (d) genetically modifying the stem cells with the exogene.

In one embodiment of these aspects of the present invention, genetically modifying the cells is effected by a vector, which includes the exogene. The vector can be, for example, a viral vector or a nucleic acid vector. Many vectors, suitable for use in cellular gene therapy are known, examples of which are provided hereinbelow. Similarly, a range of nucleic acid vectors can be used to genetically transform the expanded cells of the invention as is further described below.

Accordingly, the expanded cells of the present invention can be modified to express a gene product. As used herein, the phrase "gene product" includes, without limitation, proteins, peptides and functional RNA molecules. Generally, the gene product encoded by the nucleic acid molecule is the desired gene product to be supplied to a subject. Examples of gene products include, without limitation proteins, peptides, glycoproteins and lipoproteins normally produced by an organ of the recipient subject. For example, gene products which may be supplied by way of gene replacement to defective organs in the pancreas include insulin, amylase, protease, lipase, trypsinogen, chymotrypsinogen, carboxypeptidase, ribonuclease, deoxyribonuclease, triaclyglycerol lipase, phospholipase $A_2$, elastase, and amylase; gene products normally produced by the liver include blood clotting factors such as blood clotting Factor VIII and Factor IX, UDP glucuronyl transferae, ornithine transcarbanoylase, and cytochrome p450 enzymes, and adenosine deaminase, for the processing of serum adenosine or the endocytosis of low density lipoproteins; gene products produced by the thymus include serum thymic factor, thymic humoral factor, thymopoietin, and thymosin $\alpha_1$; gene products produced by the digestive tract cells include gastrin, secretin, cholecystokinin, somatostatin, serotinin, and substance P.

Alternatively, the encoded gene product is a product that induces the expression of the desired gene product by the cell (e.g., the introduced genetic material encodes a transcription factor, which induces the transcription of the gene product to be supplied to the subject).

In still another embodiment of these aspects of the present invention, the recombinant gene can provide a heterologous protein, e.g., not native to the cell in which it is expressed. For instance, various human MHC components can be provided to non-human cells to support engraftment in a human recipient. Alternatively, the transgene is a gene that inhibits the expression or action of a donor MHC gene product normally expressed in the micro-organ explant.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene acid molecule include promoters, enhancers and polyadenylation signals, as well as sequences necessary for transport of an encoded protein or peptide, such as N-terminal signal sequences for transport of proteins or peptides to the surface of the cell or secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements, which are known in the art, include upstream regions from the dystrophin gene (Klamut et al., (1989) *Mol. Cell Biol*.9: 2396), the creatine kinase gene (Buskin and Hauschka, (1989) *Mol. Cell Biol*. 9: 2627) and the troponin gene (Mar and Ordahl, (1988) *Proc. Natl. Acad. Sci. USA*. 85: 6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters).

Alternatively, a regulatory element, which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs.

Alternatively, a regulatory element, which provides inducible expression of a gene linked thereto, can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S. and White, J. H. (1993) *Proc. Natl. Acad. Sci. USA* 90: 5603-5607), synthetic ligand-regulated elements (see, e.g., Spencer, D. M. et al 1993) *Science* 262: 1019-1024) and ionizing radiation-regulated elements (e.g., see Manome, Y. Et al. (1993) *Biochemistry* 32: 10607-10613; Datta, R. et al. (1992) *Proc. Natl. Acad. Sci. USA* 89: 1014-10153). Additional tissue-specific or inducible regulatory systems, which may be developed, can also be used in accordance with the invention.

There are number of techniques known in the art for introducing genetic material into a cell, which can be applied to modify a cell according to the present invention.

In one embodiment, the nucleic acid is in the form of a naked nucleic acid molecule. In this situation, the nucleic acid molecule introduced into a cell to be modified consists only of the nucleic acid encoding the gene product and the necessary regulatory elements.

Alternatively, the nucleic acid encoding the gene product (including the necessary regulatory elements) is contained within a plasmid vector. Examples of plasmid expression vectors include CDM8 (Seed, B. (1987) *Nature* 329: 840) and pMT2PC (Kaufman, et al. (1987) *EMBO J*. 6: 187-195).

In another embodiment, the nucleic acid molecule to be introduced into a cell is contained within a viral vector. In this situation, the nucleic acid encoding the gene product is inserted into the viral genome (or partial viral genome). The regulatory elements directing the expression of the gene product can be included with the nucleic acid inserted into the viral genome (i.e., linked to the gene inserted into the viral genome) or can be provided by the viral genome itself.

Naked nucleic acids can be introduced into cells using calciumphosphate mediated transfection, DEAE-dextran mediated transfection, electroporation, liposome-mediated transfection, direct injection, and receptor-mediated uptake.

Naked nucleic acid, e.g., DNA, can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in Current Protocols in Molecular Biology, Ausubel, F. M., et al. (eds.) Greene Publishing Associates, (1989), Section 9.1 and in Molecular Cloning: A Laboratory Manual, 2nd Edition, Sambrook et al. Cold Spring Harbor Laboratory Press, (1989), Sections 16.32-16.40 or other standard laboratory manuals.

Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce DNA transiently into cells but is not preferred for creating stably transfected cells. Thus, this method can be used for short-term production of a gene product but is not a method of choice for long-term production of a gene product. Protocols for DEAE-dextran-mediated transfection can be found in Current Protocols in Molecular Biology, Ausubel, F. M., et al. (eds.) Greene Publishing Associates (1989), Section 9.2 and in Molecular Cloning: A Laboratory Manual, 2nd Edition, Sambrook et al. Cold Spring Harbor Laboratory Press, (1989), Sections 16.41-16.46 or other standard laboratory manuals.

Naked nucleic acid can also be introduced into cells by incubating the cells and the nucleic acid together in an appropriate buffer and subjecting the cells to a high-voltage electric pulse. The efficiency, with which nucleic acid is introduced into cells by electroporation, is influenced by: the strength of the applied field, the length of the electric pulse, the temperature, the conformation and concentration of the DNA and the ionic composition of the media. Electroporation can be used to stably (or transiently) transfect a wide variety of cell types and is only applicable to in vitro modification of cells. Protocols for electroporating cells can be found in Current Protocols in Molecular Biology, Ausubel F. M., et al. (eds.) Greene Publishing Associates, (1989), Section 9.3 and in Molecular Cloning: A Laboratory Manual, 2nd Edition, Sambrook et al. Cold Spring Harbor Laboratory Press, (1989), Sections 16.54-16.55 or other standard laboratory manuals.

Another method by which naked nucleic acid can be introduced into cells includes liposome-mediated transfection (lipofection). The nucleic acid is mixed with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel, F. M., et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157-176; Wang and Huang (1987) *Proc. Natl. Acad. Sci. USA* 84:7851-7855; Brigham et al. (1989) *Am. J Med. Sci.* 298:278; and Gould-Fogerite et al. (1989) *Gene* 84:429-438.

Naked nucleic acid can also be introduced into cells by directly injecting the nucleic acid into the cells. For an in vitro culture of cells, DNA can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the DNA is stably introduced into a fertilized oocyte, which is then allowed to develop into an animal. The resultant animal contains cells carrying the DNA introduced into the oocyte. Direct injection has also been used to introduce naked DNA into cells in vivo (see e.g., Acsadi et al. (1991) *Nature* 332:815-818; Wolff et al. (1990) *Science* 247:1465-1468). A delivery apparatus (e.g., a "gene gun") for injecting DNA into cells in vivo can be used. Such an apparatus is commercially available (e.g., from BioRad).

Naked nucleic acid can be complexed to a cation, such as polylysine, which is coupled to a ligand for a cell-surface receptor to be taken up by receptor-mediated endocytosis (see for example Wu, G. and Wu, C. H. (1988) *J. Biol. Chem.* 263: 14621; Wilson et al. (1992) *J. Biol. Chem.* 267: 963-967; and U.S. Pat. No. 5,166,320). Binding of the nucleic acid-ligand complex to the receptor facilitates uptake of the DNA by receptor-mediated endocytosis. Receptors to which a DNA-ligand complex has targeted include the transferrin receptor and the asialoglycoprotein receptor. A DNA-ligand complex linked to adenovirus capsids which naturally disrupt endosomes, thereby releasing material into the cytoplasm, can be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90: 2122-2126). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Generally, when naked DNA is introduced into cells in culture (e.g., by one of the transfection techniques described above) only a small fraction of cells (about 1 out of $10^5$) typically integrate the transfected DNA into their genomes (i.e., the DNA is maintained in the cell episomally). Thus, in order to identify cells, which have taken up exogenous DNA, it is advantageous to transfect nucleic acid encoding a selectable marker into the cell along with the nucleic acid(s) of interest. Preferred selectable markers include those, which confer resistance to drugs such as G418, hygromycin and methotrexate. Selectable markers may be introduced on the same plasmid as the gene(s) of interest or may be introduced on a separate plasmid.

A preferred approach for introducing nucleic acid encoding a gene product into a cell is by use of a viral vector containing nucleic acid, e.g., a cDNA, encoding the gene product. Infection of cells with a viral vector has the advantage that a large proportion of cells receive the nucleic acid which can obviate the need for selection of cells which have received the nucleic acid. Additionally, molecules encoded within the viral vector, e.g., a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for review see Miller, A. D. (1990) *Blood* 76: 271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions, which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M., et al. (eds.) Greene Publishing Associates, (1989), Sections 9.10-9.14; and other standard laboratory manuals. Examples of suitable retroviruses include pLJ, pZIP, pWE and pEM, which are well known to those skilled in the art. Examples of suitable packaging virus lines include ψCrip, ψCrip, ψ2 and ψAm. Retroviruses have been used to introduce a variety of genes into many different cell types, including epithelial cells endothelial cells, lymphocytes, myoblasts, hepatocytes, bone marrow cells, in vitro and/or in vivo (see for example Eglitis, et al. (1985) Science 230: 1395-1398; Danosand Mulligan (1988) *Proc. Natl. Acad. Sci. USA* 85: 6460-6464; Wilson et al. (1988) *Proc. Natl. Acad. Sci USA* 85:3014-3018; Armentano et al., (1990) Proc. Natl. Acad. Sci. USA 87: 6141-6145; Huber et al. (1991) Proc. Natl. Acad. Sci. USA 88: 8039-8043; Feri et al. (1991) Proc. Natl. Acad. Sci. USA 88:8377-8381; Chowdhury et al. (1991) *Science* 254: 1802-1805; van Beusechem et al. (1992) Proc. Natl. Acad. Sci USA 89:7640-7644; Kay et al. (1992) *Human Gene Therapy* 3:641-647; Dai et al. (1992) *Proc. Natl. Acad. Sci. USA* 89:10892-10895; Hwu et al (1993) J. Immunol. 150: 4104-4115; U.S. Pat. No. 4,868,116; U.S. Pat. No. 4,980, 286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

The genome of an adenovirus can be manipulated such that it encodes and expresses a gene product of interest but is inactivated in terms of its ability to replicate in a normal lytic viral life cycle. See for example Berkner et al. (1988) BioTechniques 6:616; Rosenfeld et al. (1991) Science 252: 431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89: 6482-6486), hepatocytes (Herz and Gerard (1993) Proc. Natl. Acad. Sci. USA 90: 2812-2816) and muscle cells (Quantin et al. (1992) Proc. Natl. Acad. Sci. USA 89: 2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra, Haj-Ahmand and Graham (1986) J. Virol 57: 267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle (For a review see Muzyczka et al. Curr. Topics In Micro. And Immunol. (1992) 158: 97-129). It is also one of the few viruses that may integrate its DNA into non-dividing cells, and exhibits a high frequency of stable integration (see for example Flotte et al. (1992) Am. J. Respir. Cell. Mol. Biol. 7: 349-356; Samulski et al. (1989) J. Virol. 63:3822-3828; and McLaughlin et al (1989) J. Virol. 62: 1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5: 3251-3260 can be used to introduce DNA into cells. A variety of nucleic acids have been introduced into different cell types using AAV vectors (see for example Hermonat et al. (1984) Proc. Natl. Acad. Sci. USA 81: 6466-6470; Tratschin et al. (1985) Mol. Cell Biol. 4: 2072-2081; Wondisford et al. (1988) Mol. Endocrinol. 2:32-39; Tratschin et al. (1984) J. Virol. 51: 611-619; and Flotte et al. (1993) J. Biol. Chem. 268: 3781-3790).

The efficacy of a particular expression vector system and method of introducing nucleic acid into a cell can be assessed by standard approached routinely used in the art. For example, DNA introduced into a cell can be detected by a filter hybridization technique (e.g., Southern blotting) and RNA produced by transcription of introduced DNA can be detected, for example, by:

Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone.

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells, which efficiently express the gene product. Such a population of uniform cells can be prepared by isolating a single modified cell by limiting dilution cloning followed by expanding the single cell in culture into a clonal population of cells by standard techniques.

The copper chelates and methods of cell expansion of the present invention can be further utilized for adoptive immunotherapy.

Hence, according to yet an additional aspect of the present invention, there is provided a method of adoptive immunotherapy. The method according to this aspect of the present invention is effected by (a) obtaining progenitor hematopoietic cells from a patient; (b) providing the hematopoietic cells ex-vivo with conditions for cell proliferation and with an effective amount of at least one copper chelate, so as to maintain a free copper concentration available to the cells substantially unchanged, to thereby expand the progenitor hematopoietic cells, while at the same time reversibly inhibit differentiation of the hematopoietic cells; and (c) transplanting the progenitor hematopoietic cells in the patient.

According to still an additional aspect of the present invention, there is provided another method of adoptive immunotherapy. This method is effected by (a) obtaining progenitor hematopoietic cells from a patient; (a) providing at least one copper chelate; and thereafter (c) mixing an effective amount of the copper chelate(s) with the progenitor hematopoietic cells and with a cell growth medium, so as to keep substantially unchanged by this mixing a free copper concentration in the cell growth medium, to thereby expand the population of progenitor hematopoietic cells, while at the same time reversibly inhibit the differentiation thereof; and (d) transplanting the progenitor hematopoietic cells to the patient.

The effect of copper chelates used in context of the present invention is not limited to ex vivo settings. Hence, based on the findings herein described, novel in vivo applications for these copper chelates are envisaged.

Hence, according to a further aspect of the present invention, there is provided a method of in vivo expanding a population of stem and/or progenitor cells, while at the same time reversibly inhibiting differentiation of the stem and/or progenitor cells. The method according to this aspect of the present invention is effected by administrating to a subject in need thereof a therapeutically effective amount of at least one copper chelate, so as to keep substantially unchanged by this administrating a free copper concentration of the subject, to thereby expand the population of the stem and/or progenitor cells, while at the same time reversibly inhibit the differentiation thereof.

Another in vivo application of the copper chelates of the present invention concern the mobilization of bone marrow stem cells. Hence, according to still a further aspect of the present invention there is provided a method of mobilization of bone marrow stem cells into the peripheral blood of a donor for harvesting the bone marrow stem cells. The method according to this aspect of the present invention is effected by administering to the donor an effective amount of at least one copper chelate, so as to in vivo expand the bone marrow stem cells, while at the same time reversibly inhibit the differentiation thereof, followed by harvesting the bone marrow stem cells by leukapheresis. Administering to the donor a cytokine (early and/or late acting cytokine), so as to enhance mobilization, is preferable.

The copper chelates of the present invention can be further utilized in the treatment of β-hemoglobinopathic patients, such that according to another aspect of the present invention there is provided a method of decelerating maturation/differentiation of erythroid precursor cells for the treatment of β-hemoglobinopathic patients. The method according to this aspect of the present invention is effected by administering to a patient in need thereof an effective amount of at least one copper chelate, so as to in vivo expand the population of the erythroid precursor cells, while at the same time reversibly inhibit the differentiation thereof. This treatment increases and synchronizes the patient's early erythroid progenitor pool (by blocking differentiation). Following cessation of administration of the copper chelate and its removal from the body, this early population then might undergo accelerated maturation which results in elevated production of fetal hemoglobin.

In in vivo settings, the administration of the copper chelates of the present invention is typically effected by a pharmaceutical composition.

Hence, further according to another aspect of the present invention there is provided a pharmaceutical composition that comprises at least one copper chelate and a pharmaceutical acceptable carrier. Preferably, the pharmaceutical composition is packaged in a container and is identified in print on or in the container, for use in treatment of a medical condition in which stem and/or progenitor cell depletion is evident, such as, but not limited to, following bone marrow transplantation, chemo- and radio-therapy of solid tumors and plastic anemia. The pharmaceutical composition may further include thickeners, buffers, diluents, surface active agents, preservatives, and the like, all as well known in the art.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, intramuscular or intravenous injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates. Slow release administration regime may be advantageous in some applications.

The methods of ex vivo expanding the population of stem and/or progenitor cells evidently result in ex vivo expanded population of these cells. Hence, according to further aspects of the present invention, there are provided ex vivo expanded populations of stem and/or progenitor cells. The expanded populations of stem and/or progenitor cells are obtained either by providing harvested stem and/or progenitor cells with conditions for cell proliferation and with an effective amount of at least one copper chelate, so as to maintain a free copper concentration available to the cells substantially unchanged, or by first providing at least one copper chelate; and thereafter mixing an effective amount of the copper chelate(s) with harvested stem and/or progenitor cells and with a cell growth medium, so as to keep substantially unchanged by this m mixing a free copper concentration in the cell growth medium.

According to still another aspect of the present invention there is provided a method of preservation of stem cells, such as, but not limited to, cord blood derived stem cells, peripheral blood derived stem cells and bone marrow-derived stem cells. The method according to this aspect of the invention is effected by supplementing the stem cells, while being harvested, isolated and stored, with an effective amount of copper chelate, such as, but not limited to, TEPA-Cu.

According to an additional aspect of the present invention there is provided a kit for the collection and/or culturing of stem and/or progenitor cells. The kit comprises a container, such as a tissue-culture plate or a bag, which includes a growth medium supplemented with an effective amount of a copper chelate, which substantially inhibits differentiation of the stem and/or progenitor cells. The kit further comprises a packaging material identifying the kit for use in the collecting and/or culturing said stem and/or progenitor cells.

According to yet an additional aspect of the present invention there is provided an assay of determining whether a transition metal chelate causes inhibition or induction of differentiation. The assay comprises culturing a population of stem or progenitor cells or cells of a substantially non-differentiated cell line, in the presence of the transition metal chelate and monitoring differentiation of the cells, wherein if differentiation is increased as is compared to non-treated cells, the transition metal chelate induces differentiation, and further whereas if differentiation is decreased as compared to non-treated cells, or if differentiation is absent altogether, the transition metal chelate inhibits differentiation. Preferably, stem cells are cultured as described in Example 1 of the Examples section that follows. Briefly, purified $CD_{34}^+$ cells are seeded in Cell Culture Clusters (Corning), which contain growth medium, such as alpha medium supplemented with 10% fetal bovine serum (Biological Industries), and cytokines. The cell cultures are then supplemented with the tested transitional metal chelate and incubated at 37° C. at room temperatures for 3 to 8 weeks and comparatively scored for density of stem and/or progenitor cells and CFUs.

It is well accepted in the art that purification of $CD_{34}^+$ or $AC133^+$ is an essential pre-requisite for ex vivo expansion of stem or progenitor cells and that if the enrichment is not performed, prior to inoculation of cultures, no substantial expansion of stem/progenitor cells occurs [23-36].

Surprisingly, while reducing the present invention to practice, the inventors discovered that stem cells present in the mononuclear fraction of blood (i.e., mixed white blood cells), can undergo expansion if supplemented with copper chelate or chelator, in a similar fashion to cultures originated from enriched CD34+ stem cells.

Thus, according to another aspect of the present invention, there is provided another method of ex vivo expanding a population of stem and/or progenitor cells, while at the same time reversibly inhibiting differentiation of the stem and/or progenitor cells. This method is effected by first obtaining from a donor a mixed population of cells, which includes a certain amount of stem and/or progenitor cells. The mixed population of cells is then cultured ex vivo under conditions for proliferation of the stem and/or progenitor cells and with an effective amount of a copper chelate or chelator, to thereby expand the population of the stem and/or progenitor cells, while at the same time reversibly inhibit differentiation of the stem and/or progenitor cells.

The mixed population of cells is preferably obtained from a neonatal umbilical cord (CB), bone marrow, or peripheral blood. According to a preferred embodiment of this aspect of the present invention, stem and/or progenitor cells are expanded from the mononuclear fraction of CB, which is a whole fraction of white blood cells, and includes a mixture of stem, progenitor and committed cells. The mononuclear fraction of cells (MNC) is obtained by processing umbilical cord blood cells in Ficoll-Hypaque gradient (1.077 g/ml; Sigma) and centrifuge at 400 g for 30 minutes. The MNC is then collected from the resulting interface layer, washed and re-suspended in PBS containing 0.5% human serum albumin. The mixed cells culture may be seeded in culture bags (American Fluoroseal Corp) containing nutrient growth medium, such as alpha medium with 10% fetal bovine serum. The cell culture is also supplemented with early and/or late acting cytokines and with a copper chelate or chelator, preferably TEPA or TEPA-Cu, at a concentration that ranges between 5 μM and 20 μM. The mixed cell culture is preferably incubated at 37° C. in a humidified atmosphere of 5% $CO_2$, for 10-12 weeks.

Hence, the present invention provides methods of promoting proliferation while inhibiting differentiation of stem and progenitor cells, and expanded cell populations obtained thereby, via treating the cells with copper chelates. The copper chelates can be utilized both ex vivo and in vivo and can be applied in a variety of important clinical situations. In addition, the present invention provides methods of ex vivo expansion of stem and/or progenitor cells in cultures initiated by mixed hematopoietic cells, which can substantially simplify and reduce cost of producing stem and/or progenitor cells for therapeutic or other applications.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Cell Biology: A Laboratory Handbook" Volumes I-III Cellis, J. E., ed. (1994); "Current Protocols in Immunology" Volumes I-III Coligan J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods and Enzymology" Vol. 1-317 Academic Press; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Effects of TEPA-Cu Chelate on the Expansion of Stem and Progenitor Cells Ex Vivo Experimental Procedures Preparation of Tetraethylenepentamine (TEPA) and copper chelate: TEPA·5HCl (3 mmol, 1.1 gram, obtained from Sigma) was treated with a 15 ml solution of 1N NaOH in MeOH and centrifuged thereafter at 3,000 rpm for 5 minutes, so as to separate the NaCl precipitate. The remaining supernatant solution was diluted with 120 ml MeOH and a 30 ml aqueous solution of 3 mmol $CuCl_2$ was added thereto, forming a bright blue colored solution. The obtained solution was evaporated under vacuum at 25-30° C., re-suspended in about 100 ml MeOH, and evaporated under vacuum at 25-30° C., twice, in order to remove residual water. The residue was then dissolved in 15 ml isopropanol and the resulting NaCl precipitate was removed by filtration. The filtrate solution was thereafter diluted in 45 ml diethyl ether and re-crystallized at 8-10° C. for 2 weeks. The solution was then filtered out and the dark blue precipitate (recrystallized TEPA-Cu complex) was washed with 50 ml diethyl ether and dried under vacuum, yielding 0.74 grams of TEPA-Cu chelate. No traces of residual free copper were detected by FAB-MS analysis.

Sample collection and processing: Samples were obtained from umbilical human cord blood and processed within 12 hours. The blood cells were mixed with 3% Gelatin (Gigma, St. Louis, Mo.) and allowed to sediment for 30 minutes to remove most red blood cells. The leukocyte-rich fraction was harvested, layered on Ficoll-Hypaque (density 1.077 gram/ml; Sigma) and centrifuged at 400 g for 30 minutes at room temperature. The mononuclear cells in the interface layer were then collected, washed three times in phosphate-buffered saline (PBS; Biological Industries), and re-suspended in PBS solution which contains 1% bovine serum albumin (BSA; Sigma). The cells were then incubated at 4° C. for 30 minutes with murine monoclonal anti $CD_{34}^+$ antibody (0.5 μg/$10^6$ mononuclear cells) and were thereafter isolated using two cycles of immuno-magnetic separation using the miniMACS $CD_{34}^+$ Progenitor Cell Isolation Kit (Miltenyi-Biotec, Auburn, Calif.) according to the manufacturer's recommendations. The purity of the $CD_{34}^+$ cells obtained ranged between 95% and 98%, based on Flow Cytometry evaluation (see below).

Ex vivo expansion of progenitor cells: Enriched $CD_{34}^+$ cell fractions were cultures in 24-well Costar Cell Culture Clusters (Corning Inc., Corning, N.Y.) or in Culture Bags (American Fluoroseal Corp.) with alpha minimal essential medium supplemented with 10% fetal bovine serum (FBS, Biological Industries), at about 1-3×$10^4$ cells/ml medium. The media were further supplemented with the following human recombinant cytokines (all obtained from Perpo Tech, Inc., Rocky Hill, N.J.): Thrombopoietin (TPO), 50 ng/ml; interleukin 6 (IL-6), 50 ng/ml; FLT-3 ligand, 50 ng/ml; and IL-3, 20 ng/ml. The cultures were incubated at 37° C. in an atmosphere of 5% $CO_2$ in air with extra humidity. At weekly intervals cell cultures were semi-depopulated and supplemented with fresh medium containing the cytokines. Following different incubation periods, the cells were harvested, stained with trypan blue and enumerated. The total cell counts, numbers of $CD_{34}^+$ cells and subsets thereof, and the number of colony-forming cells (CFU) are presented herein as cumulative numbers, with the assumption that the cultures had not been passaged, namely, the numbers of cells per ml were multiplied by the number of passages performed.

Self-renewal potential evaluations: The self-renewal potential of stem cells was determined in vitro by long-term colony formation. Cells were washed and seeded in a semi-solid methylcellulose medium supplemented with 2 IU/ml erythropoietin (Eprex, Cilage AG Int., Switzerland), stem cell factor and IL-3, both at 20 ng/ml (Perpo Tech), and G-CSF and GM-CSF, both at 10 ng/ml (Perpo Tech). The resulting colonies were scored after two weeks of incubation at 37° C. in a humidified atmosphere of 5% $CO_2$ in air. Colonies were classified as blast, mixed, erythroid, myeloid, and megakaryocytic, according to their cellular composition.

Morphological assessment: In order to characterize the resulting culture populations, aliquots of cells were deposited on a glass slide (cytocentrifuge, Shandon, Runcorn, UK), fixed and stained in May-Grunwald and Giemsa stain.

Surface antigen analysis: At different time intervals, the cultured cells were harvested, washed with a PBS solution containing 1% BSA and 0.1% sodium azide (Sigma), and stained, at 4° C. for 60 minutes, with FITC-labeled anti $CD_{45}$ monoclonal antibody and either PE-labeled anti $CD_{34}$ (HPCA-2) monoclonal or PE-labeled control mouse Ig (all from Immunoquality Products, the Netherlands). The cells were then washed with the same PBS solution and were analyzed by a flow cytometer, as described hereinafter.

Flow cytometry analysis: Cells were analyzed and sorted using FACS calibur flow cytometer (Becton-Dickinson, Immunofluorometry systems, Mountain View, Calif.). Cells were passed at a rate of 1,000 cells/second through a 70 μm nozzle, using a saline sheath fluid. A 488 nm argon laser beam at 250 mW served as the light source for excitation. Fluorescence emission of ten thousand cells was measured using a logarithmic amplification and analyzed using CellQuest software.

Experimental Results

Effects of TEPA-Cu chelate on the expansion of $CD_{34}^+$ cells: Cultures of enriched $CD_{34}^+$ cell fraction were supplemented weekly with a cocktail of one of two groups of four cytokines: TPO, FLT-3, IL-6 and IL-3, or with TPO, FLT-3, IL-6 and SCF. Each culture was treated with TEPA-Cu chelate at different concentrations or remained treated only with the cytokines described hereinabove. The analysis of 8 week-old cultures is illustrated in FIG. 1 and clearly indicates that stem cell cultures supplemented with TEPA-Cu yielded substantially more colony-forming cells of $CD_{34}^+$ as compared with cultures treated only with cytokines. The results presented in FIG. 1 further indicate that treatment with higher concentrations of TEPA-Cu (e.g., 100 μM) was substantially more effective than treatment with TEPA-Cu at lower concentrations (e.g., 10 and 50 μM).

Figure 2A:
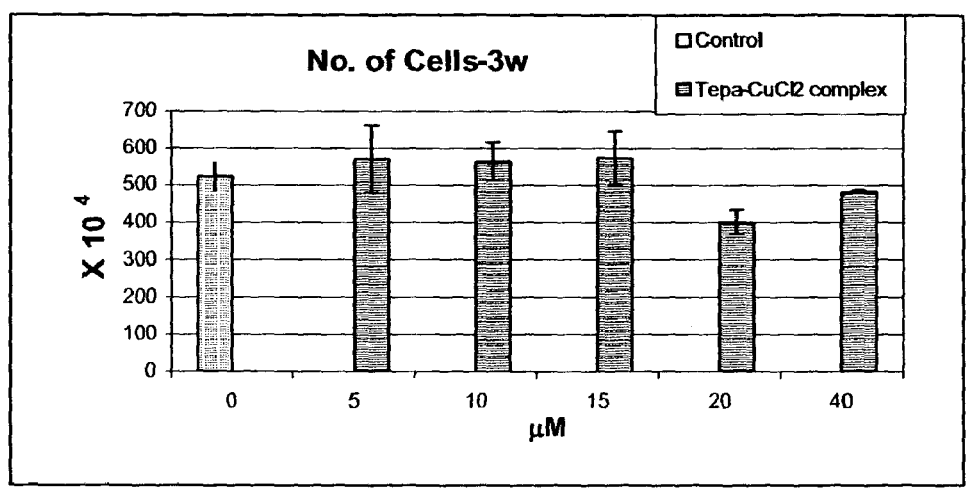
FIGS. 2a-d illustrate the short and long-term effects of TEPA-copper (TEPA-Cu) chelate on the expansion of $CD_{34}^+$ hematopoietic stem cells, cultured ex vivo. Purified $CD_{34}^+$ cells were plated in liquid culture, at $10^4$ cell/ml, in the presence of cytokines, with or without different concentrations of the chelate. The cultures were assayed for the total number of cells and for the number of colony-forming cells (CFUs), after 3 weeks (FIG. 2a), 5 weeks (FIG. 2b), 6 weeks (FIG. 2c) and 8 weeks (FIG. 2d).
Figure 2A:
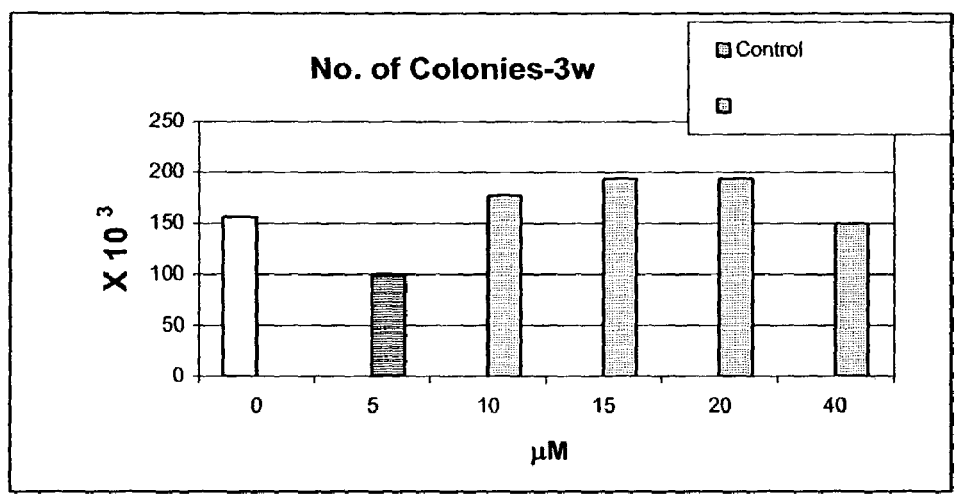
Figure 2B:
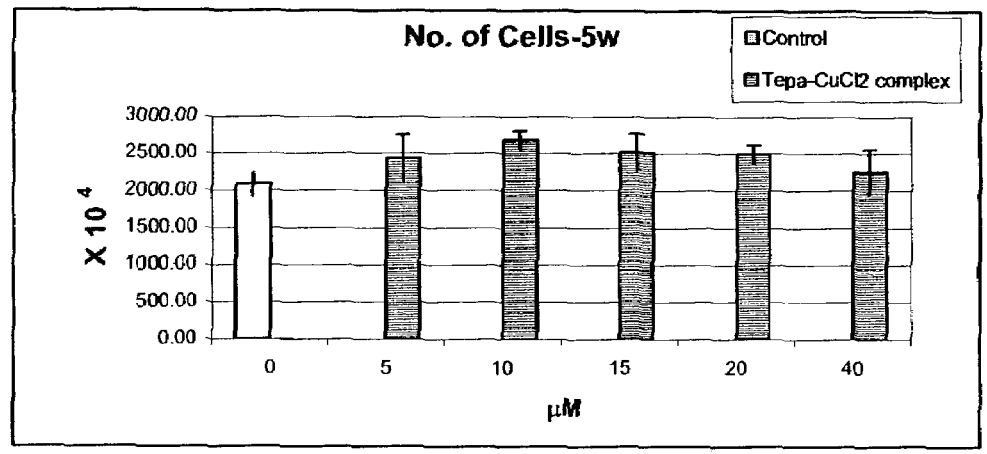
Figure 2B:
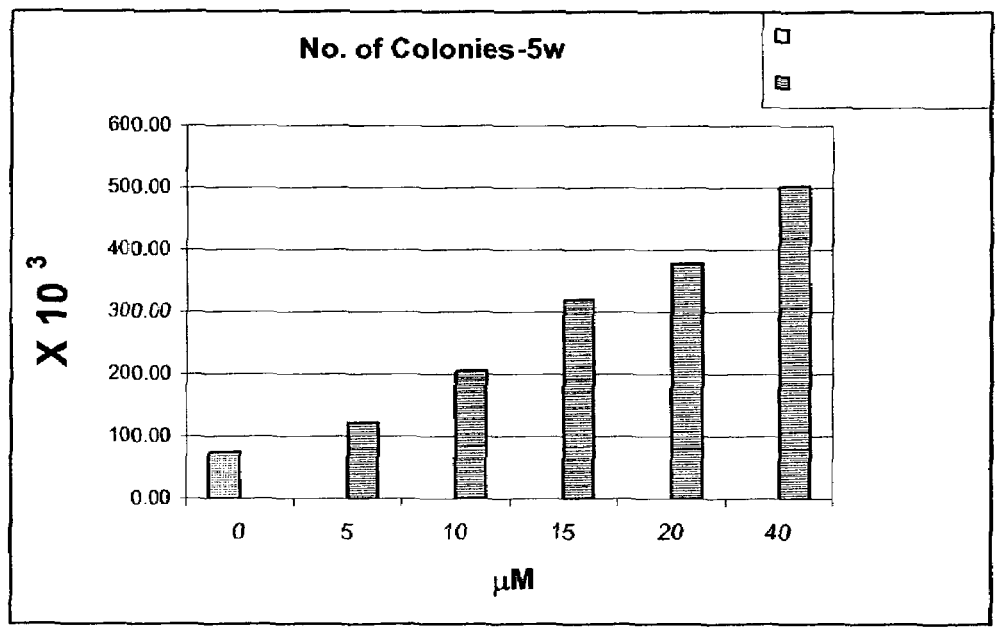
Figure 2C:
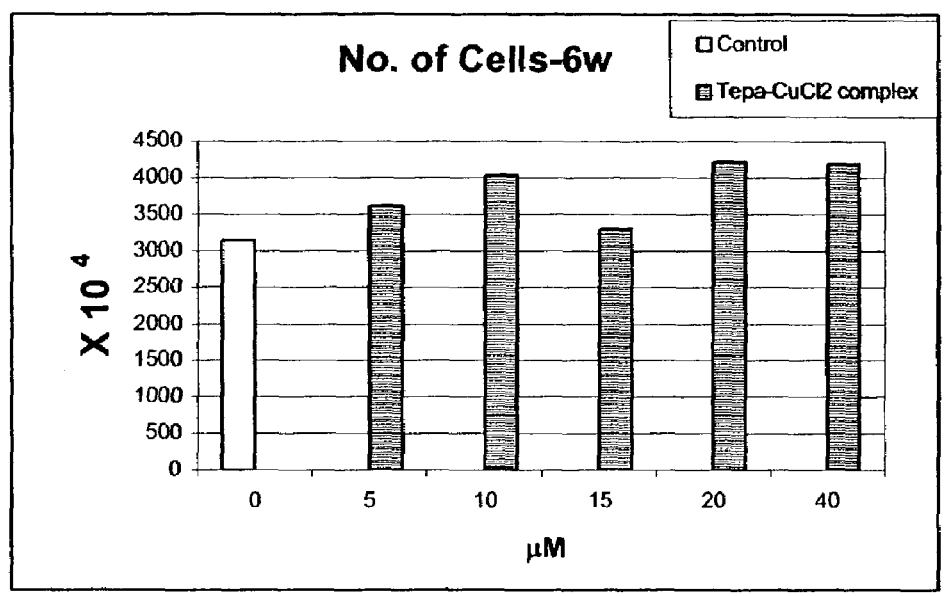
Figure 2C:
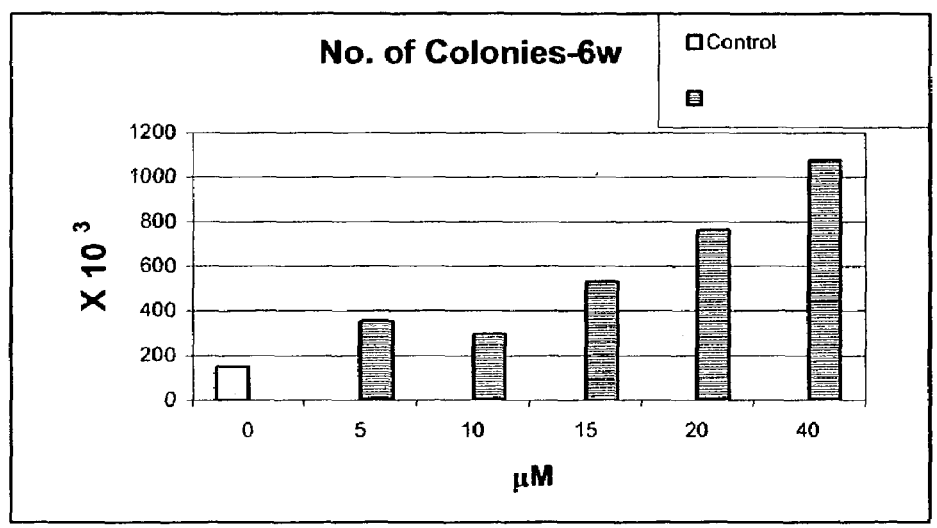
Figure 2D:
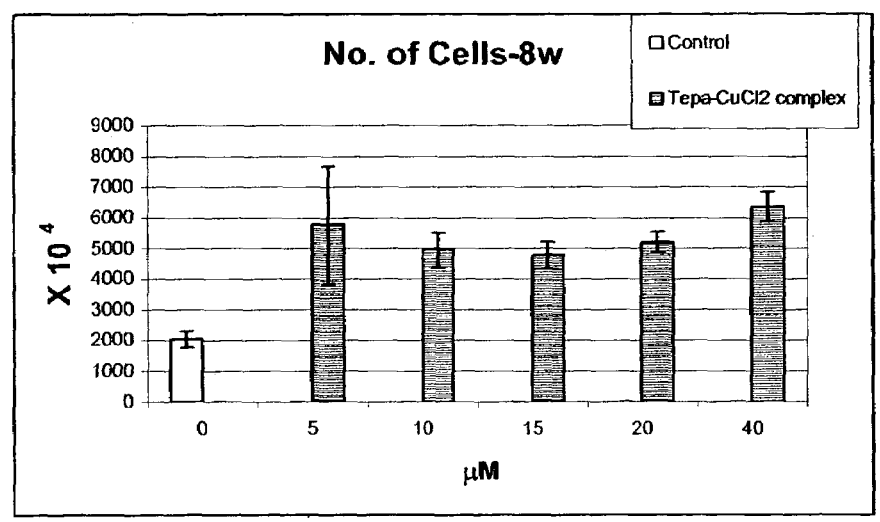
Figure 2D:
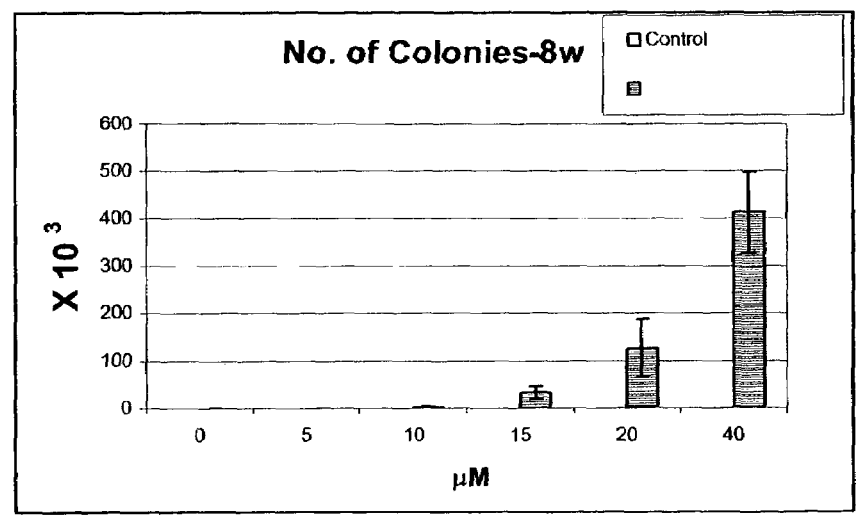

In another experiment, TEPA-Cu was supplemented to $CD_{34}^+$ cell cultures for a shortened time period of three weeks, while cytokines were supplied continuously throughout the culture incubation periods. At the end of 3, 5, 6 and 8 weeks incubation the densities of cells and colony-forming cells (CFUc) were determined. The results are presented in FIGS. 2a-d and show that three weeks cultures had similar numbers of cells and CFUc upon all treatments. On the other hand, after a longer incubation period the numbers of CFUc were substantially higher in cultures treated with the copper chelate, as compared with the non-treated control (cytokines only; FIGS. 2b-d). Furthermore, it was found that there was a dose-response between the amount of TEPA-Cu provided to culture and the resulting values of CFUc. For example, FIG. 2d shows that eight-week cultures treated with 0 (control), 5, 10, 15, 20 and 40 μM of TEPA-Cu, resulted in 0, 0, 1, 30, 120 and 400 CFUc, respectively.

Figure 3A:
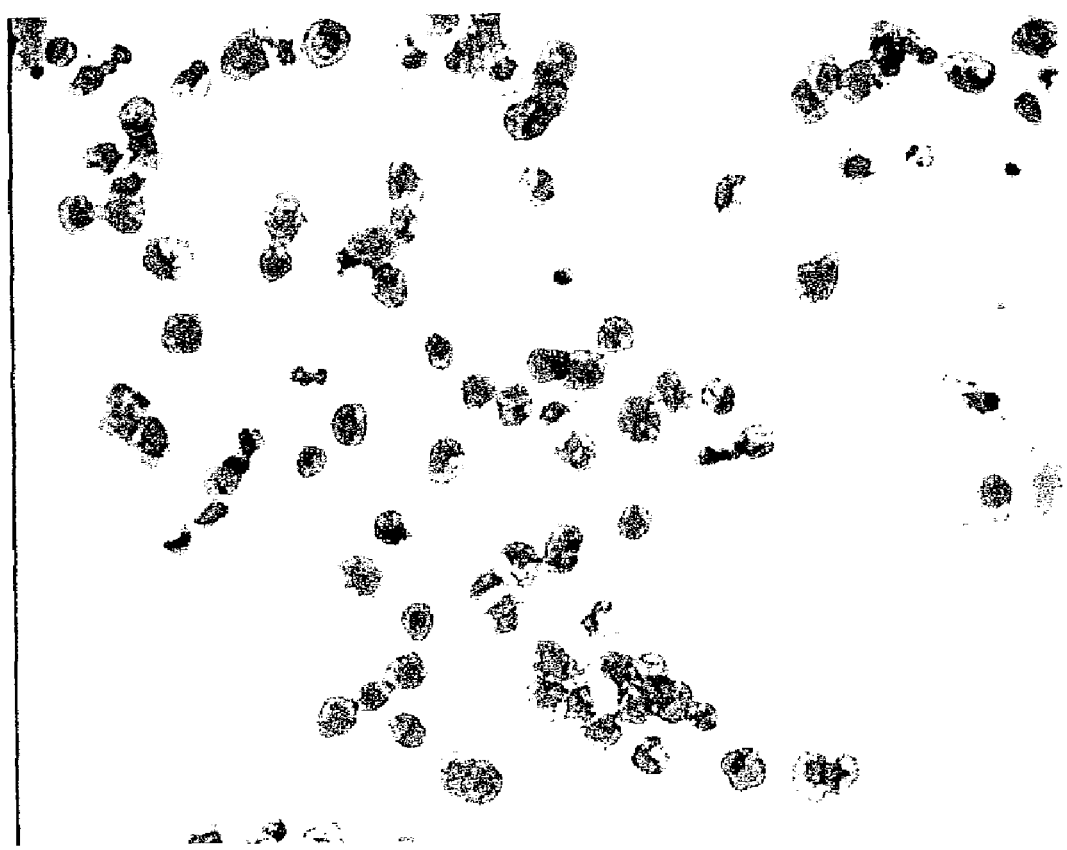
FIGS. 3a-b are photomicrographs of hematopoietic stem cells, cultured ex vivo with or without TEPA-copper (TEPA-Cu) chelate.
Figure 3B:
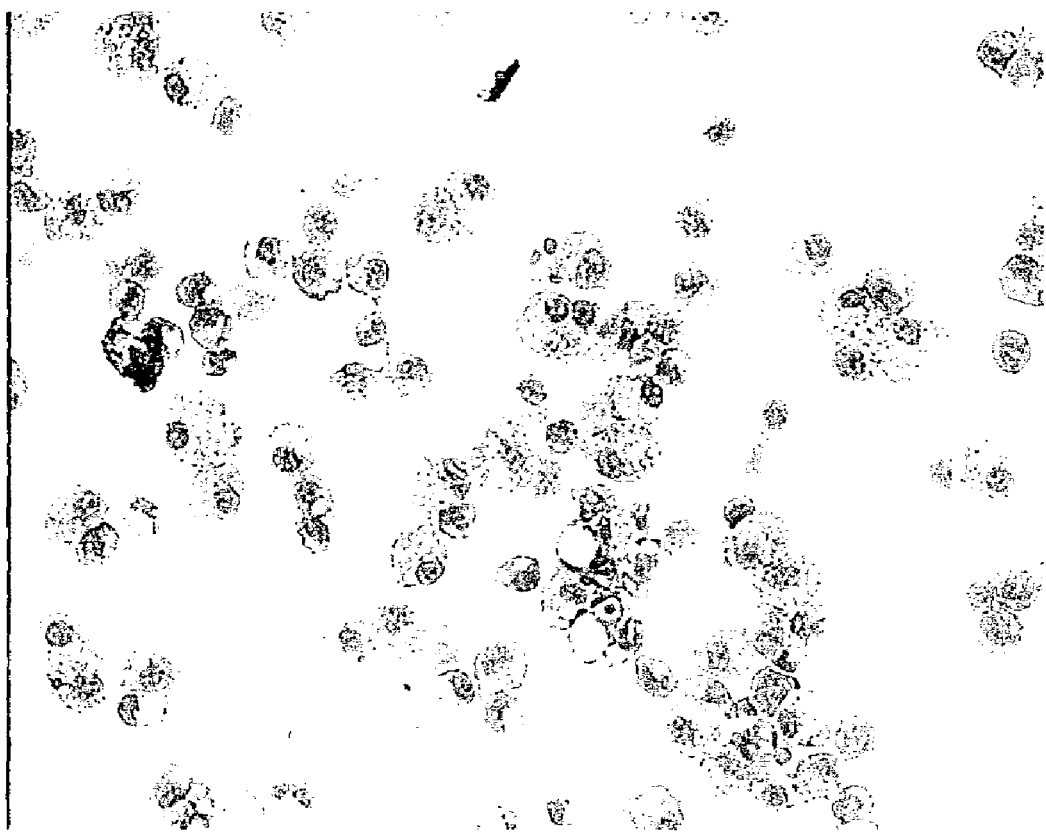

A morphological analysis of an 8-weeks culture, presented in FIGS. 3a and 3b, further demonstrates that the differentiation of stem cells was inhibited in a culture treated with TEPA-Cu. Slides samples illustrated in FIGS. 3a-b, show chelate-treated cultures which contain mainly blast-like cells (indicative of nondifferentiated stem cells), whereas control cultures (not treated with the copper chelate), contain mainly differentiated cells.

Figure 4A:
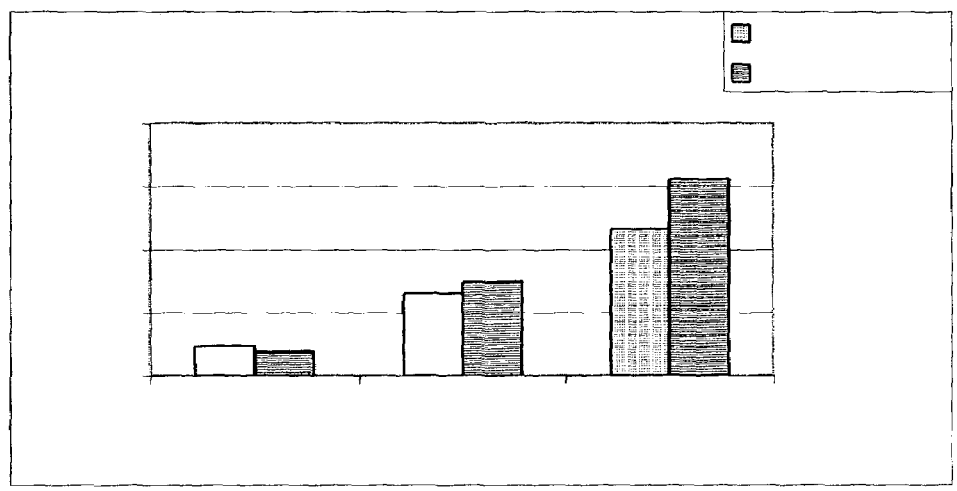
FIGS. 4a-c illustrate the effect of TEPA-copper (TEPA-Cu) chelate on the short-term expansion of stem and progenitor cells, cultured ex vivo. Purified $CD_{34}^+$ cells were seeded in culture bags in the presence of early cytokines, with or without TEPA-Cu chelate (at a concentration of 40 μM). After 1, 2 and 3 weeks of incubation half of the bag content was taken for re-purification of $CD_{34}^+$ cells using miniMacs columns. The re-purified cells were comparatively enumerated for the cell density of $CD_{34}^+$ cells (FIG. 4a) and FACS-analyzed for the density of $CD_{34}^+ CD_{38}^-$ cells (FIG. 4b) and for the density of $CD_{34}^+ Lin^-$ cells (FIG. 4c).
Figure 4A:
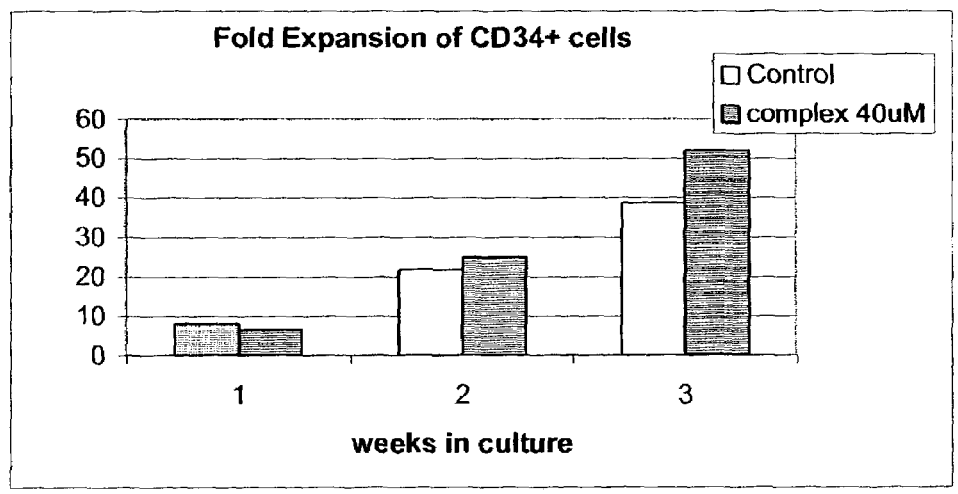
Figure 4B:
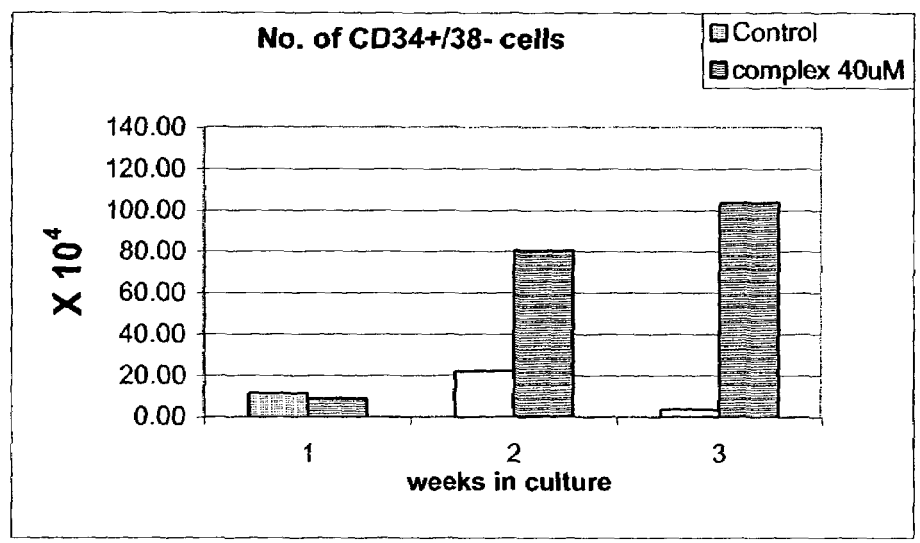
Figure 4B:
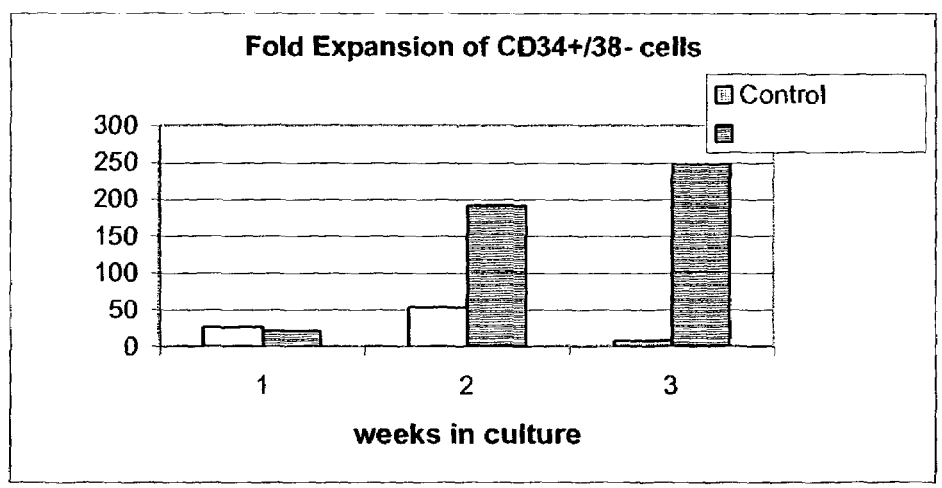
Figure 4C:
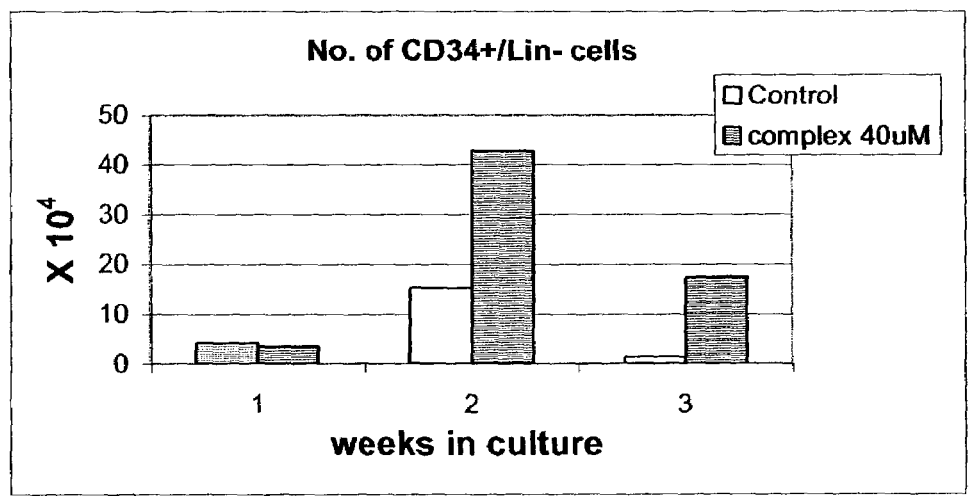
Figure 4C:
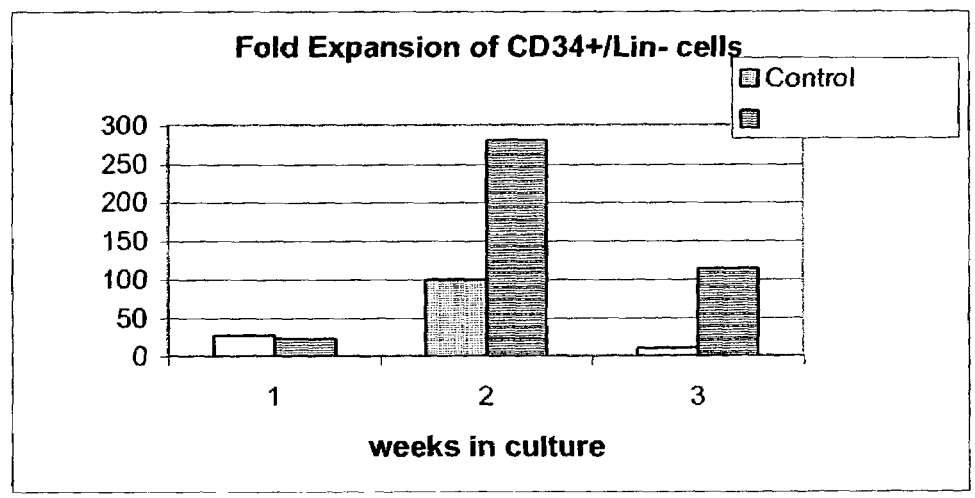

Effects of TEPA-Cu chelate on the expansion of stem and progenitor cells: Cultures of enriched $CD_{34}^+$ cells were supplemented weekly with four early cytokines (TPO, FLT-3, IL-6 and SCF) and were treated or un-treated with TEPA-Cu. After two or three weeks of incubation, the $CD_{34}^+$ stem cells were purified, enumerated, stained for lineage specific antigens and analyzed by FACS for the content of $CD34^+$ $CD38^-$ and $CD_{34}^+$ $Lin^-$ early progenitor cells. As is shown in FIGS. 4a-b, after three weeks of incubation the density of $CD_{34}^+$ stem cells expanded by 40 fold and 50 fold in the untreated and the chelate-treated cultures, respectively (FIG. 4a), the density of $CD_{34}^+$ $CD_{38}^-$ progenitor cells expanded by 5 fold and 250 fold in the untreated control and the chelate-treated cultures, respectively (FIG. 4b), and the density of $CD_{34}^+$ $Lin^-$ progenitor cells expanded by 10 fold and 110 fold, in the untreated control and the chelate-treated cultures, respectively.

Figure 5A:
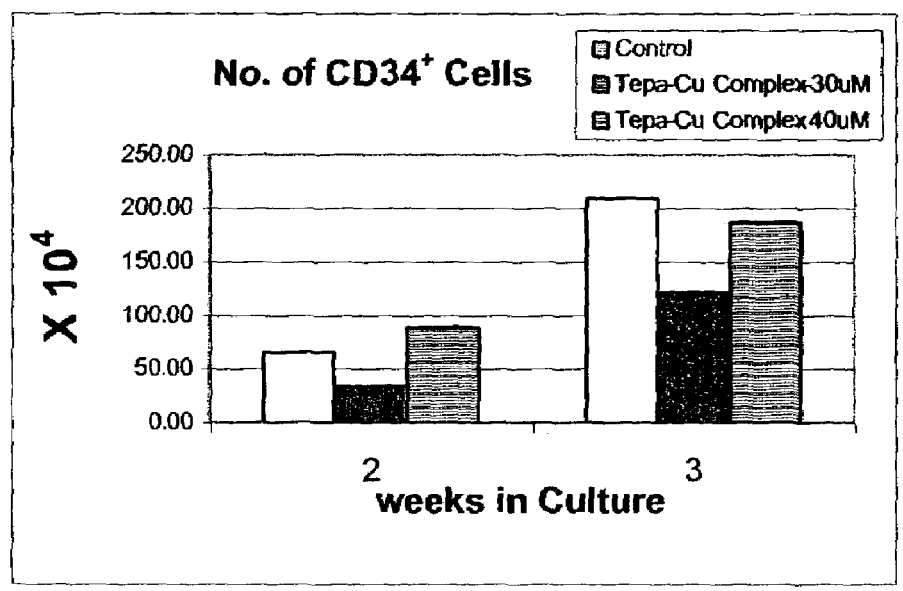
FIGS. 5a-c illustrate the effect of TEPA-copper (TEPA-Cu) chelate on the short-term expansion of stem and progenitor cells, cultured ex vivo. Purified $CD_{34}^+$ cells were seeded in culture bags in the presence of early cytokines, with or without TEPA-Cu chelate (at a concentration of 30 μM or 40 μM). After 2 and 3 weeks of incubation half of the bag content was taken for re-purification of $CD_{34}^+$ cells using miniMacs columns. The re-purified cells were enumerated for the density of $CD_{34}^+$ cells (FIG. 5a) and FACS-analyzed for the density of $CD_{34}^+ CD_{38}^-$ cells (FIG. 5b) and for the density of $CD_{34}^+ Lin^-$ cells (FIG. 5c).
Figure 5B:
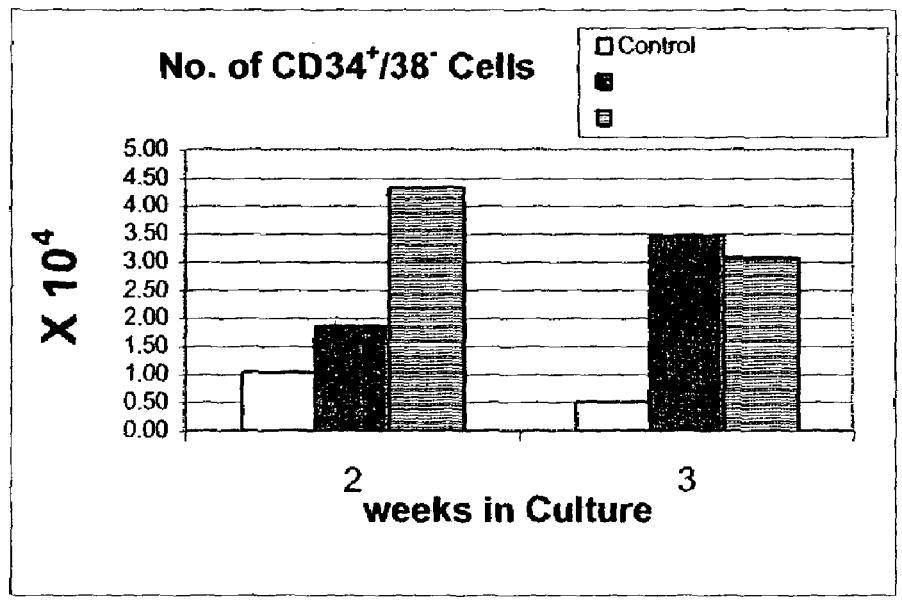
Figure 5C:
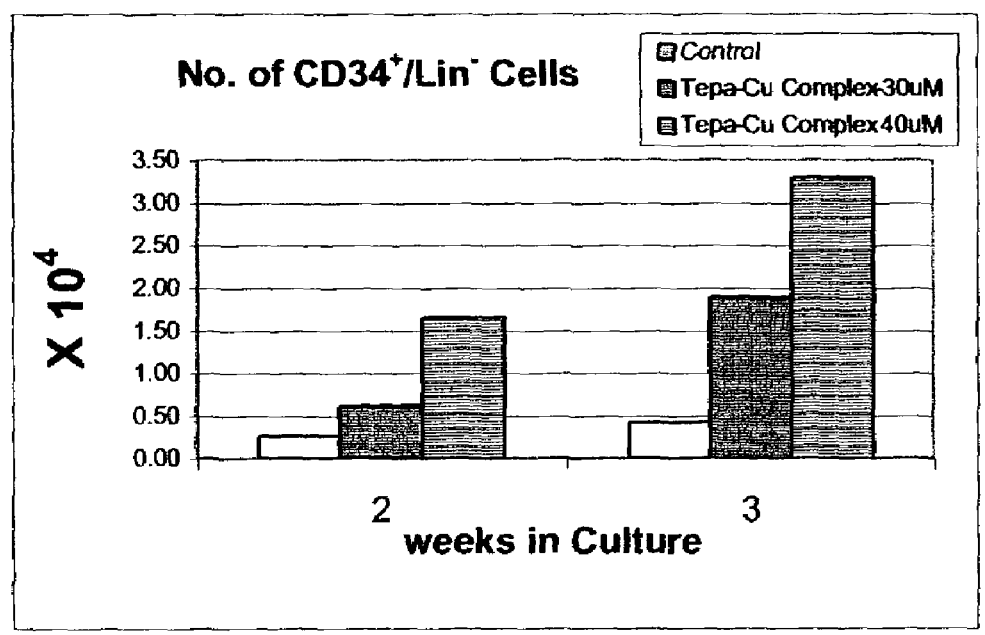

As is shown in FIGS. 5a-c, in another, similar experiment, the number of $CD_{34}^+$ cells in the chelate-treated culture remained almost unchanged as compared with the number of $CD_{34}^+$ cells in the untreated (cytokines only) culture after 2 and 3 weeks (FIG. 5a). On the other hand, after 3 weeks of incubation the number of $CD_{34}^+$ $CD_{38}^-$ cells in the chelate-treated cultures was 6-7 fold higher than in the untreated control (FIG. 5b), and the number of $CD_{34}^+$ Lin$^-$ cell in the chelate-treated culture was 4-6.5 fold higher than in the untreated control (FIG. 5c).

Figure 6A:
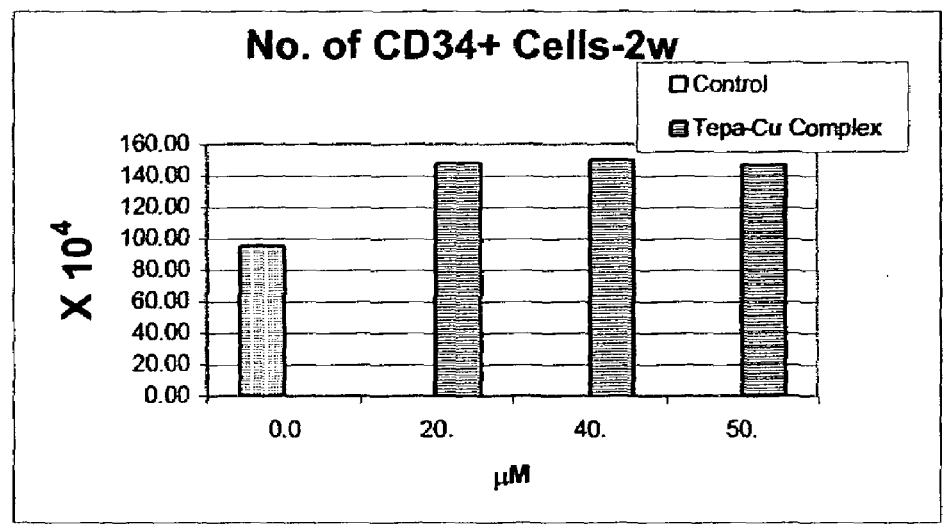
FIGS. 6a-d illustrate the effect of TEPA-copper (TEPA-Cu) chelate on the short-term expansion of stem and progenitor cells, cultured ex vivo. Purified $CD_{34}^+$ cells were seeded in culture bags in the presence of cytokines, with or without various concentrations of the TEPA-Cu chelate (20, 40 or 50 μM). After 2 weeks of incubation half of the bag content was taken for re-purification of $CD_{34}^+$ cells using miniMacs columns. The re-purified cells were numerated for the density of $CD_{34}^+$ cells (FIG. 6a) and FACS-analyzed for the density of $CD_{34}^+ CD_{38}^-$ cells (FIG. 6b) and for the density of $CD_{34}^+ Lin^-$ cells (FIG. 6c). In addition, the numbers of colony-forming cells (CFUs) were comparatively measured in 2, 3 and 4 weeks-old cultures (FIG. 6d).
Figure 6B:
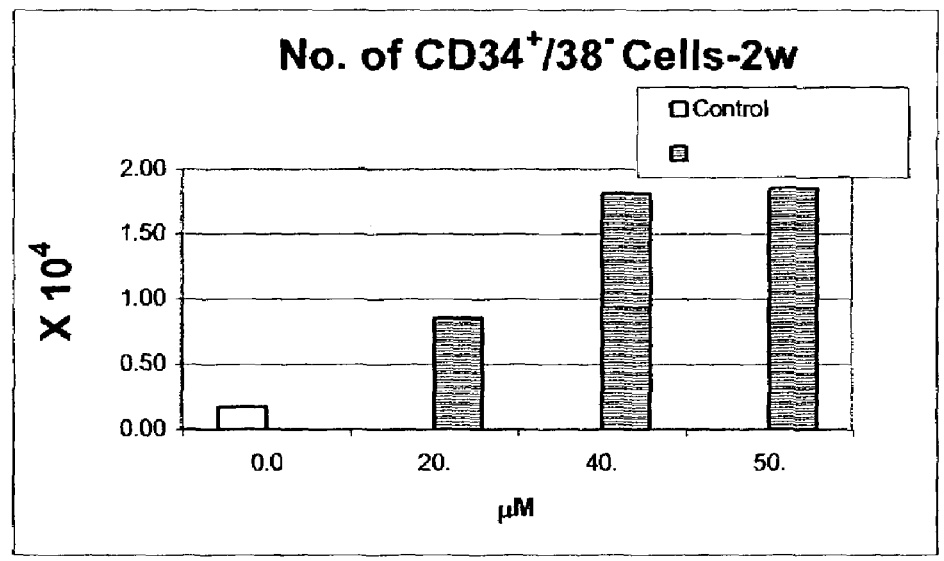
Figure 6C:
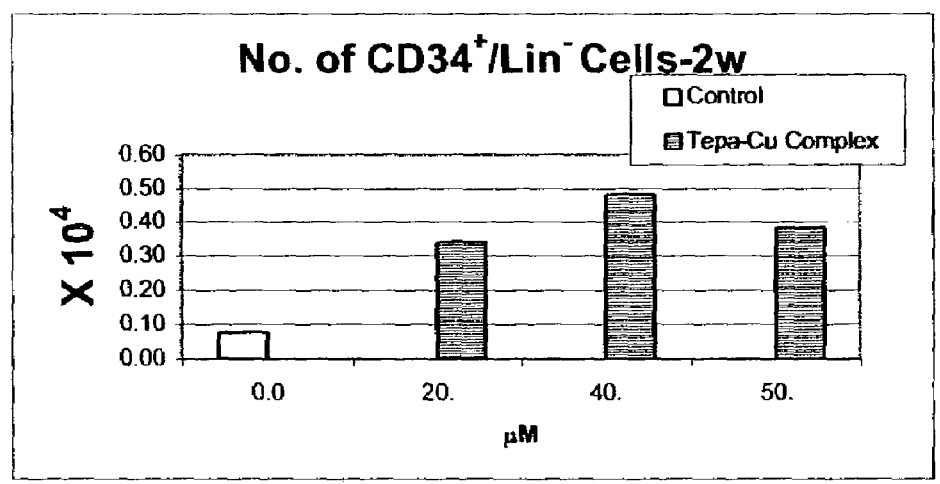
Figure 6D:
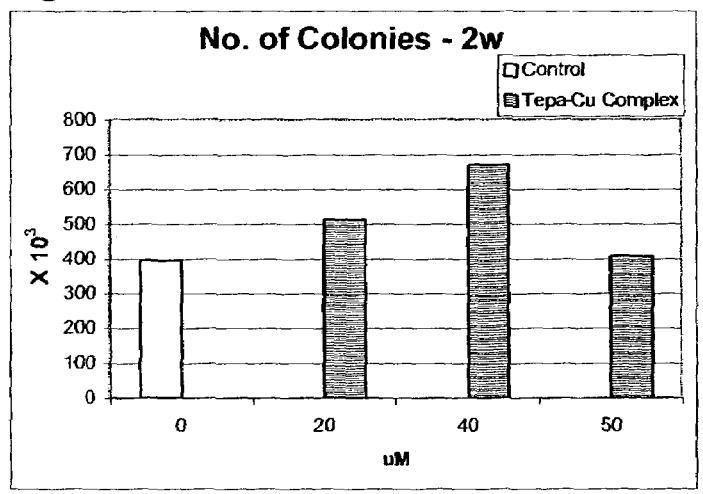
Figure 6D:
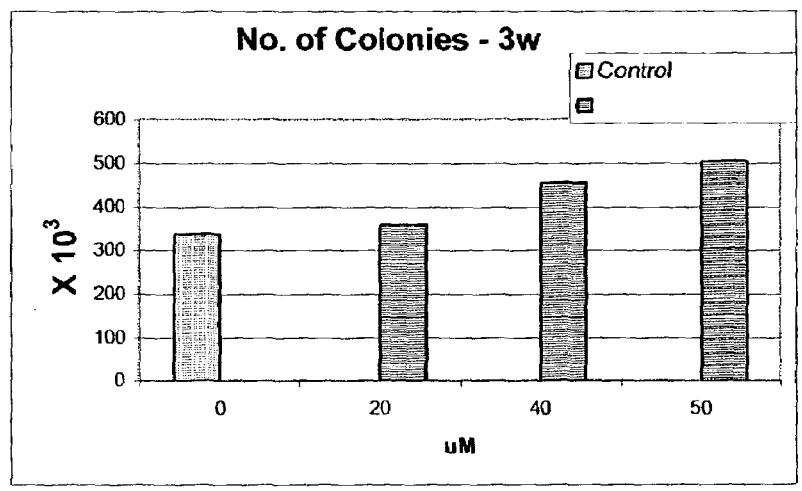
Figure 6D:
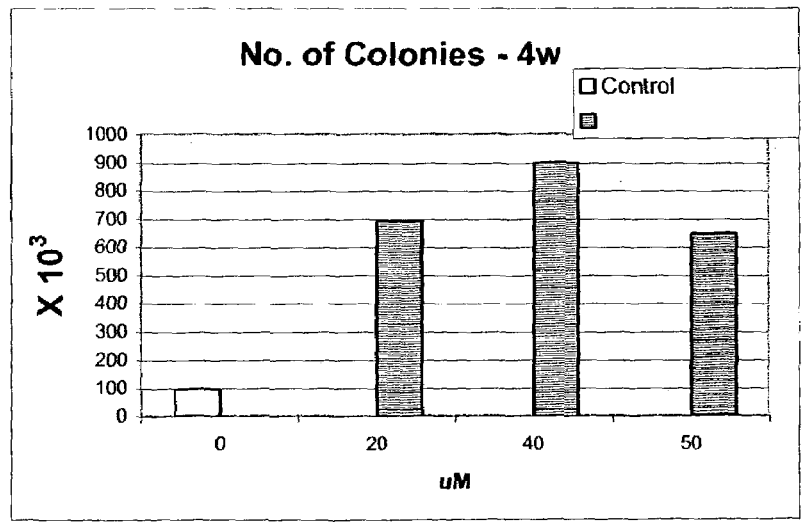

In yet another experiment, enriched $CD_{34}^+$ cells were supplemented weekly with the 3 early cytokines (TPO, FLT-3, and IL-6), and with the differentiation-inducing cytokine IL-3. The cultures were also treated with TEPA-Cu at concentrations of 0 (untreated control), 20, 40 and 50 µM. After two weeks the numbers of $CD_{34}^+$ cells and CFUc were scored. In addition, $CD_{34}^+$ cells from the two-weeks old culture were purified, stained for lineage specific antigens, and analyzed by FACS for the density of $CD_{34}^+$ $CD_{38}^-$ and for the density of $CD_{34}^+$ Lin$^-$ progenital cells. The results are presented in FIGS. 6a-d, and show that the density of $CD_{34}^+$ stem cells was moderately (ca. 1.5 fold) higher in the chelate-treated cultures, as compared with the untreated control (FIG. 6a). On the other hand, the densities of $CD_{34}^+$ $CD_{38}^-$ cells were 5, 15 and 15 fold higher in cultures treated with 20, 40 and 50 µM of TEPA-Cu, respectively, as compared with the untreated control (FIG. 6b). Similarly, the densities of $CD_{34}^+$ Lin$^-$ progenitor cells were 3, 5 and 4 fold higher in cultures treated with 20, 40 and 50 µM of TEPA-Cu, respectively, as compared with the untreated control (FIG. 6c). FIG. 6d shows that after four weeks of incubation the numbers of $CD_{34}^+$ Lin$^-$ colony-forming cells were 7, 9 and 7.5 fold higher in the cultures treated with 20, 40 and 50 µM of TEPA-Cu, respectively, as compared with the untreated control.

Figure 7A:
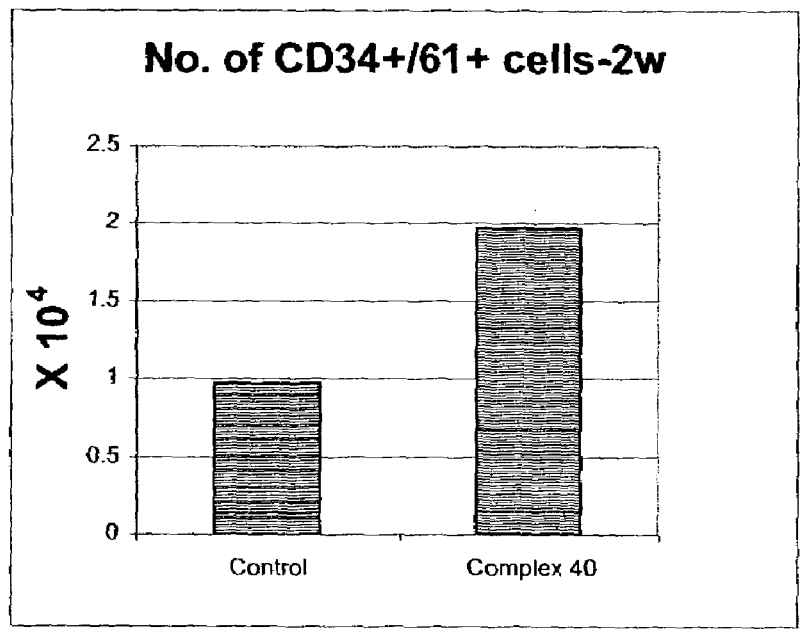
FIGS. 7a-b illustrate the effect of TEPA-copper (TEPA-Cu) chelate on the short-term expansion of lineage-committed progenitor cells, cultured ex vivo. Purified $CD_{34}^+$ cells were cultured in the presence of early cytokines, with or without TEPA-Cu chelate (at a concentration of 40 μM). After 2 weeks of incubation half of the bag content was taken for re-purification of $CD_{34}^+$ cells using miniMacs columns. The re-purified cells were FACS-analyzed for the density of $CD_{34}^+ CD_{61}^+$ cells (FIG. 7a) and for the density of $CD_{34}^+ CD_{41}^+$ cells (FIG. 7b).
Figure 7B:
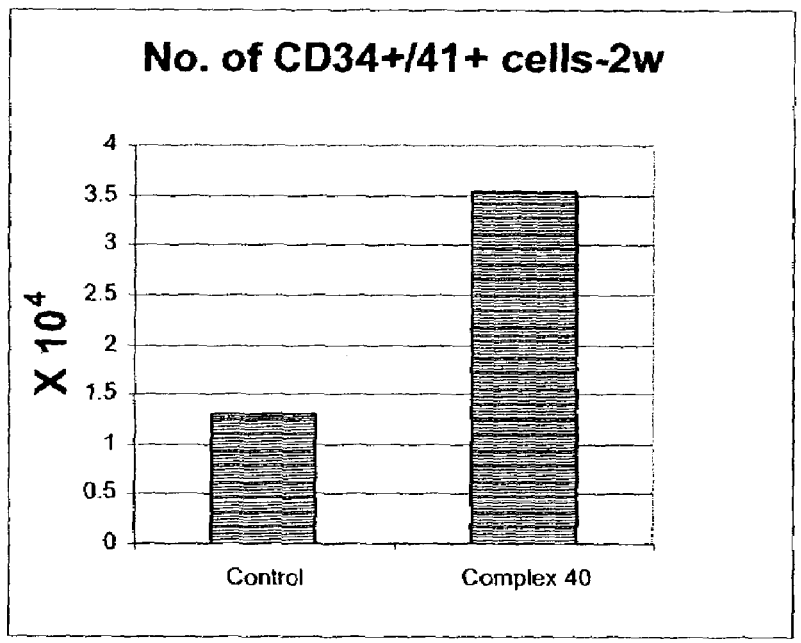

In still another experiment, cultures of enriched $CD_{34}^+$ cells were supplemented weekly with four early cytokines (TPO, FLT-3, IL-6 and SCF) and were treated or untreated with TEPA-Cu chelate. After two or three weeks, $CD_{34}^+$ cells were purified, enumerated, stained for lineage specific antigens and analyzed by FACS for the content of $CD_{34}^+$ $CD_{61}^+$ and for the content of $CD_{34}^+$ $CD_{41}^+$ Mega progenitor cells. The results are presented in FIG. 7a, and show that in two weeks cultures, the addition of TEPA-Cu to the cultures media substantially expanded the densities of $CD_{34}^+$ $CD_{61}^+$ and $CD_{34}^+$ $CD_{41}^+$ progenitor cells, by ca. 2 and 3 fold respectively, as compared with the untreated control.

Hence, the experimental results described hereinabove clearly demonstrate that TEPA-Cu treatment of ex vivo cell culture substantially and selectively promotes the expansion of lineage-committed progenitor cells, relatively to $CD_{34}^+$ stem cells, in a short-term (2-3 weeks) culture.

Example 2

Comparative Effects of TEPA-Cu Chelate and TEPA Chelator on the Cellular Copper Content of Stem Cells Experimental Procedures Cell cultures: Cultures of enriched $CD_{34}^+$ cell fraction were generated, maintained and analyzed as described in Example 1 above.

Copper Determination: Cells were harvested by centrifugation at 1000 g for 5 minutes. The cell pellet was washed three times in PBS. Aliquots containing $2\times10^6$ cells were then transferred into a metal-free Eppendorf tube and pelleted by centrifugation at 1000 g. The cell pellet was re-suspended in 0.03 M ultra-pure nitric acid to give a concentration of $1\times10^7$ cells/ml. The cells were sonicated and then analyzed in duplicate by a Perkin Elmer graphite furnace atomic absorption spectrophotometer at a wavelength of 324.7 nm and a 0.7 slit width. The following times and temperatures were used: drying at 95° C. for 45 seconds with a 15-s ramp; charring at 900° C. for 30 seconds with a 10-s ramp, and atomization at 900° C. for 10 seconds. The peak area was integrated for 10 seconds. The samples were analyzed against copper standard solution prepared from a commercial stock solution that was diluted with 0.03 M ultra pure nitric acid.

Experimental Results

Effect of TEPA-Cu chelate and TEPA chelator on the cellular copper content: Purified $CD_{34}^+$ cell were seeded in liquid culture in the presence of early cytokines and treated either with TEPA-Cu chelate or with TEPA chelator. After 2 days incubation, cells were separated from culture media and analyzed for cellular copper content. The results are presented in Table 1 below and indicate that cultured cells treated with TEPA-Cu chelate, at different concentrations, developed progressively higher cellular copper content. In contrast, cultured cells treated with TEPA chelator, at different concentrations, developed progressively lower cellular copper contents. Hence, both TEPA-Cu chelate and the TEPA chelator affected the cellular copper content in a dose-response manner, but in opposite directions.

TABLE 1

| Treatment | Concentration (µM) | Relative cellular-copper content (%)* |
|---|---|---|
| TEPA chelator | 5 | 80 |
| TEPA chelator | 10 | 55 |
| TEPA chelator | 20 | 42 |
| TEPA-Cu chelate | 10 | 178 |
| TEPA-Cu chelate | 30 | 235 |
| TEPA-Cu chelate | 60 | 290 |

*Percentage values are relative to the cellular copper content of the untreated control.

Example 3

Comparative Effects of TEPA-Cu Chelate and TEPA Chelator on the Proliferation and Differentiation of Stem and Progenitor Cells Experimental Procedures Cell cultures: Cultures of enriched $CD_{34}^+$ cell fraction were carried out as described in the experimental procedures section of Example 1 above.

Determination of the density of stem and progenitor subset populations following expansion: Following an incubation period, the $CD_{34}^+$ cells were re-selected using mini-MACS Miltenyi kit. The purity of the positive fraction of selected $CD_{34}^+$ cells was confirmed by FACS analysis as well as by cell morphology analysis. The density of $CD_{34}^+$ cells, in proportion (percentage) to total cells, was determined directly via FACS analysis. The densities of $CD_{34}^+$ subset populations were determined from the purified $CD_{34}^+$ fraction. Re-selected $CD_{34}^+$ cells were stained with lineage specific antigens followed by FACS analysis to determine the percentage of the subset populations within the total number of $CD_{34}^+$ cells. The fold expansion of subset populations of cells was determined by using the calculated average density of the re-purified $CD_{34}^+$ cells as time 0 baseline.

Experimental Results

Figure 8A:
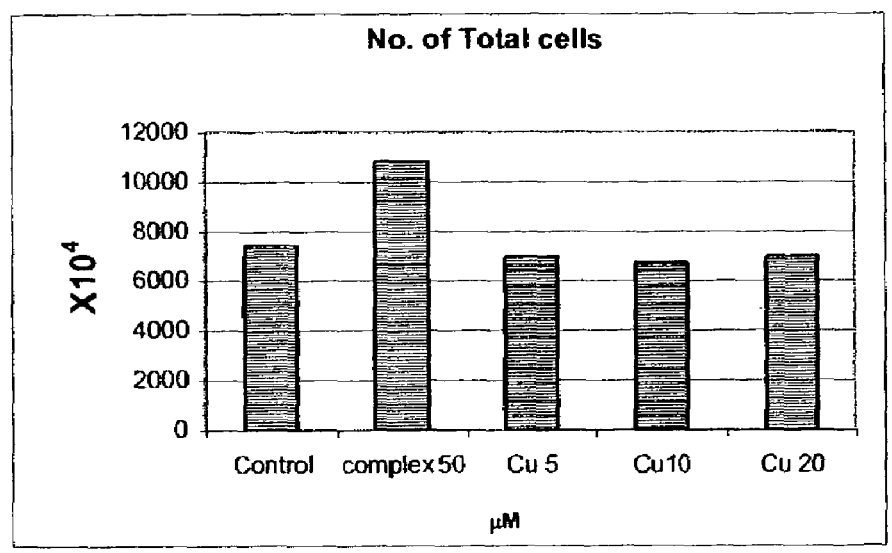
FIGS. 8a-d illustrate the effects of TEPA-copper (TEPA-Cu) chelate and of copper chloride salt, on the short-term (3 weeks) expansion of stem and progenitor cells, cultured ex vivo. Purified $CD_{34}^+$ cells were seeded in culture bags in the presence of early cytokines, and with TEPA-Cu chelate at a concentration of 50 μM; or with various concentrations of copper chloride (5, 10 or 20 μM); or untreated (control). After 3 weeks of incubation the total cells were comparatively enumerated (FIG. 8a) while half of the bag content was taken for re-purification of $CD_{34}^+$ cells using miniMacs columns. The re-purified cells were enumerated for the density of $CD_{34}^+$ cells (FIG. 8b) and FACS-analyzed for the density of $CD_{34}^+ CD_{38}^-$ cells (FIG. 8c) and for the density of $CD_{34}^+ Lin^-$ cells (FIG. 8d).
Figure 8B:
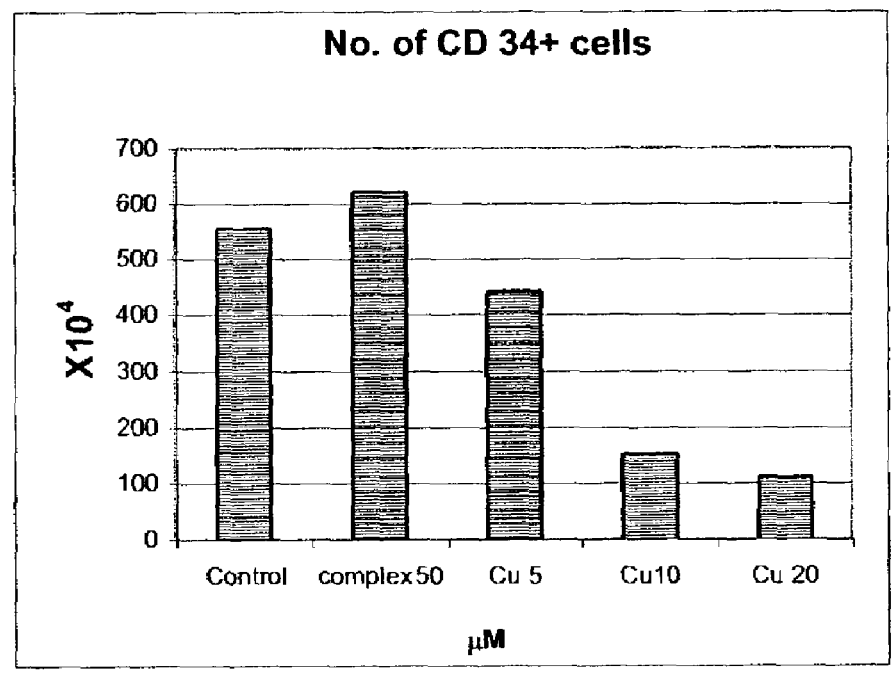
Figure 8C:
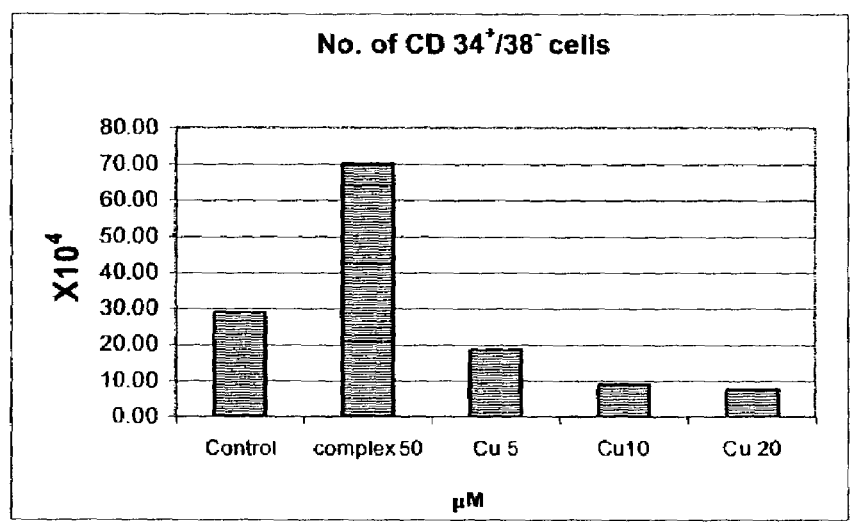
Figure 8D:
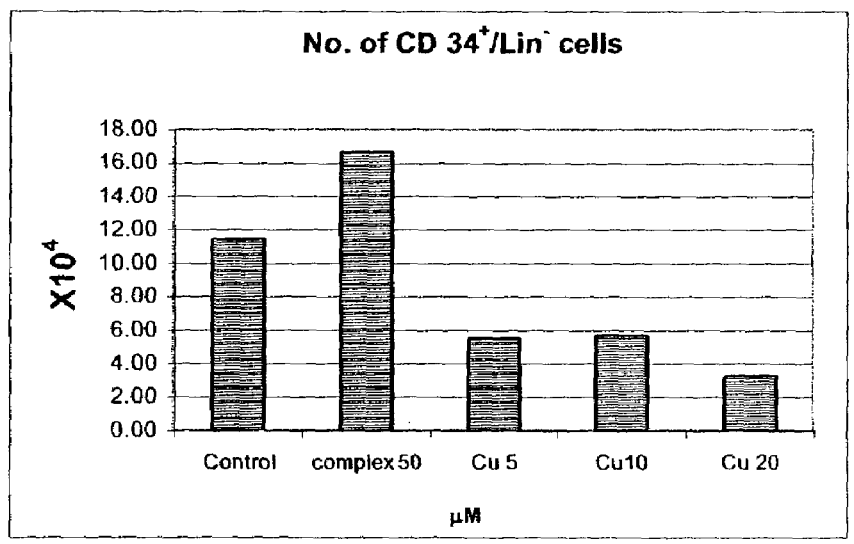

Comparative effects of TEPA-Cu chelate, copper salt and TEPA chelator on $CD_{34}^+$ cells proliferation and differentiation in culture: Cultures of $CD_{34}^+$ stem cells were supplemented with 4 early cytokines (TPO, FLT-3, IL-6 and SCF) and were treated with either TEPA-Cu chelate or copper chloride. Three weeks old cultures were harvested and comparatively analyzed for the number of total cells, number of $CD_{34}^+$ cells, number of $CD_{34}^+$ $CD_{38}^-$ cells, and the number of $CD_{34}^+$ Lin$^-$ cell. As is shown in FIG. 8a, cultured stem cells treated with TEPA-Cu yielded more total cells (ca. 25%) as compared with the untreated control, while the number of total cells measured in cultures treated with copper chloride did not differ significantly from the untreated control. The results illustrated in FIGS. 8b-c show that cell cultures supplemented with copper chloride had fewer stem cells ($CD_{34}^+$), and fewer stem/progenitor subset cells ($CD_{34}^+$ $CD_{38}^-$ and $CD_{34}^+$ Lin$^-$), as compared with either the untreated or with the chelate-treated cultures. On the other hand, cultures supplemented with TEPA-Cu chelate resulted in substantially higher densities of $CD_{34}^+$ $CD_{38}^-$ and $CD_{34}^+$ Lin$^-$ stem/progenitor subset cells, as compared with the untreated control.

Figure 9:
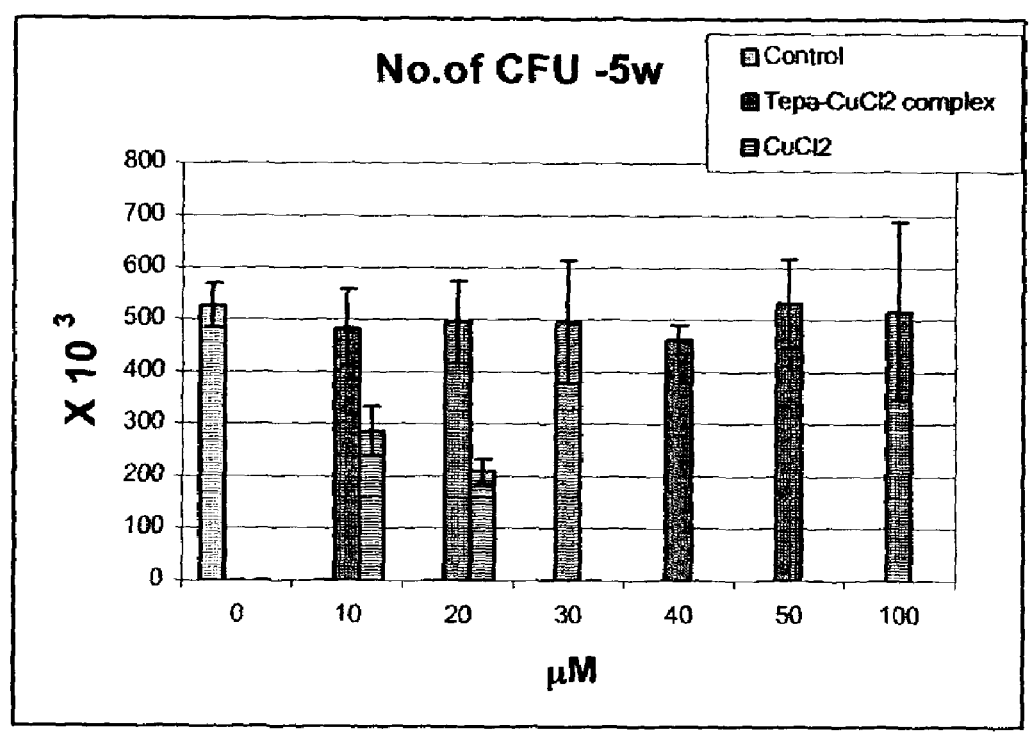
FIG. 9 illustrates the effects of TEPA-copper (TEPA-Cu) chelate and of copper chloride salt, on the long-term (5 weeks) expansion of stem and progenitor cells, cultured ex vivo. Purified $CD_{34}^+$ cells were cultured and supplemented with early cytokines, with TEPA-Cu chelate at various concentrations (10, 20, 30, 40, 50 and 100 µM); or with copper chloride at a concentration of 10 or 20 µM; or untreated (control). The Figure shows the comparative numbers of colony-forming cells (CFUs) measured in 5 weeks old cell cultures.

In another experiment, TEPA-Cu chelate or copper chloride were added to the culture media during the first three weeks, while cultures were maintained for a total of five weeks period. At the end of the incubation period the number of colony-forming cells of $CD_{34}^+$ cells were measured and is compared. The results are illustrated in FIG. 9 and show that the five-weeks culture treated with copper chloride had substantially fewer colony-forming cells of $CD_{34}^+$, as compared with untreated cultures or with cultures treated with TEPA-Cu.

Figure 10:
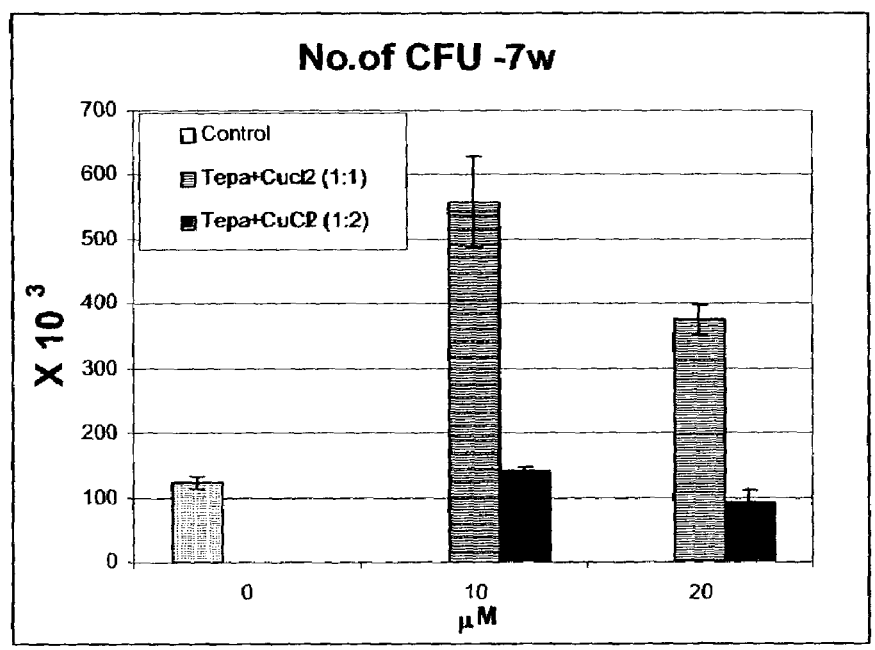
FIG. 10 illustrates the effects of two mixtures containing TEPA chelator and copper chloride on the long-term expansion of stem cells, cultured ex vivo. Purified $CD_{34}^+$ cells were seeded in liquid culture in the presence of cytokines, with a mixture of TEPA chelator and copper chloride at 1:1 molar ratio; or with a mixture of TEPA chelator and copper chloride at 1:2 respective molar ratio; or untreated (control). The Figure shows the comparative numbers of colony-forming cells (CFUs) measured in 7 weeks old cell cultures.

In another experiment, the simultaneous effects of TEPA chelator and copper salt were evaluated. Accordingly, cultures of enriched $CD_{34}^+$ stem cells were supplemented with 4 early cytokines (TPO, FLT-3, IL-6 and SCF) and with either (i) TEPA chelator mixed with copper chloride at a 1:1 molar ratio, or with (ii) TEPA chelator mixed with copper chloride and a 1:2 ratio. The densities of colony-forming cells of $CD_{34}^+$ were comparatively measured after seven weeks. The results are presented in FIG. 10 and show that while TEPA mixed with copper chloride at a 1:2 ratio had no significant effect, the treatment of TEPA mixed with copper chloride at a 1:1 ratio substantially increased the number of colony-forming cells of $CD_{34}^+$. Hence, the effect of TEPA mixed with copper chloride at a 1:1 molar ration, was similar to the effect of the TEPA-Cu chelate, described in Example 1 hereinabove. These results insinuate that at the 1:1 ratio treatment, chelation of free ionic copper occurred in culture, such that no free copper was available and hence this treatment resulted in expansion of stem cells, while at the 1:2 ratio treatment, free copper was excessive and this treatment resulted in antagonizing the chelate effect on stem cell expansion.

Figure 11A:
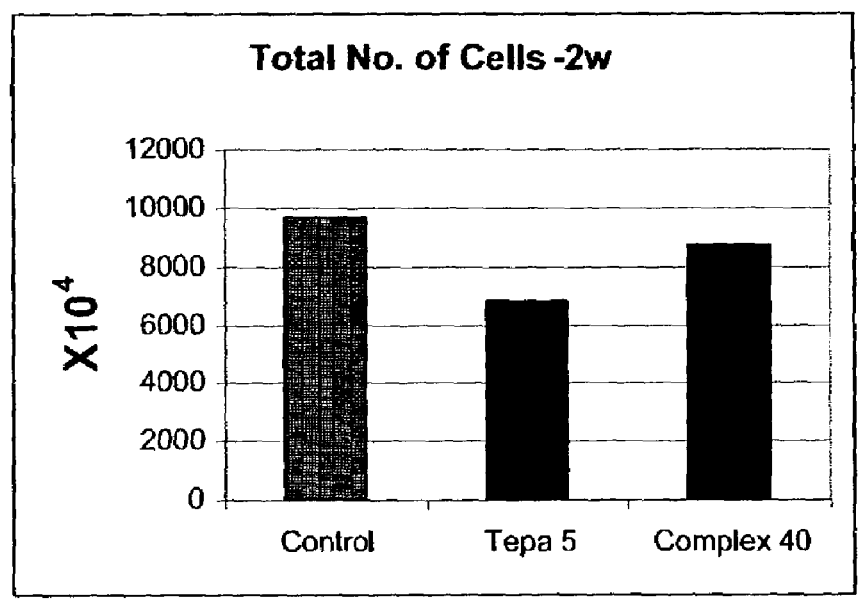
FIGS. 11a-b illustrate the effects of TEPA chelator and TEPA-Cu chelate on the short-term (2 weeks) expansion of stem cells, cultured ex vivo. Purified $CD_{34}^+$ cells were plated in liquid culture in the presence of early cytokines, with TEPA-Cu chelate at a concentration of 40 µM; or with TEPA chelator at a concentration of 5 µM; or untreated (control). The Figures show the comparative numbers of cells measured after 2 weeks incubation (FIG. 11a and FIG. 11b represent two repeated experiments).
Figure 11B:
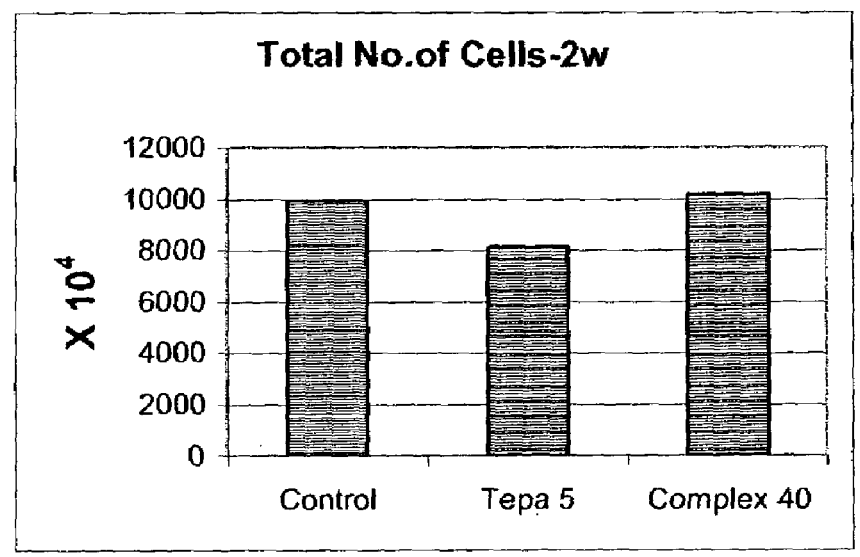

In another experiment the effects of TEPA-Cu chelate and TEPA chelator, were compared. Cultures of enriched $CD_{34}^+$ cell fraction were supplemented with 4 early cytokines (TPO, FLT-3, IL-6 and SCF) and with TEPA-Cu chelate (40 µM), with TEPA chelator (5 µM), or an untreated control (cytokines only). The results are presented in FIGS. 11a-b and show that in the two weeks culture the TEPA-Cu treatment did not significantly affect $CD_{34}^+$ cell expansion, while the TEPA chelator slightly decreased the density of $CD_{34}^+$ cells, as compared with the untreated control.

Figure 12A:
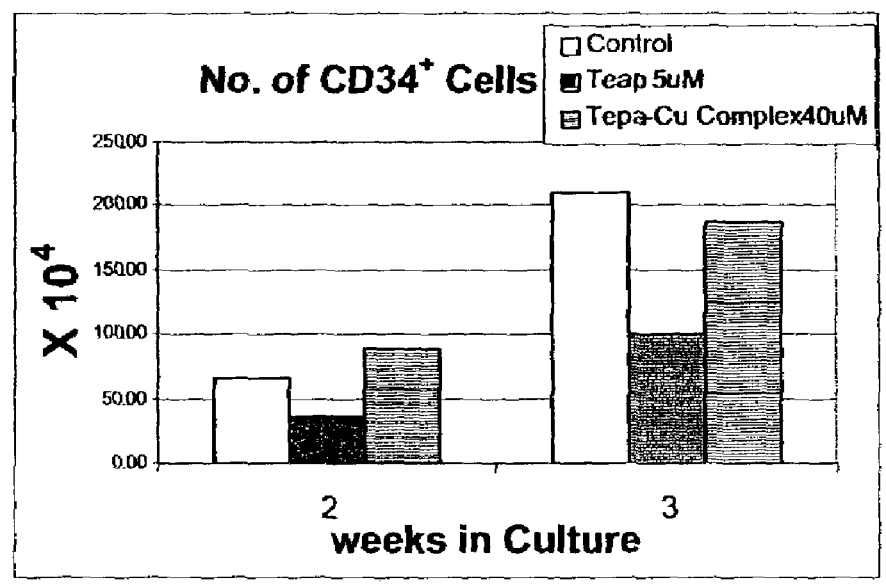
FIGS. 12a-c illustrate the effects of TEPA chelator and TEPA-Cu chelate on the short-term (2 and 3 weeks) expansion of stem and progenitor cells, cultured ex vivo. Purified $CD_{34}^+$ cells were seeded in culture bags in the presence of early cytokines, and with TEPA-Cu chelate at a concentration of 40 µM; or with TEPA chelator at a concentration of 5 µM; or untreated (control). After 2 and 3 weeks of incubation half of the culture bag content was taken for re-purification of $CD_{34}^+$ cells using miniMacs columns. The re-purified cells were numerated for the density of $CD_{34}^+$ cells (FIG. 12a) and FACS-analyzed for the density of $CD_{34}^+ CD_{38}^-$ cells (FIG. 12b) and for the density of $CD_{34}^+$ Lin$^-$ cells (FIG. 12c).
Figure 12B:
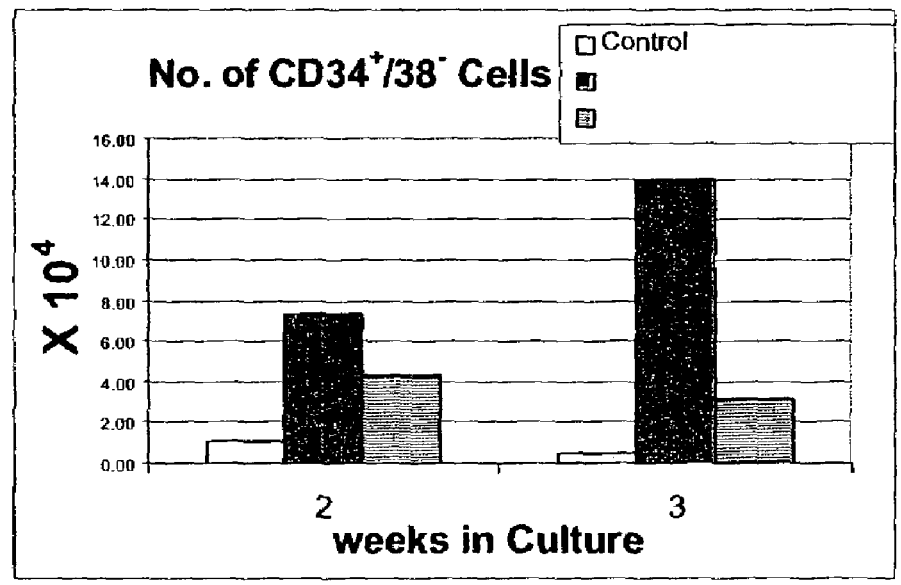
Figure 12C:
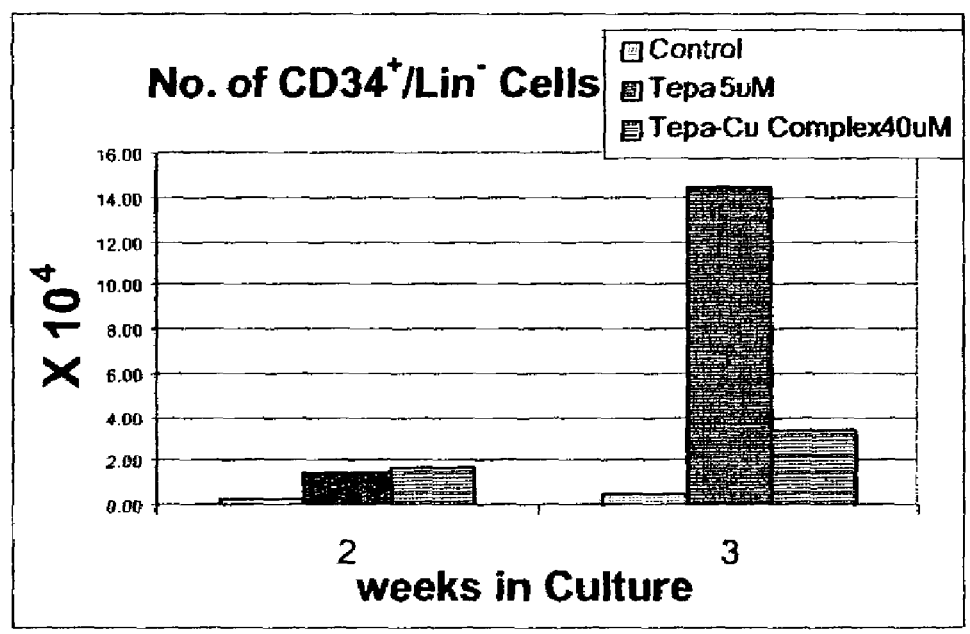
Figure 13A:
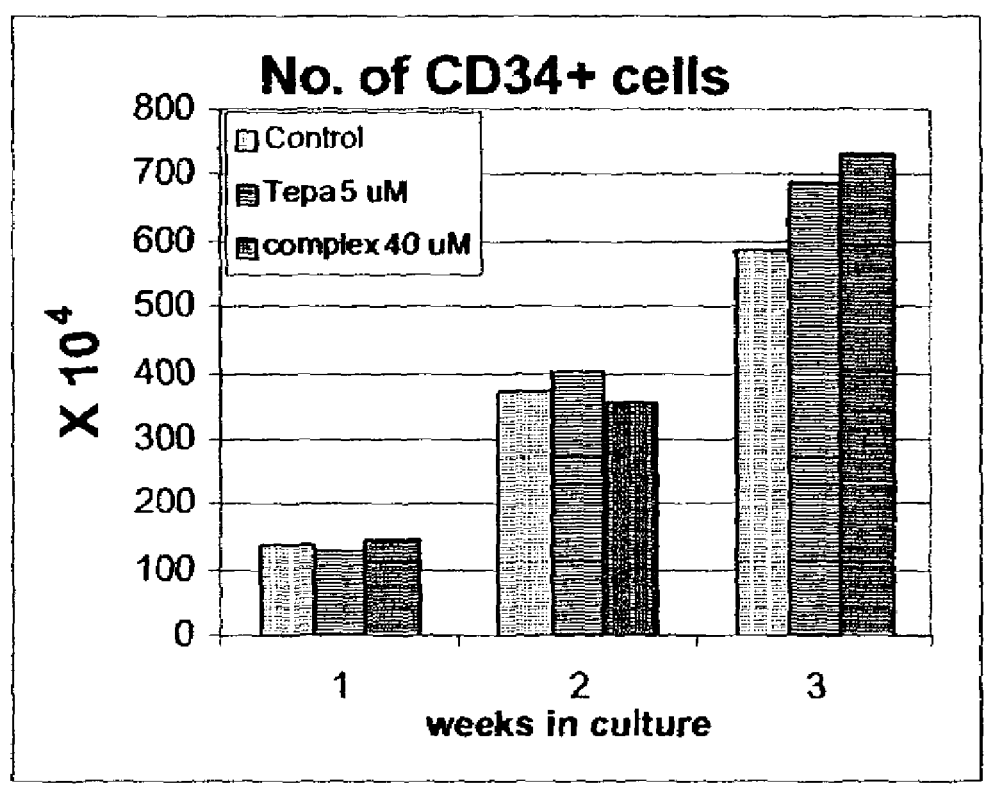
FIGS. 13a-c illustrate the effects of TEPA chelator and TEPA-Cu chelate on the short-term (1 to 3 weeks) expansion of stem and progenitor cells, cultured ex vivo. Purified $CD_{34}^+$ cells were seeded in culture-bags in the presence of early cytokines, and with TEPA-Cu chelate at a concentration of 40 µM; or with TEPA chelator at a concentration of 5 µM; or untreated (control). After 1, 2 and 3 weeks of incubation half of the bag content was taken for re-purification of $CD_{34}^+$ cells using miniMacs columns. The re-purified cells were numerated for the density of $CD_{34}^+$ cells (FIG. 13a) and FACS-analyzed for the density of $CD_{34}^+ CD_{38}^-$ cells (FIG. 13b) and for the density of $CD_{34}^+$ Lin$^-$ cells (FIG. 13c).
Figure 13B:
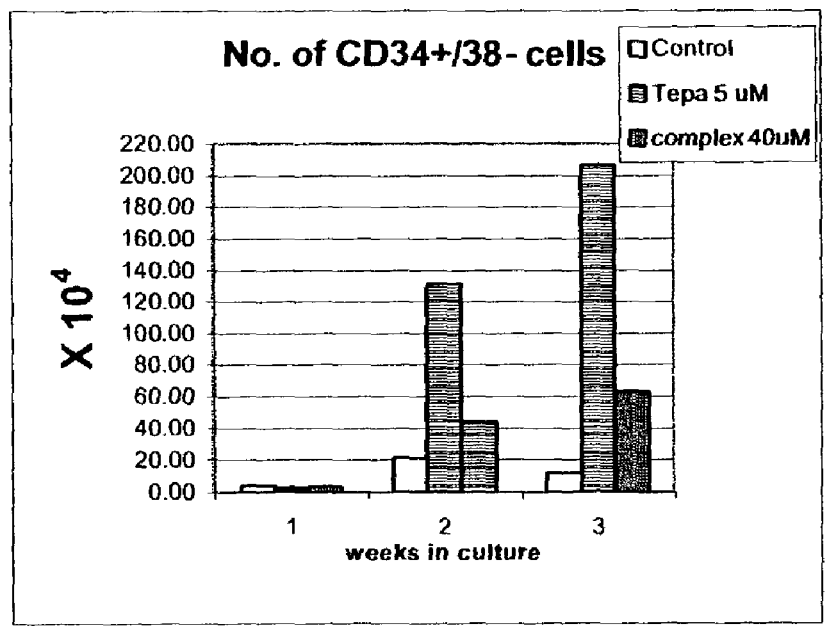
Figure 13C:
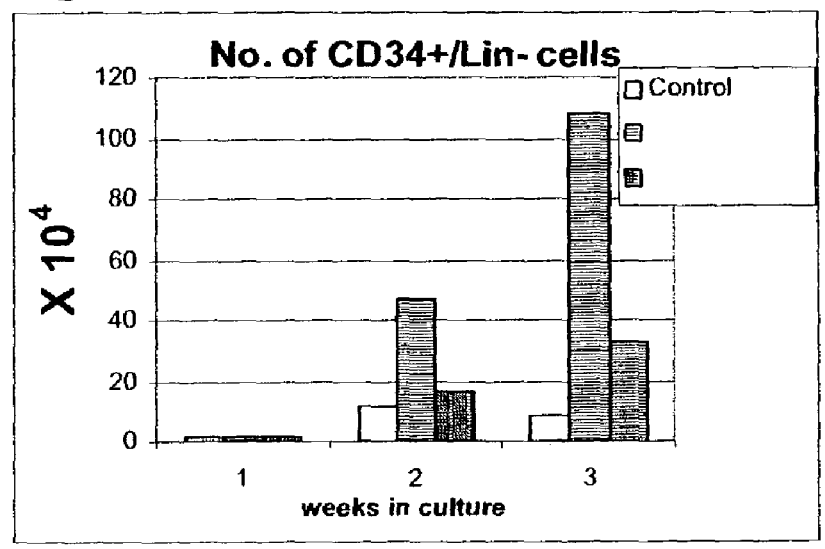
Figure 14A:
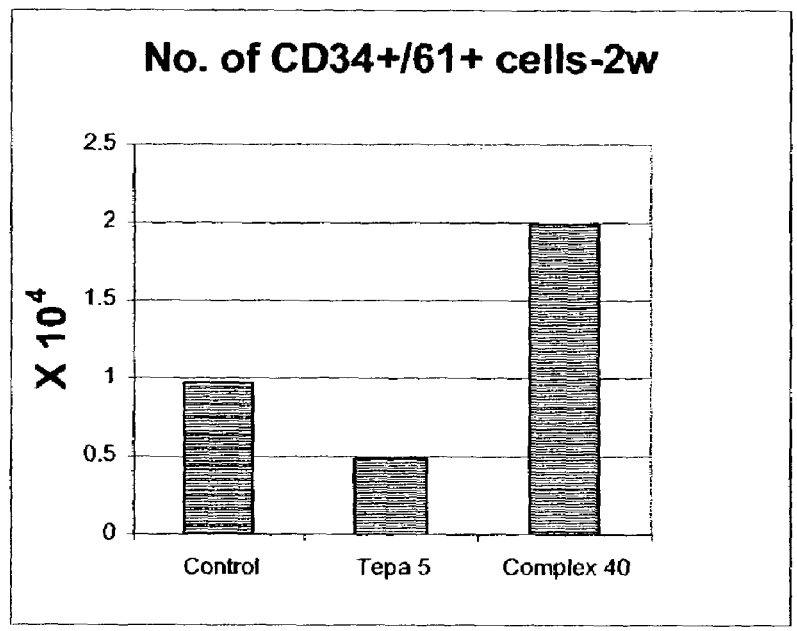
FIGS. 14a-b illustrate the effects of TEPA chelator and TEPA-Cu chelate on the short-term (2 weeks) expansion of lineage-committed progenitor cells, cultured ex vivo. Purified $CD_{34}^+$ cells were seeded in culture-bags in the presence of early cytokines, and with TEPA-Cu chelate at a concentration of 40 µM; or with TEPA chelator at a concentration of 5 µM; or untreated (control). After 2 weeks of incubation half of the bag content was taken for re-purification of $CD_{34}^+$ cells using miniMacs columns. The re-purified cells were FACS-analyzed for the density of $CD_{34}^+ CD_{61}^+$ cells (FIG. 14a) and for the density of $CD_{34}^+ CD_{41}^+$ cells (FIG. 14b).
Figure 14B:
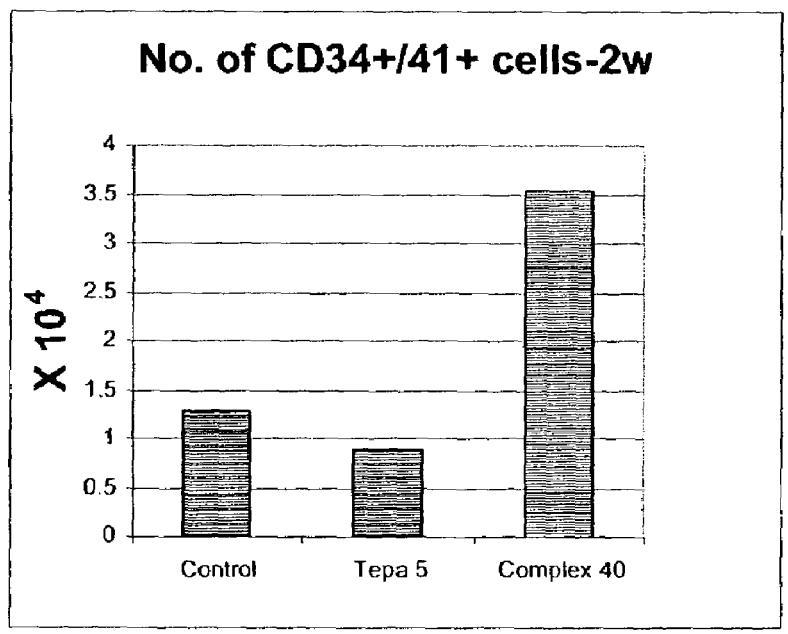

As is shown in FIGS. 12a-c, in another similar experiment, after three weeks incubation period, TEPA treatment substantially increased the density of $CD_{34}^+$ $CD_{38}^-$ and $CD_{34}^+$ Lin$^-$ subset cells, as compared with either the untreated or the TEPA-Cu treatment. As is shown in FIGS. 13a-c, in yet another similar experiment after two and three weeks of incubation period, the TEPA treatment promoted substantially higher densities of $CD_{34}^+$ $CD_{38}^-$ and $CD_{34}^+$ Lin$^-$ cell, as compared with the untreated or the TEPA-Cu treatment.

Hence, these experimental results demonstrate that TEPA chelator is more effective than TEPA-Cu chelate in promoting a short-term (2-3 weeks) expansion of $CD_{34}^+$ $CD_{38}^-$ and $CD_{34}^+$ Lin$^-$ subset cells.

Figure 15A:
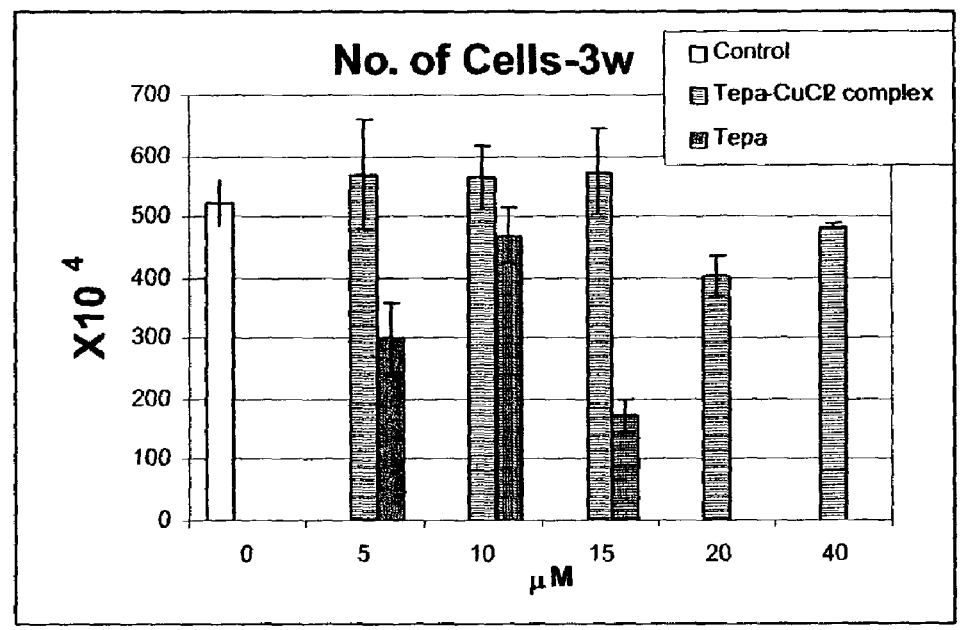
FIGS. 15a-c illustrate the effects of TEPA chelator and TEPA-Cu chelate on the short and long-term (3 to 8 weeks) expansion of stem cells, cultured ex vivo. Purified $CD_{34}^+$ cells were cultured in bags in the presence of early cytokines, with TEPA-Cu chelate; or with TEPA chelator, at different concentrations; or untreated (control). The Figures show the numbers of cells and the numbers of colony-forming cells (CFUs) which were measured from cultures after 3 weeks (FIG. 15a), 5 weeks (FIG. 15b) and 8 weeks (FIG. 15c).
Figure 15A:
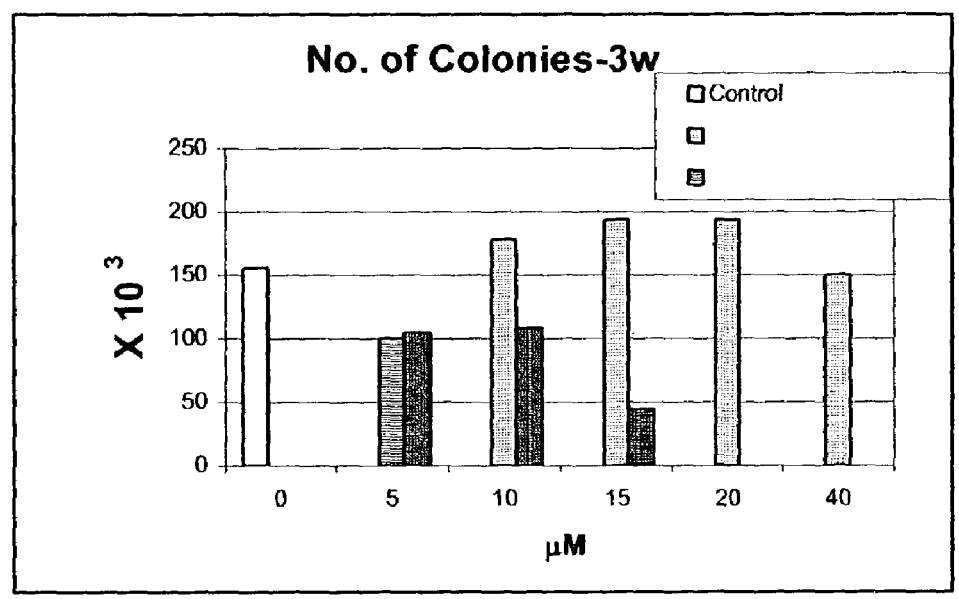
Figure 15B:
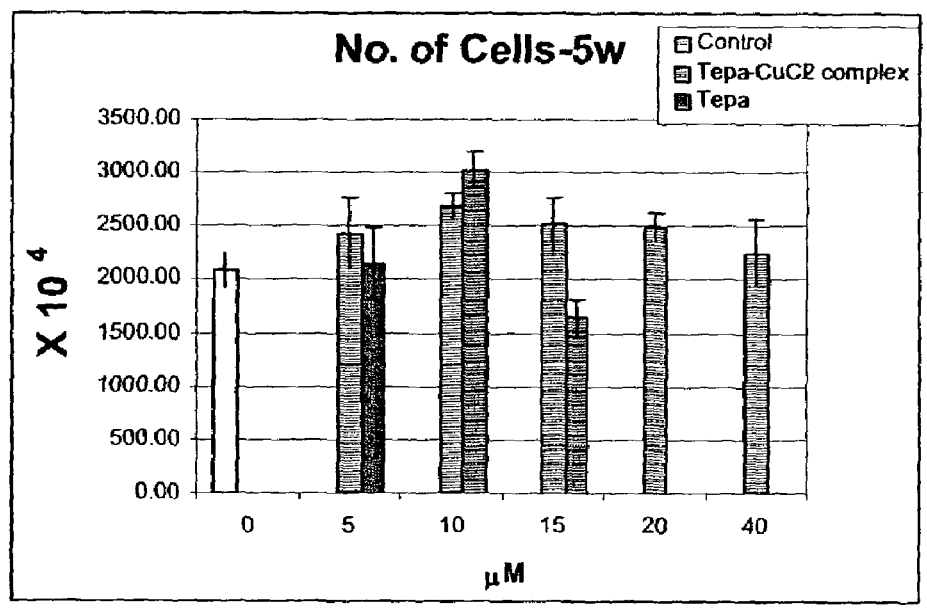
Figure 15B:
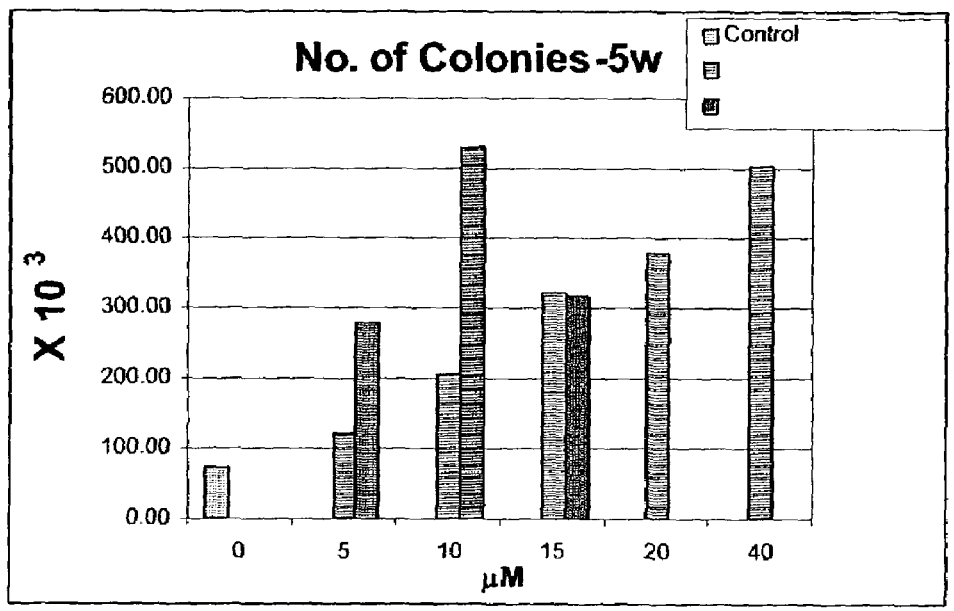
Figure 15C:
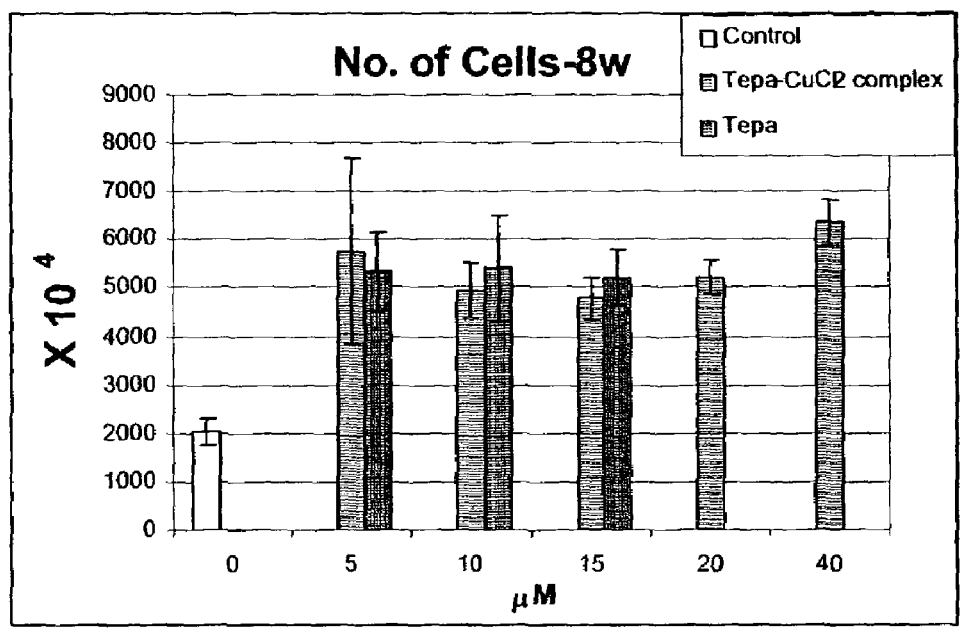
Figure 15C:
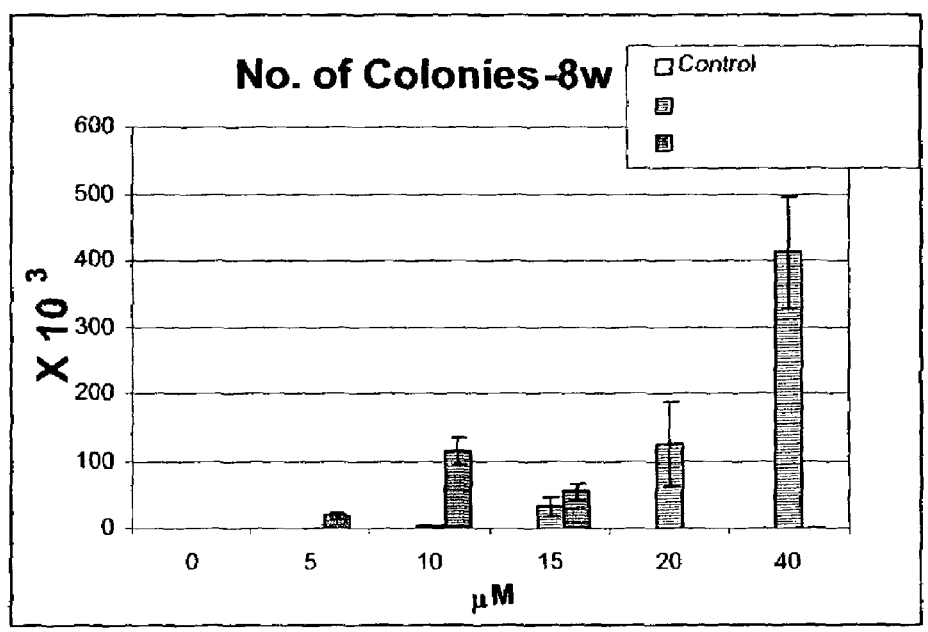
Figure 16A:
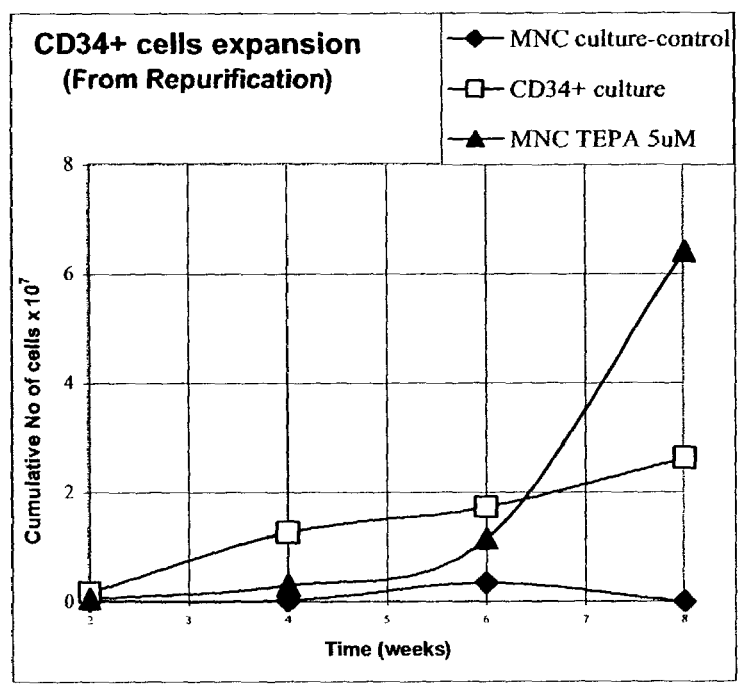
FIGS. 16-18 illustrate the effect of TEPA chelator on the expansion of $CD_{34}^+$ cells in a culture of mixed hematopoietic cells. Cord-blood mononuclear cells (MNC) were seeded in culture-bags in the presence of cytokines, which were either supplemented with TEPA chelator (MNC-TEPA), or not supplemented with TEPA (MNC control). For comparison, purified $CD_{34}^+$ cells were similarly seeded in culture-bags in the presence of cytokines but with no TEPA added ($CD_{34}^+$ culture). All cultures were incubated for 12 weeks and at weekly intervals, the $CD_{34}^+$ cells were purified from cultures using miniMacs columns. The purified $CD_{34}^+$ cells were enumerated (FIGS. 16a-b) and FACS-analyzed for the density of $CD_{34}^+ CD_{38}^-$ cells (FIG. 17).
Figure 16B:
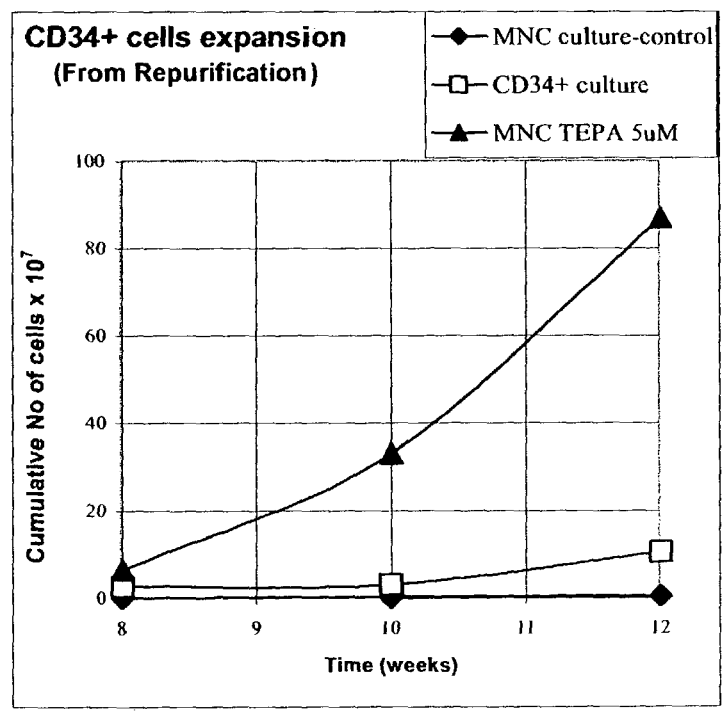
Figure 17:
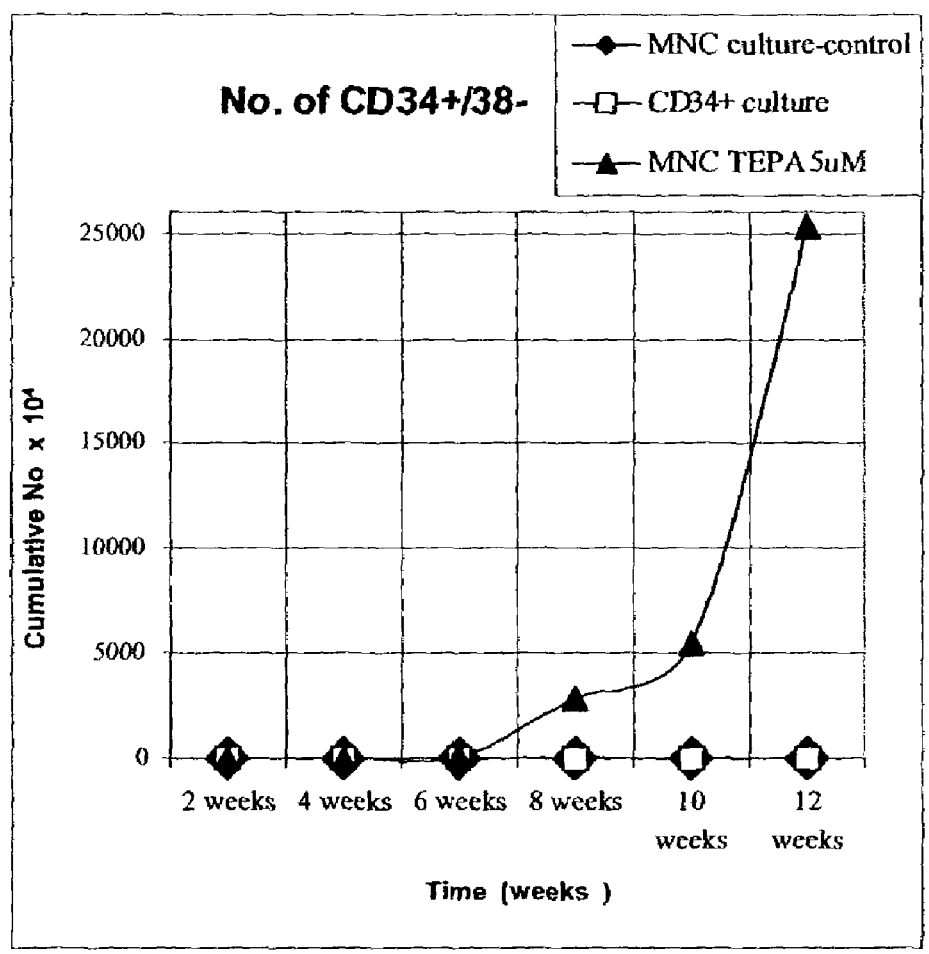

In another experiment the effects of TEPA chelator and TEPA-Cu chelate were comparatively evaluated for the long-term (over 5 weeks) expansion of $CD_{34}^+$ cells. Accordingly, enriched $CD_{34}^+$ cell cultures were supplemented with 4 cytokines (TPO, FLT-3, IL-6 and IL-3) and treated with TEPA-Cu chelate or TEPA chelator, at different concentrations. The results are presented in FIGS. 15a-c and show that both TEPA-Cu chelate and TEPA chelator substantially increased the number of colony-forming cells of $CD_{34}^+$ after 5 and 7 weeks incubation, as compared with the untreated control.

Hence, the results described in this Example show that the compounds TEPA-Cu chelate and TEPA chelator, despite causing opposite effects on cellular-copper content, can both effectively and substantially promote proliferation and inhibit differentiation of stem and progenitor cells ex vivo. In addition, these results indicate that the two different compounds may differently regulate sub populations of stem and progenitor cells.

Example 4

The Effect of a Copper Chelator on the Ex Vivo Expansion of Stem and Progenitor Cells in a Mixed Cells Culture

Experimental Procedures

Sample collection and processing: Samples were obtained from umbilical cord blood after a normal full-term delivery and were frozen within 24 hours pospartum. The blood cells were thawed in Dextran buffer and incubated for 15 hours in MEM (Biological Industries, Israel) supplemented with 10% fetal calf serum (FCS; Biological Industries). The cells were then layered on Ficoll-Hypaque (density 1.077 gram/ml; Sigma) and centrifuged at 400 g for 30 minutes at room temperature. The mononuclear cells in the interface layer were then collected, washed three times in phosphate-buffered saline (PBS; Biological Industries), and re-suspended in PBS containing 0.5% human serum albumin (HSA). The cells were then split into two fractions, the first being the mononuclear cells (MNC) and the second fraction was used for purifying $CD_{34}^+$ cells by immunomagnetic separation using the "MiniMACS $CD_{34}^+$ progenitor cell isolation kit" (Miltenyi Biotec, Auburn, Calif.) according to the manufacturer's recommendations. The purity of the $CD_{34}^+$ cells obtained ranged between 95% and 98%, based on Flow Cytometry evaluation (see below).

Ex vivo expansion of progenitor cells: The non-purified mononuclear cells (MNC), obtained as described hereinabove, were seeded in Culture Bags (American Fluoroseal Corp.), with alpha minimal essential medium supplemented with 10% fetal bovine serum (FBS, Biological Industries), at a concentration of about $10^6$ cells/ml. The purified $CD_{34}^+$ cells were similarly seeded in the Culture Bags, at a concentration of about $10^4$ cells/ml. The media were supplemented with TEPA chelator and/or with the following human recombinant cytokines (all obtained from Perpo Tech, Inc., Rocky Hill, N.J.): Thrombopoietin (TPO), 50 ng/ml; interleukin 6 (IL-6), 50 ng/ml; FLT-3 ligand, 50 ng/ml and a stem cell factor (SCF), 50 ng/ml; occasionally SCF was replaced by IL-3, 20 ng/ml. For non-hemopoietic differentiation, FGF, EGF, NGF, VEGF, LIF or Hepatocyte growth factor, were used alone or in various combinations. All cultures were incubated at 37° C. in an atmosphere of 5% $CO_2$ in air with extra humidity. At weekly intervals, the cell cultures were semi-depopulated and supplemented with fresh medium containing cytokines. Following different incubation periods, cells were harvested, stained with trypan blue and enumerated.

Cloning potential evaluation, morphological assessment and surface antigen analyses were carried out as described in the experimental procedures section of Example 1 above.

Determining the density of stem and progenitor subset populations following expansion was carried out as described in the experimental procedures section of Example 3 above.

Experimental Results

Non-purified mononuclear cells (MNC) were seeded in culture bags and were provided with nutrients and cytokines as described above. The MNC cultures were either treated or untreated (untreated controls) with TEPA-chelator. The treated MNC cultures were supplemented with TEPA for only the first three weeks and from week three onward were topped with chelator-free media. The pre-purified $CD_{34}^+$ cultures were not supplemented with TEPA and served as positive controls. The cultures were analyzed weekly during a 12-week period.

Figure 18:
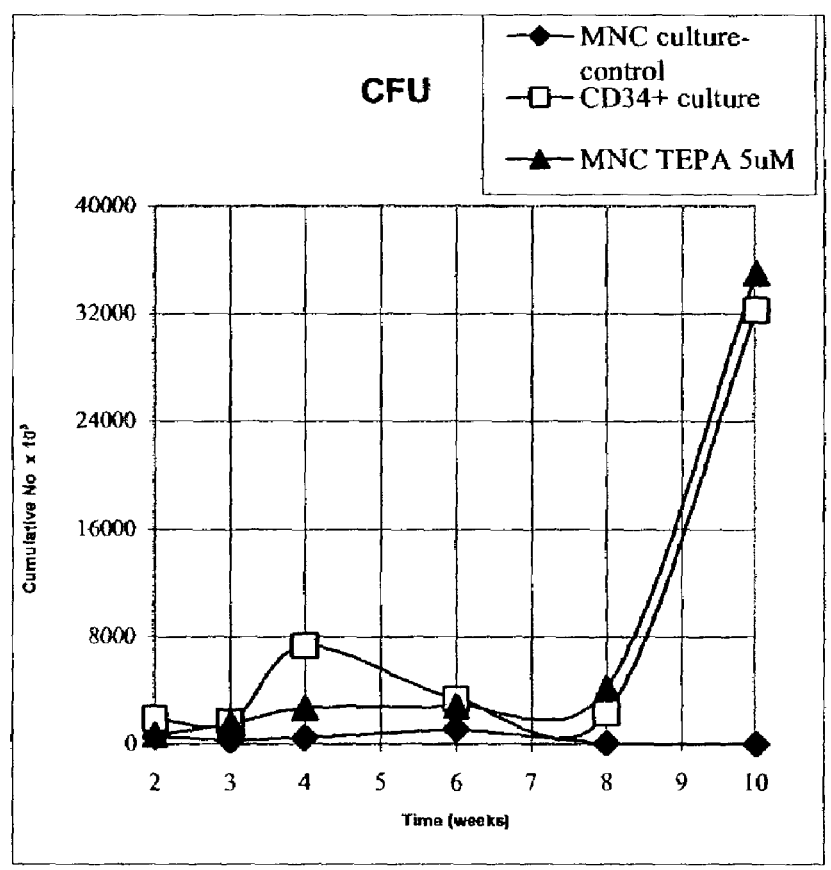

The results, illustrated in FIGS. 16a-b, 17 and 18, show that addition of TEPA chelator to non-purified MNC cultures, substantially and progressively increased the number of $CD_{34}^+$ cells, $CD_{34}^+$ colony-forming cells and $CD_{34}^+$ $CD_{38}^-$ cells, over a 12-week period. Thus, in MNC cultures treated with TEPA, the cumulative number of $CD_{34}^+$ cells increased from a non-detectable level to over $8 \times 10^7$ cells/ml, after 2 and 12 weeks, respectively (FIGS. 16a-b); the cumulative number of $CD_{34}^+$ $CD_{38}^-$ cells increased from a non-detectable level to $2.5 \times 10^7$ cells/ml, after 2 and 12 weeks, respectively (FIG. 17); and the number of $CD_{34}^+$ CFUs increased from a non-detectable level to $3.2 \times 10^7$ cells/ml after 2 and 10 weeks, respectively (FIG. 18). On the other hand, when TEPA was not added to MNC cultures (untreated controls), no significant expansion of stem or progenitor cells was measured throughout the 12-week period. Furthermore, the of stem and progenitor cells densities in the TEPA-treated MNC cultures, either equalized or surpassed the densities of stem and progenitor cells in pre-purified $CD_{34}^+$ cells cultures (not treated with TEPA, positive controls). Morphological analysis of cells derived from long-term and TEPA-treated MNC cultures, revealed a high proportion of non-differentiated cells, while most of the cells derived from long-term and MNC cultures not treated with TEPA, where fully differentiated.

The results described in this Example clearly show that stem and progenitor hematopoietic cells may be substantially expanded ex vivo, continuously over at least 12 weeks period, in a culture of mixed (mononuclear fraction) blood cells, with no prior purification of $CD_{34}^+$ cells. The data also show that this effect resulted from supplementing the cells culture medium with TEPA chelator, during just the first three weeks of culturing.

Hence, this Example illustrates a substantial ex vivo expansion of stem and progenitor cells in a mixed cells culture. This novel procedure circumvents the need of the laborious and costly enrichment of stem cells prior to initiation of cultures, which is currently used in the art. Hence, the use of a copper chelator, such as TEPA, can substantially simplify, reduce cost and improve efficiency of procedures for an ex vivo expansion of stem and/or progenitor cells.

Example 5

The Effect of a Copper Chelate on the Ex Vivo Expansion of Stem and Progenitor Cells in a Mixed Cells Culture Non-purified (mixed cells) mononuclear cells (MNC) were seeded in culture bags and were provided with nutrients and cytokines as described in Example 4 above. The mixed cell cultures were either untreated (control) or treated with Cu-TEPA chelate. The treated MNC cultures were supplemented with Cu-TEPA chelate for only the first three weeks and from week three onward were topped with chelator-free media. All cultures were analyzed 8 weeks after an 8-week period.

The results, illustrated in Table 2 below, show that addition of Cu-TEPA chelate to the mixed cells (MNC) cultures, markedly increased the number of $CD_{34}^+$ cells, the proportion of $CD_{34}^+$ cells, and the number of $CD_{34}^+$ $CD_{38}^-$ cells, after an 8 weeks incubation period. Thus, the cumulative number of $CD_{34}^+$ cells per culture bag after incubation was $2.56 \times 10^6$, $12.37 \times 10^6$ or $32.85 \times 10^6$, in the control (cytokines only), 50 µM Cu-TEMA and 100 µM Cu-TEPA supplemented treatments, respectively. The cumulative number of $CD_{34}^+$ $CD_{38}^-$ cells increased from $2.1 \times 10^5$ in the control culture (cytokines only) to $6.1 \times 10^5$ in the Cu-TEPA (100 µM) supplemented treatment.

TABLE 2

The effect of Cu-TEPA chelate on the ex vivo expansion of stem and progenitor cells in cultures* initiated with mixed hematopoietic cells

| Treatment | Number of CD34+ cells ($\times 10^4$) | Portion of CD34+ cells (%) | Nunber of CD34/38− cells ($\times 10^4$) |
|---|---|---|---|
| Control | 256.0 | 0.2 | 21 |
| Cu-TEPA chelate 50 µM | 1237.3 | 1.4 | — |
| Cu-TEPA chelate 100 µM | 3285.3 | 1.2 | 61 |

*Eight weeks after seeding

The results described in this Example demonstrate that stem and progenitor hematopoietic cells may be substantially expanded ex vivo, over at least 8 weeks period, in a culture of mixed (mononuclear fraction) blood cells, with no prior purification of $CD_{34}^+$ cells. This novel procedure circumvents the need of the laborious and costly enrichment of stem cells prior to initiation of cultures, which is currently used in the art. Hence, the use of a copper chelate, such as Cu-TEPA, can substantially simplify, reduce cost and improve efficiency of procedures for an ex vivo expansion of stem and/or progenitor cells.

Example 6

The Effect of a Copper Chelate on the In Vivo Recovery of Platelets

In this experiment, ten mice (BALB/C X C57B1/6/F1) were gamma-irradiated (700 cGy) so as to mimic an irradiation therapy situation that destroys platelets. One day after irradiation five (out of ten) mice were administered with 30 µM of Cu-TEPA, while the other five mice were non-treated. The platelet levels in all mice were enumerated one week after irradiation. The results, presented in Table 3 bellow, show that a single treatment of Cu-TEPA significantly accelerated the recovery of platelets, as compared with the non-treated control. The results of this experiment illustrate that a copper chelate can effectively enhance the recovery of hematopoietic cells in subjects exposed to irradiation treatment.

TABLE 3

| Treatment | Platelet Density (cells/ml) |
| --- | --- |
| TEPA-Cu (30 µM) | 400.8 (±50.0)* |
| Untreated Control | 285.0 (±84.0)* |

*Mean ± SD

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

LIST OF REFERENCES CITED

1. Van Epps D E, et al. Harvesting, characterization, and culture of $CD_{34}$+ cells from human bone marrow, peripheral blood, and cord blood. Blood Cells 20:411, 1994.

2. Emerson S G. Ex-vivo expansion of hematopoietic precursors, progenitors, and stem cells: The next generation of cellular therapeutics. Blood 87:3082, 1996.

3. Brugger W, et al. Reconstitution of hematopoiesis after high-dose chematotherapy by autologus progenitor cells generated in-vivo. N Engl J Med 333:283, 1995.

4. Williams S F, et al. Selection and expansion of peripheral blood $CD_{34}$+ cells in autologous stem cell transplantation for breast cancer. Blood 87:1687, 1996.

5. Zimmerman R M, et al. Large-scale selection of $CD_{34}$+ peripheral blood progenitors and expansion of neutrophil precursors for clinical applications. J Heamatotherapy 5:247, 1996.

6. Koller M R, Emerson S G, Palsson B O. Large-scale expansion of human stem and progenitor cells from bone marrow mononuclear cells in continuous perfusion cultures. Blood 82:378, 1993.

7. Lebkowski J S, et al. Rapid isolation and serum-free expansion of human $CD_{34}$+ cells. Blood Cells 20:404, 1994.

8. Sandstrom C E, et al. Effects of $CD_{34}$+ cell selection and perfusion on ex-vivo expansion of peripheral blood mononuclear cells. Blood 86:958, 1995.

9. Eiprs P G, et al. Retroviral infection of primitive hematopoietic cells in continuous perfusion culture. Blood 86:3754, 1995.

10. Freedman A R, et al. Generation of T lymphocytes from bone marrow $CD_{34}$+ cells in-vitro. Nature Medicine 2:46, 1996.

11. Heslop H E, et al. Long term restoration of immunity against Epstein-Barr virus infection by adoptive transfer of gene-modified virus-specific T lymphocytes. Nature Medicine 2:551, 1996.

12. Protti M P, et al. Particulate naturally processed peptides prime a cytotoxic response against human melanoma in-vitro. Cancer Res 56:1210, 1996.

13. Rosenberg S A, et al. Prospective randomized trial of high-dose interleukin-2 alone or in conjunction with lymphokine-activated killer cells for the treatment of patients with advanced cancer. J Natl Cancer Inst. 85:622, 1993.

14. Bernhard H, et al. Generation of immunostimulatory dendritic cells from human $CD_{34}$+ hematopoietic progenitor cells of the bone marrow and peripheral blood. Cancer Res 1099, 1995.

15. Fisch P, et al. Generation of antigen-presenting cells for soluble protein antigens ex-vivo from peripheral blood $CD_{34}$+ hematopoietic progenitor cells in cancer patients. Eur J Immunol 26:595, 1996.

16. Siena S, et al. Massive ex-vivo generation of functional dendritic cells from mobilized $CD_{34}$+ blood progenitors for anticancer therapy. Expt Hematol 23:1463, 1996.

17. Petzer A L, Zandstra P W, Piret J M, Eaves C J. Differential cytokine effecton primitive ($CD_{34}$+ CD38−) human hematopoietic cells: novel responses to FlT3-ligand and thrombopoietin. J Exp Med 183:2551, 1996.

18. Alter B P. Fetal erythropoiesis in stress hemopoiesis. Experimental Hematology 7:200, 1979.

19. Repair of myelin disease: Strategies and progress in animal models. Molecular Medicine Today. December 1997. pp. 554-561.

20. Blau C A et al. Fetal hemoglobin in acute and chronic stage of erythroid expansion. Blood 81:227, 1993.

21. Schechtez A N et al. Sickle cell anemia. In: Molecular basis of blood diseases. Stamatoyannaopoulos G, Nienhuis A W, Leder P and Majerus PW Eds. pp. 179-218, Sounders Philadelphia.

22. Ross J W and Frant M S. Chelometric indicators, titration with the solid state cupric ion selective electrode. Analytical Chemistry 41:1900, 1969.

23. Spangrude, G. J., Heimfeld, S. & Weissman, I. L. Purification and characterization of mouse hematopoietic stem cells. *Science* 241, 58-62 (1988).

24. Morrison, S. J. & Weissman, I. L. The long-term repopulating subset of hematopoietic stem cells is deterministic and isolatable by phenotype. *Immunity* 1, 661-673 (1994).

25. Baum, C. M., Weissman, I. L., Tsukamoto, A. S., Buckle, A. M. & Peault, B. Isolation of a candidate human hematopoietic stem-cell population. *Proc. Natl Acad. Sci. USA* 89, 2804-2808 (1992).

26. Osawa, M., Hanada, K., Hamada, H. & Nakauchi, H. Long-term lymphohematopoietic reconstitution by a single CD34-low/negative hematopoietic stem cell. *Science* 273, 242-245 (1996).

27. Akashi, K. & Weissman, I. L. in *Developmental Biology of Hematopoiesis* (ed. Zon, L. I.) 15-34 (Oxford Univ. Press, New York, 2001).

28. Petersen, B. E. et al. Bone marrow as a potential source of hepatic oval cells. *Science* 284, 1168-1170 (1999).

29. Brazelton, T. R., Rossi, F. M. V., Keshet, G. I. & Blau, H. M. From marrow to brain: expression of neuronal phenotypes in adult mice. *Science* 290, 1775-1779 (2000).

30. Mezey, E., Chandross, K. J., Harta, G., Maki, R. A. & McKercher, S. R. Turning blood into brain: cells bearing neuronal antigens generated in vivo from bone marrow. *Science* 290, 1779-1782 (2000).

31. Lagasse, E. et al. Purified hematopoietic stem cells can differentiate to hepatocytes in vivo. *Nature Med.* 6, 1229-1234 (2000).

32. Krause, D. S. et al. Multi-organ, multi-lineage engraftment by a single bone marrow derived stem cell. *Cell* 105, 369-377 (2001).

33. Morrison, S. J., Wandycz, A. M., Hemmati, H. D., Wright, D. E. & Weissman, I. L. Identification of a lineage of multipotent hematopoietic progenitors. *Development* 124, 1929-1939 (1997).

34. Weissman, I. L. Translating stem and progenitor cell biology to the clinic: barriers and opportunities. *Science* 287, 1442-1446 (2000).

35. Miller, C. L. & Eaves, C. J. Expansion in vitro of adult murine hematopoietic stem cells with transplantable lympho-myeloid reconstituting ability. *Proc. Natl Acad. Sci. USA* 94, 13648-13653 (1997).

36. Peled T., Landau. E., Prus E., Treves A. J., Fibach E., Cellular copper content modulates differentiation and self-renewal in cultures of cord-blood derived $CD_{34}^+$ cells. British journal of hematology, 2002, 116, 1-7.

37. Puccetti E, Obradovic D, Beissert T, Bianchini A, Washburn B, Chiaradonna F, Boehrer S, Hoelzer D, Ottmann O G, Pelicci P G, Nervi C, Ruthardt M. AML-associated translocation products block vitamin D(3)-induced differentiation by sequestering the vitamin D(3) receptor. Cancer Res. 2002 Dec. 1;62 (23):7050-8.

38. Grenda D S, Johnson S E, Mayer J R, McLemore M L, Benson K F, Horwitz M, Link D C. Mice expressing a neutrophil elastase mutation derived from patients with severe congenital neutropenia have normal granulopoiesis. Blood. 2002 Nov. 1;100 (9):3221-8.

39. Ferbeyre G. PML a target of translocations in APL is a regulator of cellular senescence. Leukemia. 2002 October; 16(10):1918-26.

40. Cote S, Rosenauer A, Bianchini A, Seiter K, Vandewiele J, Nervi C, Miller W H Jr. Response to histone deacetylase inhibition of novel PML/RARalpha mutants detected in retinoic acid-resistant APL cells. Blood. 2002 Oct. 1;100 (7):2586-96.

41. Petti M C, Fazi F, Gentile M, Diverio D, De Fabritiis P, De Propris M S, Fiorini R, Spiriti M A, Padula F, Pelicci P G, Nervi C, Lo Coco F. Complete remission through blast cell differentiation in PLZF/RARalpha-positive acute promyelocytic leukemia: in vitro and in vivo studies. Blood. 2002 Aug. 1;100(3):1065-7.

42. Mueller B U, Pabst T, Osato M, Asou N, Johansen L M, Minden M D, Behre G, Hiddemann W, Ito Y, Tenen D G. Heterozygous PU.1 mutations are associated with acute myeloid leukemia. Blood. 2002 Aug. 1;100(3):998-1007.

43. Spangrude, G. J., Heimfeld, S. & Weissman, I. L. Purification and characterization of mouse hematopoietic stem cells. *Science* 241, 58-62 (1988).

44. Morrison, S. J. & Weissman, I. L. The long-term repopulating subset of hematopoietic stem cells is deterministic and isolatable by phenotype. *Immunity* 1, 661-673 (1994).

45. Baum, C. M., Weissman, I. L., Tsukamoto, A. S., Buckle, A. M. & Peault, B. Isolation of a candidate human hematopoietic stem-cell population. *Proc. Natl Acad. Sci. USA* 89, 2804-2808 (1992).

46. Osawa, M., Hanada, K., Hamada, H. & Nakauchi, H. Long-term lymphohematopoietic reconstitution by a single CD34-low/negative hematopoietic stem cell. *Science* 273, 242-245 (1996).

47. Akashi, K. & Weissman, I. L. in *Developmental Biology of Hematopoiesis* (ed. Zon, L. I.) 15-34 (Oxford Univ. Press, New York, 2001).

What is claimed is:

1. A method of ex vivo expanding a population of hematopoietic stem and/or progenitor cells, while at the same time reversibly inhibiting differentiation of the stem and/or progenitor cells, the method comprising:
   providing the stem and/or progenitor cells with conditions for cell proliferation and with an effective amount of TEPA-Cu chelate, wherein a free copper concentration available to said cells is not decreased relative to a similar cells not treated with said TEPA-Cu chelate, to thereby expand the population of said stem and/or progenitor cells, while at the same time reversibly inhibit differentiation of said stem and/or progenitor cells.

2. The method of claim 1, wherein providing said stem and/or progenitor cells with said conditions for cell proliferation include providing said stem and/or progenitor cells with nutrients and cytokines.

3. The method of claim 2, wherein said cytokines are early acting cytokines.

4. The method of claim 3, wherein said early acting cytokines are selected from the group consisting of stem cell factor, FLT-3 ligand, interleukin-6, thrombopoietin and interleukin-3.

5. The method of claim 2, wherein said cytokines are late acting cytokines.

6. The method of claim 5, wherein said late acting cytokines are selected from the group consisting of granulocyte colony stimulating factor, granulocyte/macrophage colony stimulating factor and erythropoietin.

7. The method of claim 1, wherein said hematopoietic cells are derived from a source selected from the group consisting of bone marrow, peripheral blood and neonatal umbilical cord blood.

8. The method of claim 1, wherein said hematopoietic cells are enriched for $CD_{34}+$ cells.

9. The method of claim 1, wherein said hematopoietic cells are enriched for stem and/or progenitor cells.

10. The method of claim 1, wherein said cells stem and/or progenitor are selected from the group consisting of non-differentiated stem cells and early progenitor cells.

11. A method of ex vivo expanding a population of hematopoietic stem and/or progenitor cells, while at the same time reversibly inhibiting differentiation of the stem and/or progenitor cells, the method comprising:
   providing a TEPA-Cu chelate; and thereafter
   mixing an effective amount of said TEPA-Cu chelate with a cell growth medium, said cell growth medium for providing said stem and/or progenitor cells with conditions for cell proliferation, and with said population of stem and/or progenitor cells, wherein a free copper concentration available to said cells is not decreased relative to a similar cells not treated with said TEPA-Cu chelate by said mixing, to thereby expand the population of said stem and/or progenitor cells, while at the same time reversibly inhibit differentiation of said stem and/or progenitor cells.

12. The method of claim 11, wherein providing said stem and/or progenitor cells with said conditions for cell proliferation include providing said stem and/or progenitor cells with nutrients and cytokines.

13. The method of claim 12, wherein said cytokines are early acting cytokines.

14. The method of claim 13, wherein said early acting cytokines are selected from the group consisting of stem cell factor, FLT3 ligand, interleukin-6, thrombopoietin and interleukin-3.

15. The method of claim 12, wherein said cytokines are late acting cytokines.

16. The method of claim 15, wherein said late acting cytokines are selected from the group consisting of granulocyte colony stimulating factor, granulocyte/macrophage colony stimulating factor and erythropoietin.

17. The method of claim 11, wherein said hematopoietic cells are derived from a source selected from the group consisting of bone marrow, peripheral blood and neonatal umbilical cord blood.

18. The method of claim 11, wherein said hematopoietic cells are enriched for stem and/or progenitor cells.

19. The method of claim 11, wherein said hematopoietic cells are enriched for $CD_{34}+$ cells.

20. The method of claim 11, wherein said stem and/or progenitor cells are selected from the group consisting of non-differentiated stem cells and progenitor cells.

21. A method of ex vivo expanding a population of hematopoietic stem and/or progenitor cells, while at the same time reversibly inhibiting differentiation of the stem and/or progenitor cells, the method comprising:
  (a) obtaining from a donor a mixed population of cells said mixed population of cells comprises the stem and/or progenitor cells; and
  (b) culturing said mixed population of cells ex vivo under conditions for proliferation of said stem and/or progenitor cells and with an effective amount of a TEPA-Cu chelate, to thereby expand the population of said stem and/or progenitor cells, while at the same time reversibly inhibit differentiation of said stem and/or progenitor cells.

22. The method of claim 21, wherein said stem and/or progenitor cells are selected from the group consisting of non-differentiated stem cells and early progenitor cells.

23. The method of claim 21, wherein said mixed population of cells is derived from a source selected from the group consisting of bone marrow, peripheral blood and neonatal umbilical cord blood.

24. The method of claim 21, wherein said mixed population of cells includes a mononuclear fraction of neonatal umbilical cord blood cells.

25. The method of claim 21, wherein said conditions for proliferation of said stem and/or progenitor cells include providing said mixed population of cells with nutrients and cytokines.

26. The method of claim 25, wherein said cytokines are early acting cytokines.

27. The method of claim 26, wherein said early acting cytokines are selected from the group consisting of stem cell factor, FLT3 ligand, interleukin-6, thrombopoietin and interleukin-3.

28. The method of claim 25, wherein said cytokines are late acting cytokines.

29. The method of claim 28, wherein said late acting cytokines are selected from the group consisting of granulocyte colony stimulating factor, granulocyte/macrophage colony stimulating factor and erythropoietin.

30. The method of claim 21 further comprising separating said stem or/or progenitor cells from said mixed population of cells.

* * * * *

UNITED STATES PATENT AND TRADEMARK OFFICE
CERTIFICATE OF CORRECTION

PATENT NO.        : 7,344,881 B2
APPLICATION NO. : 10/418639
DATED             : March 18, 2008
INVENTOR(S)      : Peled et al.

It is certified that error appears in the above-identified patent and that said Letters Patent is hereby corrected as shown below:

Column 56, line 26-27, claim 1, "a free copper concentration available to said cells is not decreased" should read --total intracellular copper content of said cells increases--.

Column 57, line 2-3, claim 11, "a free copper concentration available to said cells is not decreased" should read --total intracellular copper content of said cells increases--.

Column 58, line 4, claim 21, --wherein total intracellular copper content of said cells increases relative to similar cells not treated with said TEPA-Cu chelate-- should be added following the phrase "with an effective amount of a TEPA-Cu chelate".

Signed and Sealed this

Seventeenth Day of June, 2008

JON W. DUDAS
*Director of the United States Patent and Trademark Office*